(12) United States Patent
Akada et al.

(10) Patent No.: US 7,494,987 B2
(45) Date of Patent: Feb. 24, 2009

(54) AGENT FOR TREATING RESPIRATORY DISEASES CONTAINING 4-HYDROXYPIPERIDINE DERIVATIVE AS ACTIVE INGREDIENT

(75) Inventors: Yasushige Akada, Shinjuku-ku (JP); Kazuyuki Matsuura, Shinjuku-ku (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 601 days.

(21) Appl. No.: 10/536,459

(22) PCT Filed: Nov. 25, 2003

(86) PCT No.: PCT/JP03/15005

§ 371 (c)(1),
(2), (4) Date: May 25, 2005

(87) PCT Pub. No.: WO2004/048326

PCT Pub. Date: Jun. 10, 2004

(65) Prior Publication Data

US 2006/0040985 A1    Feb. 23, 2006

(30) Foreign Application Priority Data

Nov. 25, 2002    (JP)    ............... 2002-341251

(51) Int. Cl.
A61K 31/397    (2006.01)
C07D 205/04    (2006.01)
(52) U.S. Cl. ............... 514/210.01; 548/952
(58) Field of Classification Search ............ 514/210.01; 548/952
See application file for complete search history.

(56) References Cited

U.S. PATENT DOCUMENTS

| | | | |
|---|---|---|---|
| 4,508,724 | A | 4/1985 | Taylor, Jr. et al. |
| 6,642,257 | B2 | 11/2003 | Yamamoto et al. |
| 6,710,060 | B2 | 3/2004 | Yamamoto et al. |
| 2004/0176410 | A1 | 9/2004 | Yamamoto et al. |

FOREIGN PATENT DOCUMENTS

| | | |
|---|---|---|
| EP | 0 152 236 A2 | 8/1985 |
| EP | 0 823 896 A1 | 2/1998 |
| EP | 0 934 271 A1 | 8/1999 |
| WO | WO 93/02052 A1 | 2/1993 |
| WO | WO 96/34857 A1 | 11/1996 |
| WO | WO 98/18761 A1 | 5/1998 |
| WO | WO 00/06544 A1 | 2/2000 |
| WO | WO 00/06545 A1 | 2/2000 |
| WO | WO 00/61557 A1 | 10/2000 |
| WO | WO 00/61558 A1 | 10/2000 |
| WO | WO 02/22572 A2 | 3/2002 |
| WO | WO 02/096875 A1 | 12/2002 |

OTHER PUBLICATIONS

Bruno S. Huegi et al.; "Synthesis and Pharmacological Studies of 4,4-Disubstituted Piperidines: A New Class of Compoundswith Potent Analgesic Properties"; J. Med. Chem.; 1983; vol. 26; pp. 42-50.

*Primary Examiner*—Taofiq A Solola
(74) *Attorney, Agent, or Firm*—Oliff & Berridge, PLC

(57) ABSTRACT

An agent for preventing/treating respiratory diseases contains, as an active ingredient, a compound represented by following Formula (I):

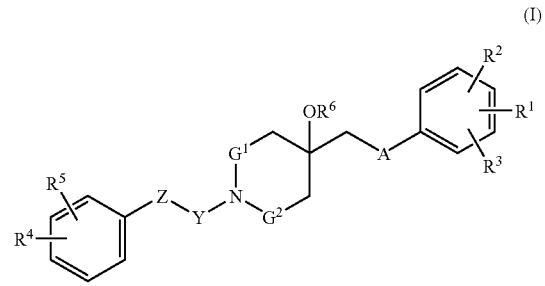

wherein A is a group represented by L-W [wherein L is a bond or $CH_2$; and W is O, $SO_n$ (wherein n is 0 to 2), or $-NR^7-$ (wherein $R^7$ is hydrogen or lower alkyl)]; each of $G^1$ and $G^2$ is $(CH_2)r$ (wherein r is 0 to 2), provided that when n is 1, $G^1$ and $G^2$ may be bridged by lower alkylene; Y is a lower alkylene or (substituted) benzylidene; Z is a bond or O, provided that when Z is a bond, Y may form a 5- or 6-membered ring with carbon on the benzene ring; $R^1$ is, for example, $NO_2$, a lower alkoxycarbonyl, (substituted) carbamoyl, (protected) hydroxyl group, (protected) carboxyl, or (protected) N-hydroxycarbamoyl; each of $R^2$ and $R^3$ is hydrogen, halogen, (halogenated) lower alkyl, (halogenated) lower alkoxy or $NO_2$; each of $R^4$ and $R^5$ is, for example, hydrogen, halogen, (halogenated) lower alkyl, (halogenated) lower alkoxy, CN, or lower alkylsulfonyl; and $R^6$ is hydrogen or lower alkyl, a salt thereof or a solvate of them. It has excellent antitussive activity when used as an agent for preventing/treating respiratory diseases such as lung cancer, common cold syndrome, pulmonary tuberculosis, pneumonia, acute bronchitis or chronic bronchitis.

13 Claims, No Drawings

AGENT FOR TREATING RESPIRATORY DISEASES CONTAINING 4-HYDROXYPIPERIDINE DERIVATIVE AS ACTIVE INGREDIENT

TECHNICAL FIELD

The present invention relates to agents for preventing and/or treating respiratory diseases, and especially to antitussive agents, which contain 4-hydroxypiperidine derivatives or the pharmaceutically acceptable salts thereof as active ingredients. This invention also relates to novel 4-hydroxypiperidine derivatives or the salts thereof and the methods for producing them. In addition, this invention relates to the pharmaceutical compositions containing at least one of the derivatives as active ingredients, more specifically, it relates to agents for treating respiratory diseases, and to antitussive agents.

BACKGROUND ART

The respiratory apparatus is the generic term for organs and tissues related to respiration, and it plays important roles in life support such as the intake of atmospheric oxygen and the excretion of carbon dioxide generated as a result of metabolism.

Representative respiratory diseases with the cough include, for example, lung cancer, carcinomatous lymphopathy, rib fracture, spontaneous pneumothorax, cold syndrome (upper respiratory infection), pulmonary tuberculosis, interstitial pneumonitis, pleurisy, pneumonia, acute bronchitis, chronic bronchitis, pulmonary emphysema, pneumoconiosis, bronchiectasis, diffuse panbronchiolitis, bronchial asthma, pulmonary embolism, and pulmonary infarction.

Cough is occurred as follows. The lungs enlarge as a result of deep inspiration, and the pressure in the lungs increases due to strong contraction of the respiratory muscles. The muscles of larynx suddenly relax, and thereby the air is rapidly exhaled with secreted materials to the respiratory tract. When secreted materials or foreign substances accumulate on the mucous membranes of the respiratory tract and/or there are abnormalities in the pleura, lungs, or diaphragma, their impulses stimulate the cough center in the posterolateral medulla oblongata and causes the attack of coughing ("Saishin Yakurigaku (in Japanese, Modern Pharmacology)", 10.3 Antitussive Agent, Sumiko Fujino, 1990, Kodansha Ltd.).

Cough is mainly caused by excessive secretion from the mucous membranes of respiratory tract, by chemical stimuli such as smoke and gas, by foreign substances, by inflammation of respiratory tract, by allergic reactions, by the compression of bronchi by tumor in the thoracic cavity, or by psychogenic factors. The worsening and chronicity of cough consumes energy of the respiratory muscles and physical strength to thereby prevent recovery of the underlying disease.

Antitussive agents are classified as centrally-acting antitussive agents which block the cough center and peripherally-acting antitussive agents which reduce the stimuli to peripheral receptors. The centrally-acting antitussive agents typified by codeine phosphate generally are very effective but induce adverse actions such as respiratory depression, constipation, nausea, emesis, headache, sleepiness, and eruption. The repeated use of them also induces tolerance and/or addiction. The peripherally-acting antitussive agents typified by methylephedrine exhibit only mild antitussive actions. Recently, the opioid delta ($\delta$) receptor antagonists have been developed as antitussive agents. However, because the $\delta$ receptor is deeply involved in mental and emotional behaviors, these antagonists should induce adverse actions (Nat. Genet. 25, 2, 195, 2000). Accordingly, demands have been made on antitussive agents having higher efficacy and less adverse actions.

Huegi et al. have reported 4-hydroxypiperidine derivatives showing analgesic actions (J. Med. Chem. 26, 42, 1983). These compounds, however, are morphine-like centrally-acting analgesic agents having affinity for opiate receptors and differ in structure from the compounds of the present invention. PCT International Publication No. WO 00/61557 has disclosed 4-hydroxypiperidine derivatives having antiarrhythmic actions. In addition, PCT International Publication No. WO 00/61558 has disclosed 4-hydroxypiperidine derivatives which are useful as agents for treating neuropathic pain. These compounds act upon sodium channels and selectively prevent persistent sodium currents more than transient sodium currents. However, these compounds differ in structure from the compounds of the present invention.

Japanese Patent Application Laid-open No. Sho 60-163861 has disclosed 4-(phenoxymethyl)piperidin-4-ol derivatives containing aryloxymethylpiperidinol derivatives having antidepressive, antiarrhythmic or antihypertensive actions. However, it has lacked the disclosure about antitussive actions. These compounds also differ in structure from the compounds of the present invention. PCT International Publication No. WO 93/02052 has disclosed 2-(4-hydroxypiperidino)-1-alkanol derivatives as anti-ischemic agents. However, it has lacked the disclosure about antitussive actions. These compounds differ in basic structure from the compounds of the present invention.

Piperidine derivatives having antitussive actions have been disclosed as nociceptin receptor agonists in PCT international publication No. WO00/06545 but they have different structures from those of the compounds of the present invention.

PCT International Publication No. WO 00/06544 has described cyclic amine derivatives (piperidine derivatives) with the tachykinin-antagonistic action. These derivatives can be useful for the treatment of asthma, cough, or pain related to tachykinin. These derivatives, however, are different in structure from the compounds of the present invention which have specific substituents.

PCT International Publication No. WO 02/22572 has disclosed 3-substituted azetidine derivatives, 3-substituted pyrrolidine derivatives or 3-substituted piperidine derivatives. They have a modulating actions on dopamine, serotonin or norepinephrine receptors, or their transporters. These derivatives are useful for the treatment of anxiety, depression, erectile dysfunction, Alzheimer disease, mental disorder, urinary incontinence, and/or neuropathic pain. The publication, however, has lacked the disclosure about antitussive actions.

Drugs to be developed must be required to have not only high pharmacological activities but also high safety over long time. They also must achieve the rigid criteria in, for example, absorption, distribution, metabolism, and secretion. They must satisfy various requirements in, for example, drug interaction, desensitization or tolerance, gastrointestinal absorption, transition rate, absorption rate and first pass effect, organ barrier, protein binding, the induction of drug metabolic enzymes, excretion route and clearance, and application method (application site, method, and object). It is very difficult to satisfy these requirements. Thus, new drugs must have a wider safety range and more excellent pharmacokinetic properties.

These general requirements in the development of drugs are applied to agents for treating respiratory diseases. In addition, the agents for treating respiratory diseases typified by antitussive agents must have less adverse actions and higher efficacy than conventional equivalents such as the conventional centrally-acting antitussive agents, peripherally-acting antitussive agents, and the δ opioid receptor antagonists.

DISCLOSURE OF INVENTION

An object of the present invention is to provide novel compounds that have potent antitussive actions and less adverse actions. Another object of the present invention is to provide the methods for producing the compounds, the drugs, and the pharmaceutical composition containing them. Specifically, it is to provide agents for preventing and/or treating respiratory diseases, such as antitussive agents, which solve at least one of these problems in conventional equivalents and is capable of being administered to mammalians including human beings. Such problems of conventional equivalents contain adverse actions such as respiratory depression, constipation, nausea, emesis, headache, sleepiness, and eruption. They also contain tolerance and/or addiction by repeated use of the centrally-acting antitussive agents. Furthermore, they contain adverse actions related to mental and emotional behaviors which would be induced by the selective δ opioid receptor.

After intensive investigations to achieve the above problems and to provide the agents with potent antitussive actions and high safety, the present inventors have found that 4-hydroxypiperidine derivatives and the salts thereof inhibit citric acid-induced cough in guinea pigs and have less adverse actions. The present invention has been achieved based on these findings.

Specifically, the present invention provides, as a first embodiment, an agent for preventing and/or treating respiratory diseases, containing, as an active ingredient, a compound represented by following Formula (I):

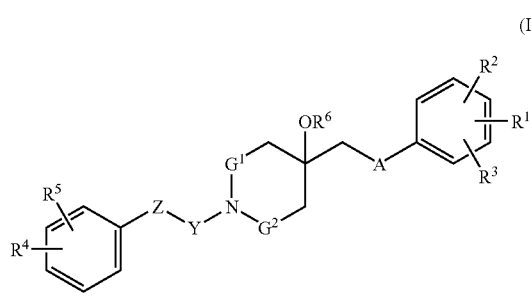

(I)

wherein A represents a group represented by L-W (wherein L represents a bond or methylene group; and W represents oxygen atom, a group represented by SOn (wherein n denotes an integer of 0 to 2) or a group represented by —NR$^7$— (wherein R$^7$ represents hydrogen atom or a lower alkyl group)); each of G$^1$ and G$^2$ independently represents (CH$_2$)r (wherein r denotes an integer of 0 to 2), wherein G$^1$ and G$^2$ may further be bridged by a lower alkylene group when both of "r"s in G$^1$ and G$^2$ are 1; Y represents a lower alkylene group, or benzylidene group unsubstituted or substituted by R$^4$; Z represents a bond or oxygen atom, wherein Y may form a 5- or 6-membered ring with carbon atoms on the benzene ring when Z represents a bond; R$^1$ represents nitro group, a lower alkoxycarbonyl group, carbamoyl group unsubstituted or mono- or di-substituted by lower alkyl groups, unprotected or protected hydroxyl group, unprotected or protected carboxyl group, unprotected or protected N-hydroxycarbamoyl group, a lower alkyl group substituted by unprotected or protected hydroxyl group, a lower alkyl group substituted by unprotected or protected carboxyl group, or tetrazolyl group; each of R$^2$ and R$^3$ independently represents hydrogen atom, a halogen atom, a lower alkyl group unsubstituted or substituted by one or more halogen atoms, a lower alkoxy group unsubstituted or substituted by one or more halogen atoms, or nitro group; each of R$^4$ and R$^5$ independently represents a hydrogen atom, a halogen atom, a lower alkyl group unsubstituted or substituted by one or more halogen atoms, a lower alkoxy group unsubstituted or substituted by one or more halogen atoms, cyano group, or a lower alkylsulfonyl group; and R$^6$ represents hydrogen atom or a lower alkyl group, provided that it is excluded that R$^1$ is nitro group or unprotected or protected hydroxyl group when W is a group represented by SOn (wherein n denotes an integer of 0 to 2), a pharmaceutically acceptable salt thereof or a solvate of them.

For the compound represented by Formula (I) as the first embodiment, preferred substituents and their preferred combinations will be introduced below, but the present invention should not be limited to those examples.

R$^1$ is preferably nitro group, a lower alkoxycarbonyl group, carbamoyl group unsubstituted or mono- or di-substituted by lower alkyl groups, unprotected or protected carboxyl group, or tetrazolyl group, and is more preferably carboxyl group.

R$^1$ is substituted at the ortho-, meta- or para-position with respect to carbon atom to which A bonds, preferably substituted at the para-position (the 4-position).

As R$^1$, carboxyl group substituted at the para-position of A is more preferable.

R$^4$ is preferably cyano group.

R$^4$ is substituted at the ortho-, meta- or para-position with respect to carbon atom to which Z bonds, preferably substituted at the para-position.

R$^4$ is more preferably cyano group substituted at the para-position.

W is preferably a group represented by —NR$^7$

R$^7$ is preferably a lower alkyl group and is more preferably methyl group or ethyl group.

Each of n in G$^1$ and G$^2$ is preferably 0 or 1.

The present invention provides, as a second embodiment, an antitussive agent containing the compound represented by Formula (I), a pharmaceutically acceptable salt thereof or a solvate of them as an active ingredient.

As a third embodiment, the present invention provides an agent for improving nonproductive cough, which contains the compound represented by Formula (I), a pharmaceutically acceptable salt thereof or a solvate of them as an active ingredient.

Preferred substituents and their preferred combinations in the compound represented by Formula (I) in the second and third embodiments are the same as in the first embodiment.

The present invention further provides, as a fourth embodiment, a compound represented by following Formula (II):

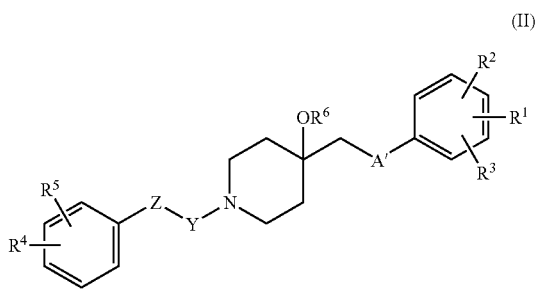

(II)

wherein A' represents a group represented by L-W' (wherein L represents a bond or methylene group; and W' represents oxygen atom or a group represented by —NR$^7$— (wherein R$^7$ represents hydrogen atom or a lower alkyl group)); Y represents a lower alkylene group, or benzylidene group unsubstituted or substituted by R$^4$; Z represents a bond or oxygen atom, wherein Y may form a 5- or 6-membered ring with carbon atoms on the benzene ring when Z represents a bond; R$^1$ represents nitro group, a lower alkoxycarbonyl group, carbamoyl group unsubstituted or mono- or di-substituted by lower alkyl groups, unprotected or protected hydroxyl group, unprotected or protected carboxyl group, unprotected or protected N-hydroxycarbamoyl group, a lower alkyl group substituted by unprotected or protected hydroxyl group, a lower alkyl group substituted by unprotected or protected carboxyl group, or tetrazolyl group; each of R$^2$ and R$^3$ independently represents hydrogen atom, a halogen atom, a lower alkyl group unsubstituted or substituted by one or more halogen atoms, a lower alkoxy group unsubstituted or substituted by one or more halogen atoms, or nitro group; each of R$^4$ and R$^5$ independently represents hydrogen atom, a halogen atom, a lower alkyl group unsubstituted or substituted by one or more halogen atoms, a lower alkoxy group unsubstituted or substituted by one or more halogen atoms, cyano group, or a lower alkylsulfonyl group; and R$^6$ represents hydrogen atom or a lower alkyl group, provided that R$^1$ is limited to unprotected or protected N-hydroxycarbamoyl group or a lower alkyl group substituted by unprotected or protected carboxyl group when R$^2$ and R$^3$ are both hydrogen atoms, or provided that it is excluded that R$^1$ is unprotected or protected hydroxyl group or a lower alkyl group substituted by unprotected or protected hydroxyl group when W' is a group represented by —NR$^7$—, a salt thereof or a solvate of them.

For the compound represented by Formula (II) as the fourth embodiment, preferred substituents and their preferred combinations will be introduced below, but the present invention should not be limited to those examples.

R$^1$ is preferably nitro group, a lower alkoxycarbonyl group, carbamoyl group unsubstituted or mono- or di-substituted by lower alkyl groups, unprotected or protected carboxyl group, or tetrazolyl group, and is more preferably carboxyl group.

R$^1$ is substituted at the ortho-, meta- or para-position with respect to carbon atom to which A' bonds, preferably substituted at the para-position (the 4-position).

As R$^1$, carboxyl group substituted at the para-position of A' is more preferable.

R$^4$ is preferably cyano group.

R$^4$ is substituted at the ortho-, meta- or para-position with respect to carbon atom to which Z bonds, preferably substituted at the para-position.

R$^4$ is more preferably cyano group substituted at the para-position.

W' is preferably a group represented by —NR$^7$—.

R$^7$ is preferably a lower alkyl group and is more preferably methyl group or ethyl group.

The present invention provides, as a fifth embodiment, an agent for preventing and/or treating respiratory diseases, which contains the compound represented by Formula (II), a pharmaceutically acceptable salt thereof or a solvate of them as an active ingredient.

The present invention also provides, as a sixth embodiment, an antitussive agent containing the compound represented by Formula (II), a pharmaceutically acceptable salt thereof or a solvate of them as an active ingredient.

The present invention further provides, as a seventh embodiment, an agent for improving nonproductive cough, which contains the compound represented by Formula (II), a pharmaceutically acceptable salt thereof or a solvate of them as an active ingredient.

Preferred substituents and preferred combinations of them in the compound represented by Formula (II) in the fifth, sixth, and seventh embodiments are the same as those in the fourth embodiment.

In addition, the present invention provides, as an eighth aspect, a compound represented by following Formula (III):

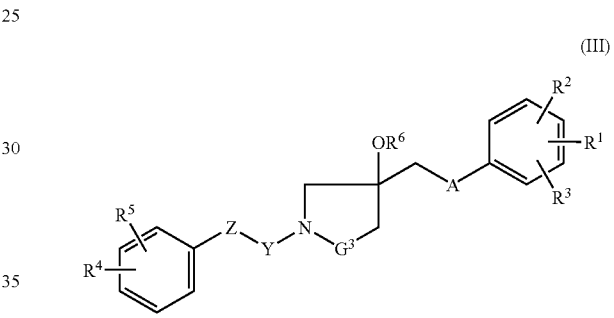

(III)

wherein A represents a group represented by L-W (wherein L represents a bond or methylene group; and W represents oxygen atom, a group represented by SOn (wherein n denotes an integer of 0 to 2) or a group represented by —NR$^7$— (wherein R$^7$ represents hydrogen atom or a lower alkyl group)); G$^3$ represents (CH$_2$)m (wherein m denotes 0 or 1); Y represents a lower alkylene group, or benzylidene group unsubstituted or substituted by R$^4$; Z represents a bond or oxygen atom, wherein Y may form a 5- or 6-membered ring with carbon atoms on the benzene ring when Z represents a bond; R$^1$ represents nitro group, a lower alkoxycarbonyl group, carbamoyl group unsubstituted or mono- or di-substituted by lower alkyl groups, unprotected or protected hydroxyl group, unprotected or protected carboxyl group, unprotected or protected N-hydroxycarbamoyl group, a lower alkyl group substituted by unprotected or protected hydroxyl group, a lower alkyl group substituted by unprotected or protected carboxyl group, or tetrazolyl group; each of R$^2$ and R$^3$ independently represents hydrogen atom, a halogen atom, a lower alkyl group unsubstituted or substituted by one or more halogen atoms, a lower alkoxy group unsubstituted or substituted by one ore more halogen atoms, or nitro group; each of R$^4$ and R$^5$ independently represents hydrogen atom, a halogen atom, a lower alkyl group unsubstituted or substituted by one or more halogen atoms, a lower alkoxy group unsubstituted or substituted by one or more halogen atoms, cyano group, or a lower alkylsulfonyl group; and R$^6$ represents hydrogen atom or a lower alkyl group, a salt thereof or a solvate of them.

For the compound represented by Formula (III) as the eighth embodiment, preferred substituents and their preferred combinations will be introduced below, but the present invention should not be limited to those examples.

$R^1$ is preferably nitro group, a lower alkoxycarbonyl group, carbamoyl group unsubstituted or mono- or di-substituted by lower alkyl groups, unprotected or protected carboxyl group, or tetrazolyl group, and is more preferably carboxyl group.

$R^1$ is substituted at the ortho-, meta- or para-position with respect to carbon atom to which A bonds, preferably substituted at the para-position (the 4-position).

As $R^1$, carboxyl group substituted at the para-position of A is more preferable.

$R^4$ is preferably cyano group.

$R^4$ is substituted at the ortho-, meta- or para-position with respect to carbon atom to which Z bonds, preferably substituted at the para-position.

$R^4$ is more preferably cyano group substituted at the para-position.

W is preferably a group represented by —$NR^7$—.

$R^7$ is preferably a lower alkyl group and is more preferably methyl group or ethyl group.

The repetition number m in $G^3$ is preferably 0.

The present invention provides, as a ninth embodiment, an agent for preventing and/or treating respiratory diseases, which contains the compound represented by Formula (III), a pharmaceutically acceptable salt thereof or a solvate of them as an active ingredient.

The present invention also provides, as a tenth embodiment, an antitussive agent containing the compound represented by Formula (III), a pharmaceutically acceptable salt thereof or a solvate of them as an active ingredient.

The present invention also provides, as an eleventh embodiment, an agent for improving nonproductive cough, which contains the compound represented by Formula (III), a pharmaceutically acceptable salt thereof or a solvate of them as an active ingredient.

Preferred substituents and preferred combinations of them in the compounds represented by Formula (III) in the ninth, tenth and eleventh embodiments are the same as those in the eighth embodiment.

The present invention provides, as a twelfth embodiment, a compound represented by following Formula (IV):

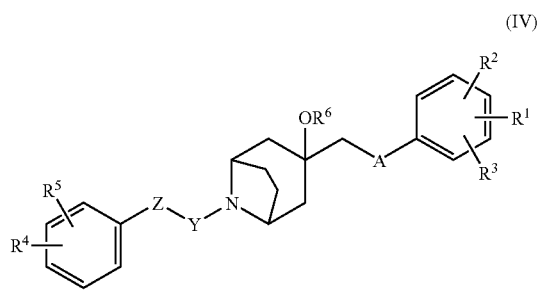

(IV)

wherein A represents a group represented by L-W (wherein L represents a bond or methylene group; and W represents oxygen atom, a group represented by SOn (wherein n denotes an integer of 0 to 2) or a group represented by —$NR^7$— (wherein $R^7$ represents hydrogen atom or a lower alkyl group)); Y represents a lower alkylene group, or benzylidene group unsubstituted or substituted by $R^4$; Z represents a bond or oxygen atom, wherein Y may form a 5- or 6-membered ring with carbon atoms on the benzene ring when Z represents a bond; $R^1$ represents nitro group, a lower alkoxycarbonyl group, carbamoyl group unsubstituted or mono- or di-substituted by lower alkyl groups, unprotected or protected hydroxyl group, unprotected or protected carboxyl group, unprotected or protected N-hydroxycarbamoyl group, a lower alkyl group substituted by unprotected or protected hydroxyl group, a lower alkyl group substituted by unprotected or protected carboxyl group, or tetrazolyl group; each of $R^2$ and $R^3$ independently represents hydrogen atom, a halogen atom, a lower alkyl group unsubstituted or substituted by one or more halogen atoms, a lower alkoxy group unsubstituted or substituted by one or more halogen atoms, or nitro group; each of $R^4$ and $R^5$ independently represents hydrogen atom, a halogen atom, a lower alkyl group unsubstituted or substituted by one or more halogen atoms, a lower alkoxy group unsubstituted or substituted by one or more halogen atoms, cyano group, or a lower alkylsulfonyl group; and $R^6$ represents hydrogen atom or a lower alkyl group, a salt thereof or a solvate of them.

For the compound represented by Formula (IV) as the twelfth embodiment, preferred substituents and their preferred combinations will be introduced below, but the present invention should not be limited to those examples.

$R^1$ is preferably nitro group, a lower alkoxycarbonyl group, carbamoyl group unsubstituted or mono- or di-substituted by lower alkyl groups, unprotected or protected carboxyl group, or tetrazolyl group, and is more preferably carboxyl group.

$R^1$ is substituted at the ortho-, meta- or para-position with respect to carbon atom to which A bonds, preferably substituted at the para-position (the 4-position).

As $R^1$, carboxyl group substituted at the para-position of A is more preferable.

$R^4$ is preferably cyano group.

$R^4$ is substituted at the ortho-, meta- or para-position with respect to carbon atom to which Z bonds, preferably substituted at the para-position.

$R^4$ is more preferably cyano group substituted at the para-position.

W is preferably a group represented by —$NR^7$—.

$R^7$ is preferably a lower alkyl group and is more preferably methyl group or ethyl group.

The present invention provides, as a thirteenth embodiment, an agent for preventing and/or treating respiratory diseases, which contains the compound represented by Formula (IV), a pharmaceutically acceptable salt thereof or a solvate of them as an active ingredient.

The present invention also provides, as a fourteenth embodiment, an antitussive agent containing the compound represented by Formula (IV), a pharmaceutically acceptable salt thereof or a solvate of them as an active ingredient.

The present invention also provides, as a fifteenth embodiment, an agent for improving nonproductive cough, which contains the compound represented by Formula (IV), a pharmaceutically acceptable salt thereof or a solvate of them as an active ingredient.

Preferred substituents and preferred combinations of them in the compounds represented by Formula (IV) in the thirteenth, fourteenth and fifteenth embodiments are the same as those in the twelfth embodiment.

The present invention further provides, as a sixteenth embodiment, a method for producing a compound represented by following Formula (I):

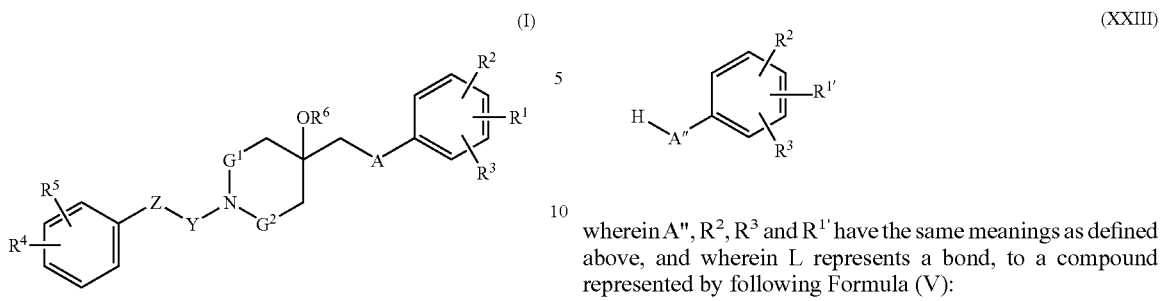

wherein A, G¹, G², Y, Z, R¹, R², R³, R⁴, R⁵ and R⁶ have the same meanings as defined above, or a salt thereof, including one of following Processes (a), (b), (c), (d), (e), (f), (g) and (h).

Process (a) including the steps of:
adding a compound represented by following Formula (XXIII):

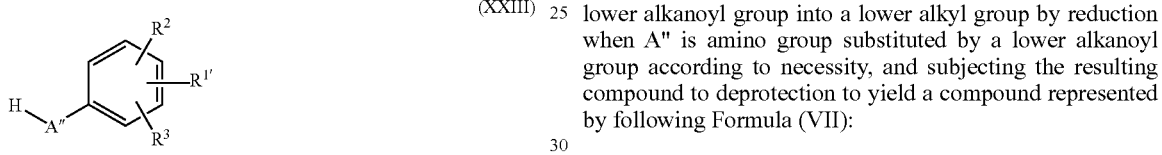

wherein R² and R³ have the same meanings as defined above; A" represents a group represented by L-W" (wherein L represents a bond or methylene group; and W" represents oxygen atom, a group represented by SOn (wherein n denotes an integer of 0 to 2) or a group represented by —NR⁷'— (wherein R⁷' represents hydrogen atom, a lower alkyl group or a lower alkanoyl group)); R¹' represents nitro group, a lower alkoxycarbonyl group, carbamoyl group unsubstituted or mono- or di-substituted by lower alkyl groups, unprotected or protected hydroxyl group, unprotected or protected carboxyl group, unprotected or protected N-hydroxycarbamoyl group, a lower alkyl group substituted by unprotected or protected hydroxyl group, tetrazolyl group, cyano group, or formyl group, and wherein L represents a bond, to a compound represented by following Formula (XXIV):

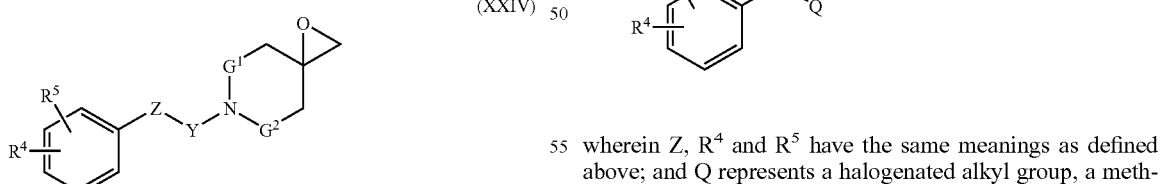

wherein G¹, G², Y, Z, R⁴ and R⁵ have the same meanings as defined above, and then converting a lower alkanoyl group into a lower alkyl group by reduction when A" is amino group substituted by a lower alkanoyl group, and converting R¹' into R¹ according to necessity;

Process (b) including the steps of:
adding a compound represented by following Formula (XXIII):

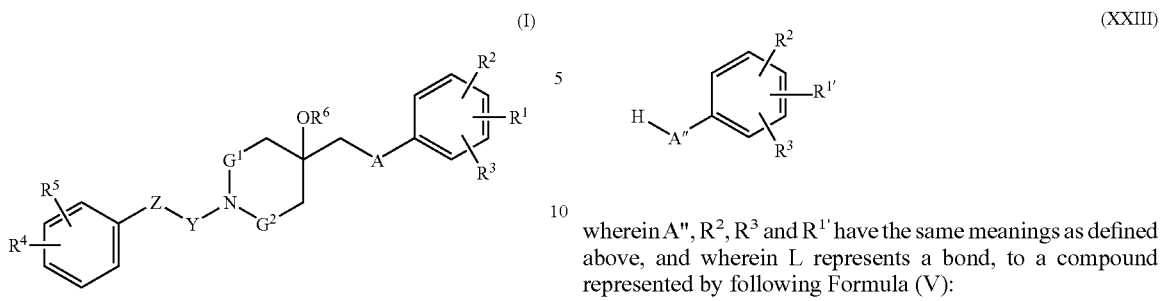

wherein A", R², R³ and R¹' have the same meanings as defined above, and wherein L represents a bond, to a compound represented by following Formula (V):

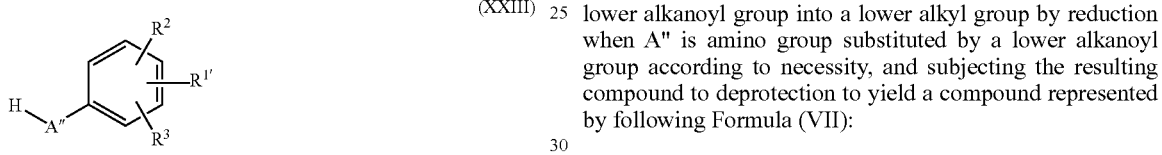

wherein G¹ and G² have the same meanings as defined above; and P represents an amino-protecting group, converting a lower alkanoyl group into a lower alkyl group by reduction when A" is amino group substituted by a lower alkanoyl group according to necessity, and subjecting the resulting compound to deprotection to yield a compound represented by following Formula (VII):

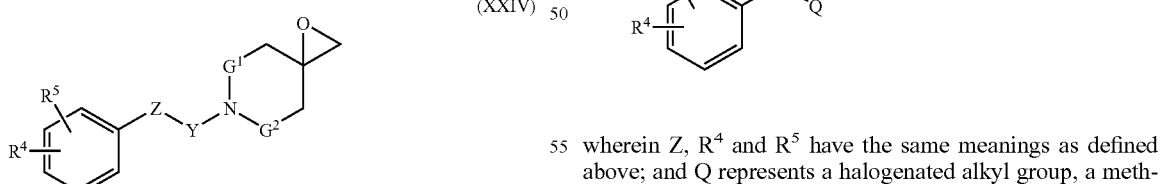

wherein A", G¹, G², R², R³, R⁶ and R¹' have the same meanings as defined above, subjecting the compound represented by Formula (VII) to a reaction with a compound represented by following Formula (VIII):

(VIII)

wherein Z, R⁴ and R⁵ have the same meanings as defined above; and Q represents a halogenated alkyl group, a methanesulfonyloxyalkyl group or an arylsulfonyloxyalkyl group such as p-toluenesulfonyloxyalkyl group and so on, each of which may be substituted by phenyl group unsubstituted or substituted by R⁴, formyl group, benzoyl group unsubstituted or substituted by R⁴, a formylalkyl group, a benzoylalkyl group unsubstituted or substituted by R⁴ on its benzene ring, carboxyl group or a carboxyalkyl group; or when Z is a bond, Q represents a halogenated alkylene group or oxoalkylene group which forms 5- or 6-membered ring with carbon atom on the benzene ring, provided that the reaction is carried out in the presence or absence of a base when Q represents a halogenated alkyl group, a methanesulfonyloxyalkyl group or an arylsulfonyloxyalkyl group, each of which may be substituted by phenyl group unsubstituted or substituted by $R^4$, or when Z is a bond and Q represents a halogenated alkylene group which forms a 5- or 6-membered ring with carbon atom on the benzene ring, provided that the reaction is carried out under reducing conditions in the presence or absence of an acid catalyst when Q represents formyl group, benzoyl group unsubstituted or substituted by $R^4$, a formylalkyl group or a benzoylalkyl group unsubstituted or substituted by $R^4$ on its benzene ring, or when Z is a bond and Q represents an oxoalkylene group which forms a 5- or 6-membered ring with carbon atom on the benzene ring, or provided that the reaction is carried out with the use of a condensing agent, followed by reduction, when Q represents carboxyl group or a carboxyalkyl group, and converting $R^{1'}$ of the resulting compound into $R^1$ according to necessity;

Process (c) including the steps of:

allowing a compound represented by following Formula (IX):

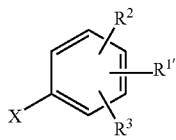

(IX)

wherein $R^{1'}$, $R^2$ and $R^3$ have the same meanings as defined above; and X represents a halogen atom such as F, to react with a compound represented by following Formula (X):

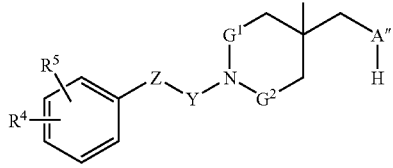

(X)

wherein $G^1$, $G^2$, Y, Z, $R^4$, $R^5$, $R^6$ and A" have the same meanings as defined above; and then convert a lower alkanoyl group into a lower alkyl group by reduction when A" is amino group substituted by a lower alkanoyl group, and converting $R^{1'}$ of the resulting compound into $R^1$ according to necessity;

Process (d) including the steps of:

allowing a compound represented by following Formula (IX):

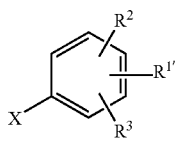

(IX)

wherein X, $R^2$, $R^3$ and $R^{1'}$ have the same meanings as defined above, to react with a compound represented by following Formula (XI):

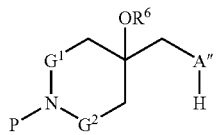

(XI)

wherein A", $G^1$, $G^2$, P and $R^6$ have the same meanings as defined above, subjecting the resulting compound to deprotection to yield a compound represented by following Formula (VII):

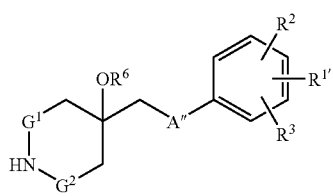

(VII)

wherein A", $G^1$, $G^2$, $R^2$, $R^3$, $R^6$ and $R^{1'}$ have the same meanings as defined above, subjecting the compound represented by Formula (VII) to a reaction with a compound represented by following Formula (VIII):

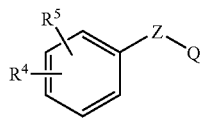

(VIII)

wherein Q, Z, $R^4$ and $R^5$ have the same meanings as defined above, provided that the reaction is carried out in the presence or absence of a base when Q represents a halogenated alkyl group, a methanesulfonyloxyalkyl group or an arylsulfonyloxyalkyl group, each of which may be substituted by phenyl group unsubstituted or substituted by $R^4$, or when Z is a bond and Q represents a halogenated alkylene group which forms a 5- or 6-membered ring with carbon atoms on the benzene ring, provided that the reaction is carried out under reducing conditions in the presence or absence of an acid catalyst when Q represents formyl group, benzoyl group unsubstituted or substituted by $R^4$, a formylalkyl group or a benzoylalkyl group unsubstituted or substituted by $R^4$ on its benzene ring, or when Z is a bond and Q represents an oxoalkylene group which forms a 5- or 6-membered ring with carbon atoms on the benzene ring, or provided that the reaction is carried out with the use of a condensing agent, followed by reduction, when Q represents carboxyl group or a carboxyalkyl group, and converting $R^{1'}$ of the resulting compound into $R^1$ according to necessity;

Process (e) including the steps of:

allowing a compound represented by following Formula (XII):

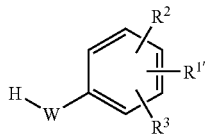

(XII)

wherein $R^2$, $R^3$, $R^{1'}$ and W have the same meanings as defined above, to react with a compound represented by following Formula (XIII):

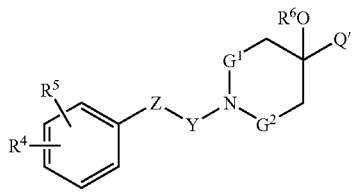

(XIII)

wherein $G^1$, $G^2$, Y, Z, $R^4$, $R^5$ and $R^6$ have the same meanings as defined above; and Q' represents a halogenated alkyl group, a methanesulfonyloxyalkyl group, an arylsulfonyloxyalkyl group such as a p-toluenesulfonyloxyalkyl group, formyl group, a formylalkyl group, carboxyl group or a carboxyalkyl group, and converting $R^{1'}$ of the resulting compound into $R^1$ according to necessity;

Process (f) including the steps of:
allowing a compound represented by following Formula (XII):

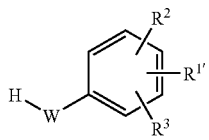

(XII)

wherein $R^2$, $R^3$, $R^{1'}$ and W have the same meanings as defined above, to react with a compound represented by following Formula (XIV):

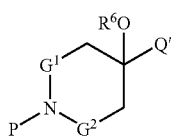

(XIV)

wherein $G^1$, $G^2$, P, Q' and $R^6$ have the same meanings as defined above, subjecting the resulting compound to deprotection to yield a compound represented by following Formula (XVI):

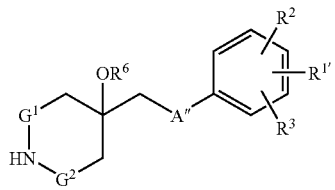

(XVI)

wherein A", $G^1$, $G^2$, $R^2$, $R^3$, $R^6$ and $R^{1'}$ have the same meanings as defined above, subjecting the compound represented by Formula (XVI) to a reaction with a compound represented by following Formula (VIII):

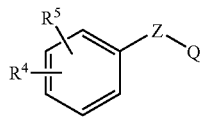

(VIII)

wherein Q, Z, $R^4$ and $R^5$ have the same meanings as defined above, provided that the reaction is carried out in the presence or absence of a base when Q represents a halogenated alkyl group, a methanesulfonyloxyalkyl group or an arylsulfonyloxyalkyl group, each of which may be substituted by phenyl group unsubstituted or substituted by $R^4$, or when Z is a bond and Q represents a halogenated alkylene group which forms a 5- or 6-membered ring with carbon atoms on the benzene ring, provided that the reaction is carried out under reducing conditions in the presence or absence of an acid catalyst when Q represents formyl group, benzoyl group unsubstituted or substituted by $R^4$, a formylalkyl group or a benzoylalkyl group unsubstituted or substituted by $R^4$ on its benzene ring, or when Z is a bond and Q represents an oxoalkylene group which forms a 5- or 6-membered ring with carbon atom on the benzene ring, or provided that the reaction is carried out with the use of a condensing agent, followed by reduction, when Q represents carboxyl group or a carboxyalkyl group, and converting $R^1$ of the resulting compound into $R^1$ according to necessity;

Process (g) including the steps of:
allowing a compound represented by following Formula (XVII):

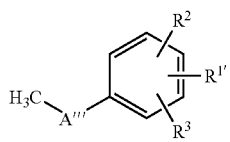

(XVII)

wherein $R^2$, $R^3$ and $R^{1'}$ have the same meanings as defined above; and A''' represents a group represented by SOn (wherein n denotes an integer of 0 to 2) or a group represented by —(C=O)NR$^7$— (wherein $R^7$ represents hydrogen atom or a lower alkyl group), to react with a compound represented by following Formula (XVIII):

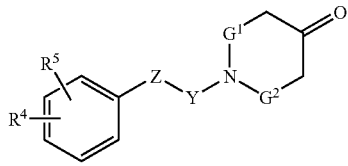

wherein $G^1$, $G^2$, Y, Z, $R^4$ and $R^5$ have the same meanings as defined above; and then converting $R^{1'}$ of the resulting compound into $R^1$ according to necessity; and Process (h) including the steps of:

allowing a compound represented by the following Formula (XVII):

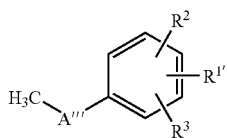

wherein $A'''$, $R^2$, $R^3$ and $R^{1'}$ have the same meanings as defined above, to react with a compound represented by following Formula (XIX):

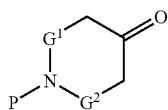

wherein $G^1$, $G^2$ and P have the same meanings as defined above, subjecting the resulting compound to deprotection to yield a compound represented by following Formula (XXI):

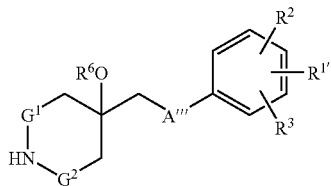

wherein $A'''$, $G^1$, $G^2$, $R^2$, $R^3$, $R^6$ and $R^{1'}$ have the same meanings as defined above, subjecting the compound represented by Formula (XXI) to a reaction with a compound represented by following Formula (VIII):

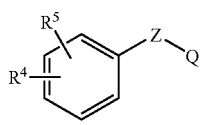

wherein Q, Z, $R^4$ and $R^5$ have the same meanings as defined above, provided that the reaction is carried out in the presence or absence of a base when Q represents a halogenated alkyl group, a methanesulfonyloxyalkyl group or an arylsulfonyloxyalkyl group, each of which may be substituted by phenyl group unsubstituted or substituted by $R^4$, or when Z is a bond and Q represents a halogenated alkylene group which forms a 5- or 6-membered ring with carbon atoms on the benzene ring, provided that the reaction is carried out under reducing conditions in the presence or absence of an acid catalyst when Q represents formyl group, benzoyl group unsubstituted or substituted by $R^4$, a formylalkyl group or a benzoylalkyl group unsubstituted or substituted by $R^4$ on its benzene ring, or when Z is a bond and Q represents an oxoalkylene group which forms a 5- or 6-membered ring with carbon atoms on the benzene ring, or provided that the reaction is carried out with the use of a condensing agent, followed by reduction, when Q represents carboxyl group or a carboxyalkyl group, and converting $R^{1'}$ of the resulting compound into $R^1$ according to necessity.

BEST MODE FOR CARRYING OUT THE INVENTION

The present invention will be illustrated in detail below.

The groups described in the formula in the present invention are defined as follows.

The "lower" means a straight, branched or cyclic carbon chain containing one to four carbon atoms unless otherwise stated, and can be expressed as "C1-4." Accordingly, the "lower alkyl group" includes, for example, a methyl group, ethyl group, propyl group, isopropyl group, cyclopropyl group, butyl group, isobutyl group, sec-butyl group, tert-butyl group and cyclobutyl group.

The "lower alkoxycarbonyl group" means C1-4 alkoxycarbonyl group having one to four carbon atoms in the alkoxy moiety and includes, for example, methoxycarbonyl group, ethoxycarbonyl group, propoxycarbonyl group, isopropoxycarbonyl group, cyclopropyloxycarbonyl group, butoxycarbonyl group, isobutoxycarbonyl group, sec-butoxycarbonyl group, tert-butoxycarbonyl group and cyclobutyloxycarbonyl group.

The "carbamoyl group unsubstituted or mono- or di-substituted by lower alkyl groups" means carbamoyl group of which one or two hydrogen atoms bound on nitrogen atom may be substituted by the above-mentioned "lower alkyl group." Specific examples thereof are carbamoyl group, methylcarbamoyl group, ethylcarbamoyl group, propylcarbamoyl group, isopropylcarbamoyl group, cyclopropylcarbamoyl group, butylcarbamoyl group, isobutylcarbamoyl group, sec-butylcarbamoyl group, tert-butylcarbamoyl group, cyclobutylcarbamoyl group, dimethylcarbamoyl group, diethylcarbamoyl group, dipropylcarbamoyl group, diisopropylcarbamoyl group, dicyclopropylcarbamoyl group, dibutylcarbamoyl group, diisobutylcarbamoyl group, di-sec-butylcarbamoyl group, di-tert-butylcarbamoyl group, dicyclobutylcarbamoyl group, ethylmethylcarbamoyl group, methylpropylcarbamoyl group, ethylpropylcarbamoyl group, butylmethylcarbamoyl group, butylethylcarbamoyl group and butylpropylcarbamoyl group.

The "lower alkylene group" means an alkylene group having one to four carbon atoms and includes, for example, methylene group, ethylene group and propylene group.

The phrase "may be bridged by a lower alkylene group" means the case that carbon atoms constituting the ring are bridged by the above-mentioned lower alkylene and refers to, for example, tropane when a piperidine ring is bridged.

The "oxoalkylene group" means a group corresponding to the alkylene group, and then one methylene of the alkylene group converted into carbonyl group.

The protective group used in "unprotected or protected hydroxyl group" as described in this specification includes, for example, alkyl protective groups such as a methyl group, tert-butyl group, benzyl group, trityl group and methoxymethyl group; silyl protective groups such as a trimethylsilyl group and tert-butyldimethylsilyl group; acyl protective groups such as formyl group, acetyl group and benzoyl group; and carbonate protective groups such as methoxycarbonyl group and benzyloxycarbonyl group.

The protective group used in "unprotected or protected carboxyl group" as described in this specification includes, for example, alkyl ester protective groups such as a methyl group, ethyl group, tert-butyl group, benzyl group, diphenylmethyl group and trityl group; and silyl ester protective groups such as a trimethylsilyl group and tert-butyldimethylsilyl group.

The protective group used in "unprotected or protected N-hydroxycarbamoyl group" as described in this specification includes, for example, tetrahydropyranyl group.

The "lower alkyl group substituted by unprotected or protected hydroxyl group" includes a case that the above-mentioned lower alkyl group is substituted by hydroxyl group. Specific examples of the "C1-4 alkyl group substituted by unprotected or protected hydroxyl group" are hydroxymethyl group, 1-hydroxyethyl group, 2-hydroxylethyl group, 1-hydroxy-1-methylethyl group, 1-hydroxypropyl group, 2-hydroxypropyl group, 3-hydroxypropyl group, 1-hydroxyl-1-methylpropyl group, 1-hydroxybutyl group, 2-hydroxybutyl group, 3-hydroxybutyl group, 4-hydroxybutyl group, 1-hydroxylcyclopropyl group and 1-hydroxycyclopropylmethyl group.

The phrase "Y may form a 5- or 6-membered ring with carbon atoms on the benzene ring when Z represents a bond" means the case that, when Z is a bond and Y is a lower alkylene group, one of carbon atoms of the lower alkylene group is bound to a carbon atom on the benzene ring via a lower alkylene group and, for example, specifically means the case that Y is ethylene group, and a carbon atom of the ethylene group adjacent to nitrogen atom is bound to carbon atom on the benzene ring via methylene group or ethylene group. Specific examples thereof are 2-indanyl group and 1,2,3,4-tetrahydro-2-naphthyl group.

The "lower alkyl group substituted by unprotected or protected carboxyl group" includes the above-mentioned lower alkyl group and a case that the above-mentioned lower alkyl group is substituted by carboxyl group. Specific examples of the "C1-4 alkyl group substituted by unprotected or protected carboxyl group" are carboxymethyl group, 1-carboxyethyl group, 2-carboxyethyl group, 1-carboxy-1-methylethyl group, 1-carboxypropyl group, 2-carboxypropyl group, 3-carboxypropyl group, 1-carboxy-1-methylpropyl group, 1-carboxybutyl group, 2-carboxybutyl group, 3-carboxybutyl group, 4-carboxybutyl group, 1-carboxycyclopropyl group and 1-carboxycyclopropylmethyl group.

The "halogen atom" includes fluorine, chlorine, bromine and iodine atoms.

The "lower alkyl group unsubstituted or substituted by one or more halogen atoms" includes the above-mentioned alkyl group, and a case that the alkyl group is substituted by one or more halogen atoms. Specific examples of the "C1-4 alkyl group substituted by one or more halogen atoms" are fluoromethyl group, 1-fluoroethyl group, 2-fluoroethyl group, 1-fluoro-1-methylethyl group, 1-fluoropropyl group, 2-fluoropropyl group, 3-fluoropropyl group, 1-fluoro-1-methylpropyl group, 1-fluorobutyl group, 2-fluorobutyl group, 3-fluorobutyl group, 4-fluorobutyl group, 1-fluorocyclopropyl group, 1-fluorocyclopropylmethyl group and trifluoromethyl group; chloromethyl group, 1-chloroethyl group, 2-chloroethyl group, 1-chloro-1-methylethyl group, 1-chloropropyl group, 2-chloropropyl group, 3-chloropropyl group, 1-chloro-1-methylpropyl group, 1-chlorobutyl group, 2-chlorobutyl group, 3-chlorobutyl group, 4-chlorobutyl group, 1-chloro cyclopropyl group, 1-chloro cyclopropylmethyl group and trichloromethyl group; and bromomethyl group, 1-bromoethyl group, 2-bromoethyl group, 1-bromo-1-methylethyl group, 1-bromopropyl group, 2-bromopropyl group, 3-bromopropyl group, 1-bromo-1-methylpropyl group, 1-bromobutyl group, 2-bromobutyl group, 3-bromobutyl group, 4-bromobutyl group, 1-bromocyclopropyl group, 1-bromocyclopropylmethyl group and tribromomethyl group, of which trifluoromethyl group is preferred.

The "lower alkoxy group" includes, for example, methoxy group, ethoxy group, propoxy group, isopropoxy group, butoxy group, isobutoxy group, sec-butoxy group, tert-butoxy group, pentyloxy group, isopentyloxy group, 3-pentyloxy group, tert-pentyloxy group, neopentyloxy group, 2-methylbutoxy group, 1,2-dimethylpropoxy group, 1-ethylpropoxy group, hexyloxy group, cyclopropyloxy group, cyclobutyloxy group, cyclopentyloxy group, cyclohexyloxy group, cyclopropylmethyloxy group, 1-cyclopropylethyloxy group, 2-cyclopropylethyloxy group, cyclobutylmethyloxy group, 2-cyclobutylethyloxy group and cyclopentylmethyloxy group.

The "lower alkoxy group unsubstituted or substituted by one or more halogen atoms" includes the above-mentioned lower alkoxy group and a case that the alkoxy group is substituted by one or more halogen atoms. Specific examples of the "C1-4 alkoxy group substituted by one or more halogen atoms" are fluoromethoxy group, 1-fluoroethoxy group, 2-fluoroethoxy group, 1-fluoro-1-methylethoxy group, 1-fluoropropoxy group, 2-fluoropropoxy group, 3-fluoropropoxy group, 1-fluoro-1-methylpropoxy group, 1-fluorobutoxy group, 2-fluorobutoxy group, 3-fluorobutoxy group, 4-fluorobutoxy group, 1-fluorocyclopropoxy group, 1-fluorocyclopropylmethyl group and trifluoromethoxy group; chloromethoxy group, 1-chloroethoxy group, 2-chloroethoxy group, 1-chloro-1-methylethoxy group, 1-chloropropoxy group, 2-chloropropoxy group, 3-chloropropoxy group, 1-chloro-1-methylpropoxy group, 1-chlorobutoxy group, 2-chlorobutoxy group, 3-chlorobutoxy group, 4-chlorobutoxy group, 1-chloro-cyclopropoxy group, 1-chloro-cyclopropylmethoxy group and trichloromethoxy group; and bromomethoxy group, 1-bromoethoxy group, 2-bromoethoxy group, 1-bromo-1-methylethoxy group, 1-bromopropoxy group, 2-bromopropoxy group, 3-bromopropoxy group, 1-bromo-1-methylpropoxy group, 1-bromobutoxy group, 2-bromobutoxy group, 3-bromobutoxy group, 4-bromobutoxy group, 1-bromocyclopropoxy group, 1-bromocyclopropylmethoxy group and tribromomethoxy group, of which trifluoromethoxy group is preferred.

The "lower alkylsulfonyl group" means —$SO_2$-(C1-4 alkyl group) and can be expressed as "C1-4 alkylsulfonyl group". Examples of the lower alkylsulfonyl group are methylsulfonyl group, ethylsulfonyl group, propylsulfonyl group, isopropylsulfonyl group, butylsulfonyl group, isobutylsulfonyl group, sec-butylsulfonyl group and tert-butylsulfonyl group.

The "lower alkanoyl group" includes, for example, formyl group, acetyl group and propionyl group.

The preferred substituents for the compounds of the present invention are as follows.

$R^1$ is preferably nitro group, a lower alkoxycarbonyl group, carbamoyl group unsubstituted or mono- or di-substituted by lower alkyl groups, unprotected or protected carboxyl group or tetrazolyl group, is more preferably nitro group, methoxycarbonyl group, ethoxycarbonyl group, carbamoyl group, dimethylcarbamoyl group, diethylcarbamoyl group, carboxyl group or tetrazolyl group, and is furthermore preferably carboxyl group.

$R^1$ is substituted at the ortho-, meta- or para-position with respect to carbon atom to which A bonds and is preferably substituted at the para-position (the 4-position).

As $R^1$, carboxyl group substituted at the para-position of A is more preferable.

$R^4$ is preferably cyano group, or a lower alkylsulfonyl group, is more preferably cyano group, methylsulfonyl group, ethylsulfonyl group, propylsulfonyl group, isopropylsulfonyl group or butylsulfonyl group, and is furthermore preferably cyano group.

$R^4$ is substituted at the ortho-, meta- or para-position with respect to carbon atom to which Z bonds, and is preferably substituted at the para-position.

$R^4$ is preferably cyano group substituted at the para-position.

W is preferably a group represented by —$NR^7$—.

$R^7$ is preferably a lower alkyl group, and is more preferably methyl group or ethyl group.

Each of the repetition numbers n in $G^1$ and $G^2$ is preferably 0 or 1.

The compound of Formula (I), (II), (III) or (IV) of the present invention may form acid addition salts, or may form salts with bases, depending on the kind of its substituents. The salts are not limited to any specific ones, as long as they are pharmaceutically acceptable. Specific examples thereof are acid-bound salts, the acid being mineral acid such as hydrochloric acid, hydrobromic acid, hydroiodic acid, sulfuric acid, nitric acid and phosphoric acid; organic carboxylic acids including aliphatic monocarboxylic acids such as formic acid, acetic acid, propionic acid, butyric acid, valeric acid, enanthic acid, capric acid, myristic acid, palmitic acid, stearic acid, lactic acid, sorbic acid and mandelic acid, aromatic monocarboxylic acids such as benzoic acid and salicylic acid, aliphatic dicarboxylic acids such as oxalic acid, malonic acid, succinic acid, fumaric acid, maleic acid, malic acid and tartaric acid; aliphatic tricarboxylic acids such as citric acid; organic sulfonic acids including aliphatic sulfonic acids such as methanesulfonic acid, ethanesulfonic acid and 2-hydroxyethanesulfonic acid, aromatic sulfonic acids such as benzenesulfonic acid and p-toluenesulfonic acid; acid addition salts such as acidic amino acid such as aspartic acid or glutamic acid, and salts with metal such as sodium, potassium, magnesium, calcium or aluminum, as well as another alkali metal or alkaline earth metal, salts with organic bases such as methylamine, ethylamine, ethanolamine, pyridine, lysine, arginine and ornithine; and ammonium salts.

The above salt can be prepared according to a conventional procedure: for example, the compound of the present invention and a solution containing a desired acid or base at equivalent amounts are mixed and the resulting salt is collected by filtration or by removal of a solvent. Further, the compound of the present invention or a salt thereof can form a solvate in the presence of a solvent such as water, ethanol or glycerol.

The salts of the compounds of the present invention may include mono- or di-salts. The compounds of the present invention may simultaneously form both acid addition salt and salt with a base depending on the substituent on the side chains of the compounds.

The present invention further includes hydrates, various pharmaceutically acceptable solvates and polymorphic crystals of the compound represented by Formula (I), (II), (III) or (IV). Naturally, the present invention is not limited to the compounds mentioned in the examples below, but include all the compounds represented by Formula (I), (II), (III) or (IV), and pharmaceutically acceptable salts thereof.

Next, the methods for producing the compounds of the present invention will be disclosed and the processes involved therein will be described. The definitions of A, A'', A''', L, W, W''', Z, Y, $G^1$, $G^2$, $R^1$, $R^{1'}$, $R^2$, $R^3$, $R^4$, $R^5$, $R^6$, $R^7$, $R^{7'}$, P, X, Y and Z in Formulae (I), (VI), (VII), (XV), (XVI), (XX) and (XXI) cited in the Reaction Schemes and the description of Manufacturing Methods 1 to 4 have the same meanings as defined above, unless otherwise stated.

The compounds of the present invention represented by Formula (I), or salts thereof can be prepared according to Manufacturing Methods 1 to 4 described below or to their modifications from compounds as represented by Formula (XXIII) (wherein $R^7$ and Z have the same meanings as defined above), Formula (XXIV), Formula (V) (wherein P has the same meaning as defined above), Formula (VIII), Formula (IX) (wherein X has the same meaning as defined above), Formulae (X), (XI), (XII), (XIII), (XIV), (XVII), (XVIII) and (XIX), which may be easily synthesized starting from the compounds known in the art or from commercially available compounds. The definitions of A, A'', A''', L, W, W''', Z, Y, $G^1$, $G^2$, $R^1$, $R^{1'}$, $R^2$, $R^3$, $R^4$, $R^5$, $R^6$, $R^7$, $R^{7'}$, P, X, Y and Z in the Formulae have the same meanings as defined above, unless otherwise stated. A starting material, intermediate material and product of each process may be used as salt thereof, if necessary.

Next, the manufacturing methods will be described in detail below.

<Manufacturing Method 1>

It is possible to prepare a compound represented by Formula (I) or a salt thereof, from a compound represented by Formula (XXIII), and another compound represented by Formula (XXIV) or Formula (V), by employing appropriate processes cited in Reaction Scheme 1. L defined in A'' in Formula (XXIII) represents a bond.

REACTION SCHEME 1

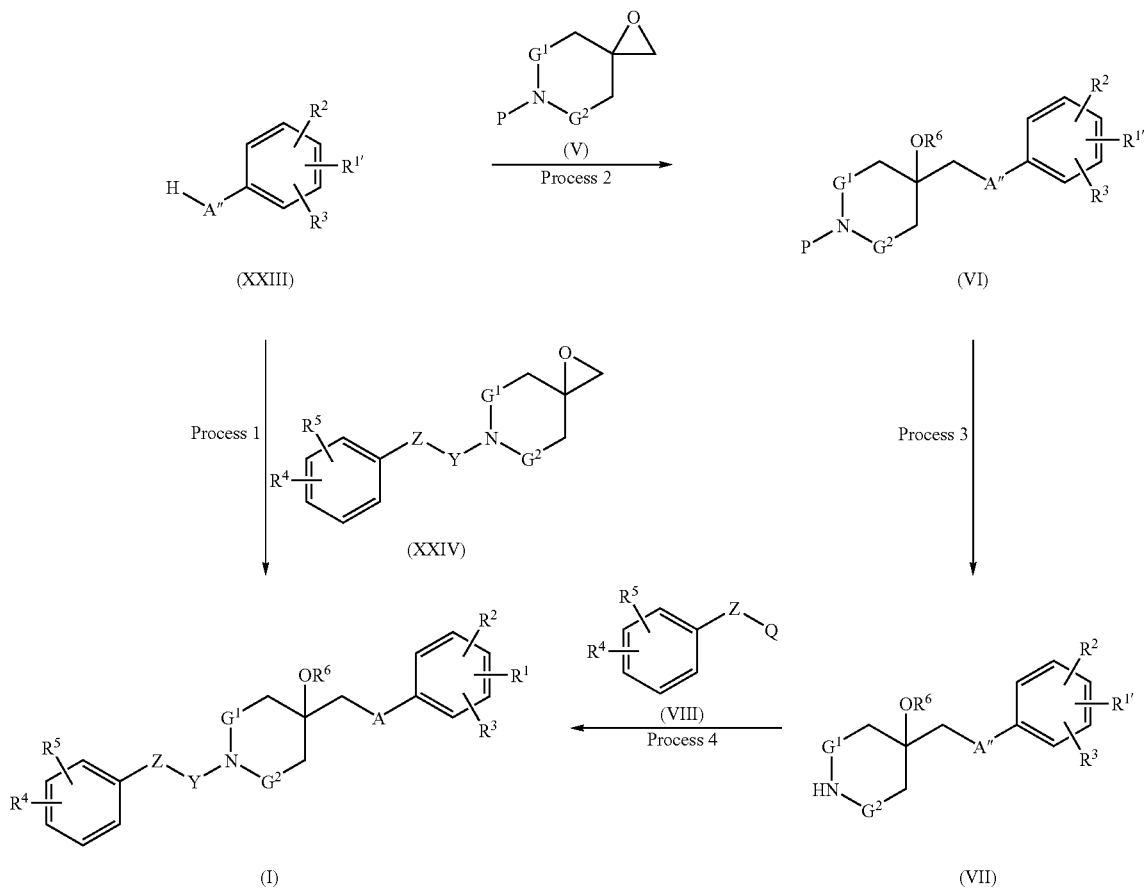

<Process 1>

The compound represented by Formula (I) or a salt thereof can be manufactured from a compound represented by Formula (XXIII) and a compound represented by Formula (XXIV). The compound represented by Formula (XXIII) and the compound represented by Formula (XXIV) are reacted in a solvent inert to the reaction, for example, chosen from the group comprising halogenated hydrocarbon solvents such as dichloromethane and chloroform; ether solvents such as diethyl ether and tetrahydrofuran; hydrocarbon solvents such as toluene, benzene and hexane; polar solvents such as dimethylformamide and dimethyl sulfoxide; alcohol solvents such as methanol and ethanol; acetonitrile, acetone, water or acetic acid; and arbitrary mixtures of these solvents, or without using a solvent, in the presence or absence of an acid catalyst including Lewis acid such as lithium perchlorate, scandium(III) trifluoromethanesulfonate or lanthanum(III) trifluoromethanesulfonate or in the presence or absence of a base catalyst and in the presence or absence of a crown ether such as 18-crown-6 at a temperature between 0° C. and the temperature at which the reaction mixture will reflux, followed by converting lower alkanoyl group to lower alkyl group by reducing reaction when A" is amino group substituted by a lower alkanoyl group and converting, as needed, $R^{1'}$ into $R^1$. The compound represented by Formula (I) can be also manufactured by reacting the compound represented by Formula (XXIII) and the compound represented by Formula (XXIV) in diethyl ether in the presence of a neutral alumina at room temperature, according to the method described by Gary H. Posner et al. in Journal of the American Chemical Society, 99, 8208-8214 (1977), followed by converting lower alkanoyl group to lower alkyl group by reduction when A" represents amino group substituted by a lower alkanoyl group and converting, as needed, $R^{1'}$ into $R^1$. The compound represented by Formula (I) can be also manufactured by reacting the compound represented by Formula (XXIII) with the compound represented by Formula (XXIV) or a salt thereof in a solvent inert to the reaction chosen from an alcoholic solvent such as methanol or ethanol, or water, in the presence or absence of cyclodextrins such as β-cyclodextrin, followed by converting lower alkanoyl group to lower alkyl group by reducing reaction when A" represents amino group substituted by a lower alkanoyl group and converting, as needed, $R^{1'}$ into $R^1$.

The tertiary hydroxyl group formed as a result of addition can be alkylated, for example, by reacting the compound with an alkylating agent in a solvent inert to the reaction, such as dimethylformamide or dimethylimidazolidone in the presence of a base such as sodium hydride at a temperature between −20° C. and the temperature at which the reaction mixture will reflux, preferably at a temperature from an ice-cooling temperature to room temperature. Examples of the alkylating agent are alkyl halides such as methyl iodide; and dialkyl sulfates such as dimethyl sulfate.

It is also possible to obtain the compound represented by Formula (I) or a salt thereof according to Processes 2, 3 and 4 described below.

<Process 2>

It is possible to prepare the compound represented by Formula (VI) from the compound represented by Formula (XXIII) and the compound represented by Formula (V) according to Process 1. The protective group P includes, for example, alkyl protective groups such as benzyl group, trityl group and methoxymethyl group; and carbamate protective groups such as tert-butoxycarbonyl group and benzyloxycarbonyl group, as described in T. W. Greene and P. G. M. Wuts (eds.), "Protective Groups in Organic Synthesis," 3rd Ed., John Wiley and Sons, 1999.

<Process 3>

It is possible to prepare the compound represented by Formula (VII) by removing the protective group at the 1-position of piperidine from the compound represented by Formula (VI).

The protective group at the 1-position of piperidine may be removed from the compound represented by Formula (VI) according to the method introduced in the above review, i.e., "Protective Groups in Organic Synthesis," 3rd Ed., 1999. For example, when the protective group P is a benzyl group or benzyloxycarbonyl group, removal of the protective group will be achieved by placing the compound in an alcoholic solvent such as methanol or ethanol, or a solvent such as ethyl acetate, acetic acid or water under hydrogen atmosphere or in the presence of ammonium formate in the presence of a catalyst such as palladium on carbon or platinum oxide at a temperature between 0° C. and the temperature at which the reaction mixture will reflux. Then, the compound represented by Formula (VII) will be prepared. When the protective group P is, for example, tert-butoxycarbonyl group, removal of the protective group will be achieved by treating the compound with an acid such as trifluoroacetic acid or hydrochloric acid in the presence or absence of anisole at a temperature between 0° C. and the temperature at which the reaction mixture will reflux. Then, the compound represented by Formula (VII) will be prepared.

<Process 4>

It is possible to allow the compound represented by Formula (VII) to react with the compound represented by Formula (VIII) according to the method described below appropriately chosen depending on the type of Q. The compound represented by Formula (I) or a salt thereof can be manufactured by converting, as needed, $R^{1'}$ into $R^1$ in the resulting compound.

(Method A)

If Q is a halogenated alkyl group, methanesulfonyloxyalkyl group, or arylsulfonyloxyalkyl group such as p-toluenesulfonyloxyalkyl group, each of which may be substituted by phenyl group unsubstituted or substituted by $R^4$, or if Z is a bond and Q is a halogenated alkylene group which forms a 5- or 6-membered ring with carbon atoms on the benzene ring, the compound represented by Formula (VII) and the compound represented by Formula (VIII) are allowed to react in a solvent inert to the reaction, for example, halogenated hydrocarbon solvents such as dichloromethane and chloroform; ether solvents such as diethyl ether and tetrahydrofuran; hydrocarbon solvents such as toluene, benzene and hexane; and polar solvents such as dimethylformamide and dimethyl sulfoxide, in the presence or absence of an organic base such as triethylamine or pyridine, or in the presence or absence of an inorganic base such as potassium carbonate, at a temperature between 0° C. and the temperature at which the reaction mixture will reflux, followed by converting, as needed, $R^{1'}$ into $R^1$, in the obtained compound. Then, the compound represented by Formula (I) will be prepared. When Q is a halogenated alkyl group which may be substituted by phenyl group unsubstituted or substituted by $R^4$, or when Z is a bond and Q is a halogenated alkylene group which forms a 5- or 6-membered ring with carbon atoms on the benzene ring, the catalyst, for example, sodium iodide can be used.

(Method B)

If Q is formyl group, benzoyl group unsubstituted or substituted by $R^4$, a formylalkyl group, a benzoylalkyl group unsubstituted or substituted by $R^4$ on its benzene ring, or if Z is a bond and Q is an oxoalkylene group which forms 5- or 6-membered ring with carbon atoms on the benzene ring, the compound represented by Formula (VII) and the compound represented by Formula (VIII) are reacted in a solvent, for example, chosen from the group comprising aromatic hydrocarbon solvents such as toluene and benzene; halogenated hydrocarbon solvents such as dichloromethane and chloroform; and alcoholic solvents such as methanol and ethanol, in the presence or absence of an acidic catalyst such as acetic acid or hydrochloric acid, in combination with an appropriate reducing agent, followed by converting, as needed, $R^{1'}$ into $R^1$ in the obtained compound. Then, the compound represented by Formula (I) will be obtained. Generally speaking, for this reaction, any reducing agent that can reduce imino group into amino group is applicable, the preferred reducing agent includes sodium triacetoxyborohydride, sodium borohydride, lithium borohydride, diisobutylaluminum hydride and sodium cyanoborohydride and so on. The reduction may proceed at a temperature between −78° C. and room temperature, preferably at room temperature, for a period in which the reaction will proceed sufficiently, specifically, a period from three to twelve hours.

(Method C)

When Q is carboxyl group or carboxyalkyl group, it is possible to prepare the compound represented by Formula (I) or a salt thereof by reacting the compound represented by Formula (VII) and the compound represented by Formula (VIII) in a solvent inert to the reaction, for example, chosen from the group comprising halogenated hydrocarbon solvents such as dichloromethane and chloroform; ether solvents such as diethyl ether and tetrahydrofuran; hydrocarbon solvents such as toluene, benzene and hexane; and polar solvents such as dimethylformamide and dimethyl sulfoxide, in the presence of a condensing agent such as 1-ethyl-3-(3-dimethylaminopropyl)carbodiimide hydrochloride (water-soluble carbodiimide hydrochloride, WSC.HCl) or dicyclohexylcarbodiimide (DCC), at a temperature between 0° C. and the temperature at which the reaction mixture will reflux to yield an amide compound, and reacting the formed amide bond with a reducing agent such as lithium aluminum hydride or diisobutylaluminum hydride, or a borane complex such as borane-methyl sulfide complex or borane-tetrahydrofuran complex, in a solvent inert to the reaction, for example, chosen from the group comprising ether solvents such as diethyl ether and tetrahydrofuran; and aromatic hydrocarbon solvents such as toluene and benzene, at a temperature between 0° C. and the temperature at which the reaction mixture will reflux, followed by converting, as needed, $R^{1'}$ into $R^1$ in the obtained compound.

The reaction between the compound represented by Formula (VII) and the compound represented by Formula (VIII) can be carried out in a solvent inert to the reaction, for example, chosen from the group comprising halogenated hydrocarbon solvents such as methylene chloride and chloroform; ether solvents such as diethyl ether and tetrahydrofuran; and hydrocarbon solvents such as toluene, benzene and hexane, in the presence of a dehydrating agent such as phosphorus oxychloride and of a base such as pyridine or triethylamine, at a temperature between −20° C. and the temperature at which the reaction mixture will reflux.

The reaction between the compound represented by Formula (VII) and the compound represented by Formula (VIII) can be carried out by converting the compound represented by Formula (VIII) into its acyl chloride by using thionyl chloride, etc. and then by allowing the acyl chloride to react in a solvent chosen from the group comprising halogenated hydrocarbon solvents such as dichloromethane and chloroform; ether solvents such as diethyl ether and tetrahydrofuran; hydrocarbon solvents such as toluene, benzene and hexane; and basic solvents such as pyridine and triethylamine, in the presence of an organic base such as triethylamine or pyridine or an inorganic base such as potassium carbonate, at a temperature between −20° C. and the temperature at which the reaction mixture will reflux.

<Manufacturing Method 2>

It is possible to prepare the compound represented by Formula (I) or a salt thereof from a compound represented by Formula (IX) in combination with a compound represented by Formula (X) or a compound represented by Formula (XI), by employing appropriate processes cited in Reaction Scheme 2.

<Process 1>

The compound represented by Formula (I) or a salt thereof can be manufactured by reacting the compound represented by Formula (IX) and the compound represented by Formula (X) in a solvent inert to the reaction, for example, chosen from the group comprising halogenated hydrocarbon solvents such as dichloromethane and chloroform; ether solvents such as diethyl ether and tetrahydrofuran; hydrocarbon solvents such as toluene, benzene and hexane; and polar solvents such as dimethylformamide and dimethyl sulfoxide, or without using a solvent, in the presence or absence of a base catalyst at a temperature between 0° C. and the temperature at which the reaction mixture will reflux, followed by converting, as needed, $R^{1'}$ into $R^1$.

It is also possible to obtain the compound represented by Formula (I) or a salt thereof according to Processes 2, 3 and 4 described below.

<Process 2>

It is possible to prepare the compound represented by Formula (VI) by reacting the compound represented by Formula (IX) and the compound represented by Formula (XI) in a solvent inert to the reaction, for example, chosen from the group comprising halogenated hydrocarbon solvents such as dichloromethane and chloroform; ether solvents such as diethyl ether and tetrahydrofuran; hydrocarbon solvents such as toluene, benzene and hexane; and polar solvents such as dimethylformamide and dimethyl sulfoxide, or without using

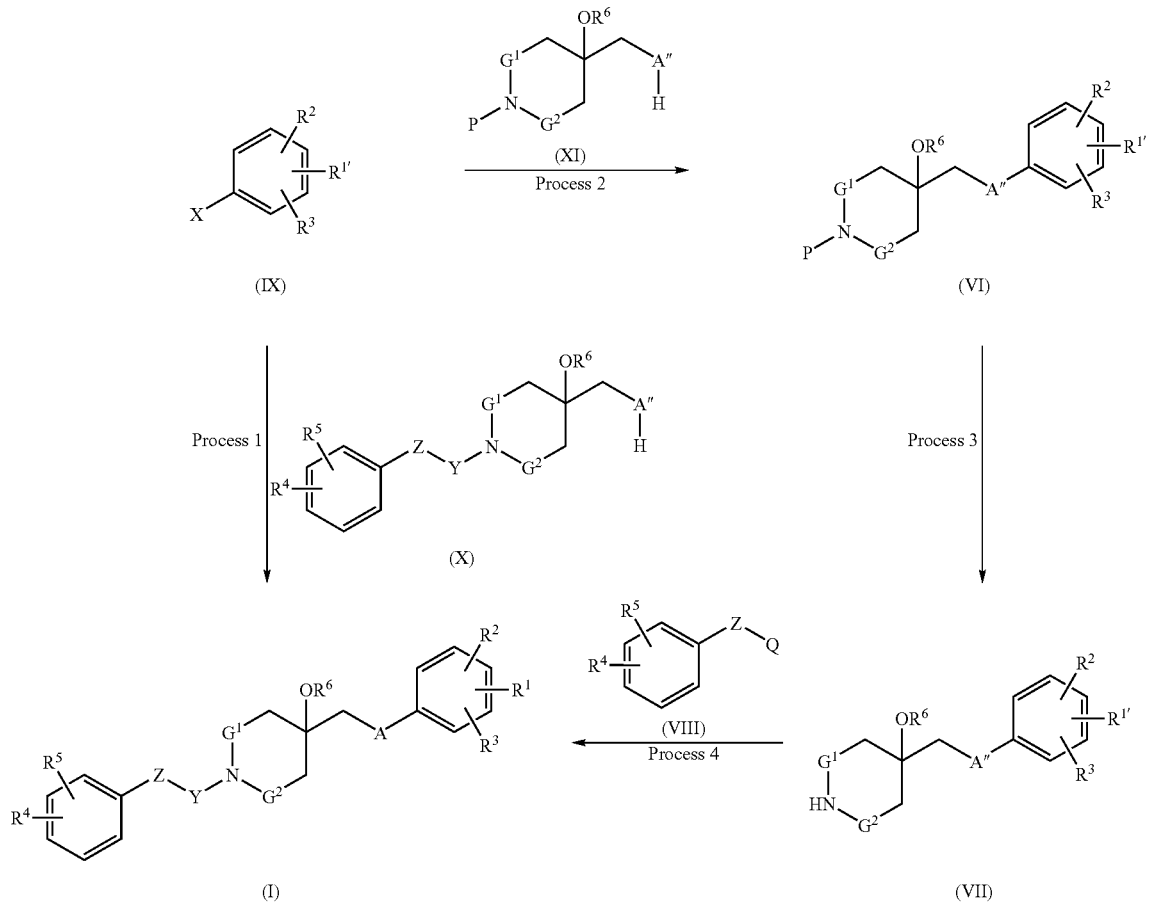

a solvent, in the presence or absence of a base catalyst at a temperature between 0° C. and the temperature at which the reaction mixture will reflux.

<Process 3>

It is also possible to prepare the compound represented by Formula (VII) from the compound represented by Formula (VI) according to Process 3 of Manufacturing Method 1.

<Process 4>

It is also possible to prepare the compound represented by Formula (I) or a salt thereof from the compound represented by Formula (VII) and the compound represented by Formula (VIII) according to Process 4 of Manufacturing Method 1.

<Manufacturing Method 3>

It is possible to prepare the compound represented by Formula (I) or a salt thereof from a compound represented by Formula (XII) in combination with a compound represented by Formula (XIII) or a compound represented by Formula (XIV) by employing appropriate processes cited in Reaction Scheme 3.

It is also possible to prepare the compound represented by Formula (I) or a salt thereof according to Processes 2, 3 and 4 described below.

<Process 2>

The compound represented by Formula (XV) can be prepared from the compound represented by Formula (XII) and the compound represented by Formula (XIV) according to Process 4 of Manufacturing Method 1.

<Process 3>

The compound represented by Formula (XVI) can be prepared from the compound represented by Formula (XV) according to Process 3 of Manufacturing Method 1.

<Process 4>

The compound represented by Formula (I) or a salt thereof can be prepared from a compound represented by Formula (XVI) or the compound represented by Formula (VIII) according to Process 4 of Manufacturing Method 1.

REACTION SCHEME 3

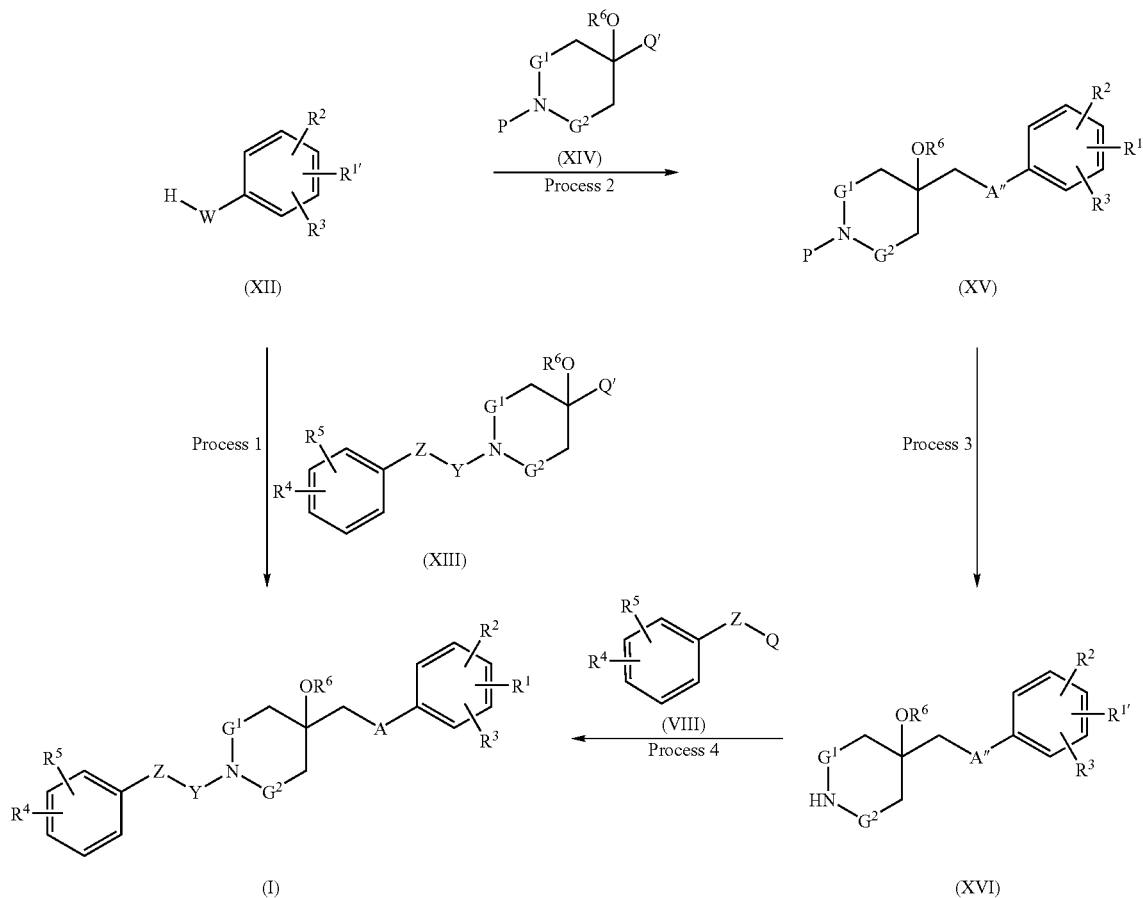

<Process 1>

It is possible to prepare the compound represented by Formula (I) or a salt thereof from the compound represented by Formula (XII) and the compound represented by Formula (XIII) by reacting these compounds according to Process 4 of Manufacturing Method 1, followed by converting, as needed, $R^{1'}$ into $R^1$.

<Manufacturing Method 4>

It is possible to prepare the compound represented by Formula (I) or a salt thereof from a compound represented by Formula (XVII) in combination with a compound represented by Formula (XVIII) or a compound represented by Formula (XIX), by employing appropriate processes cited in Reaction Scheme 4.

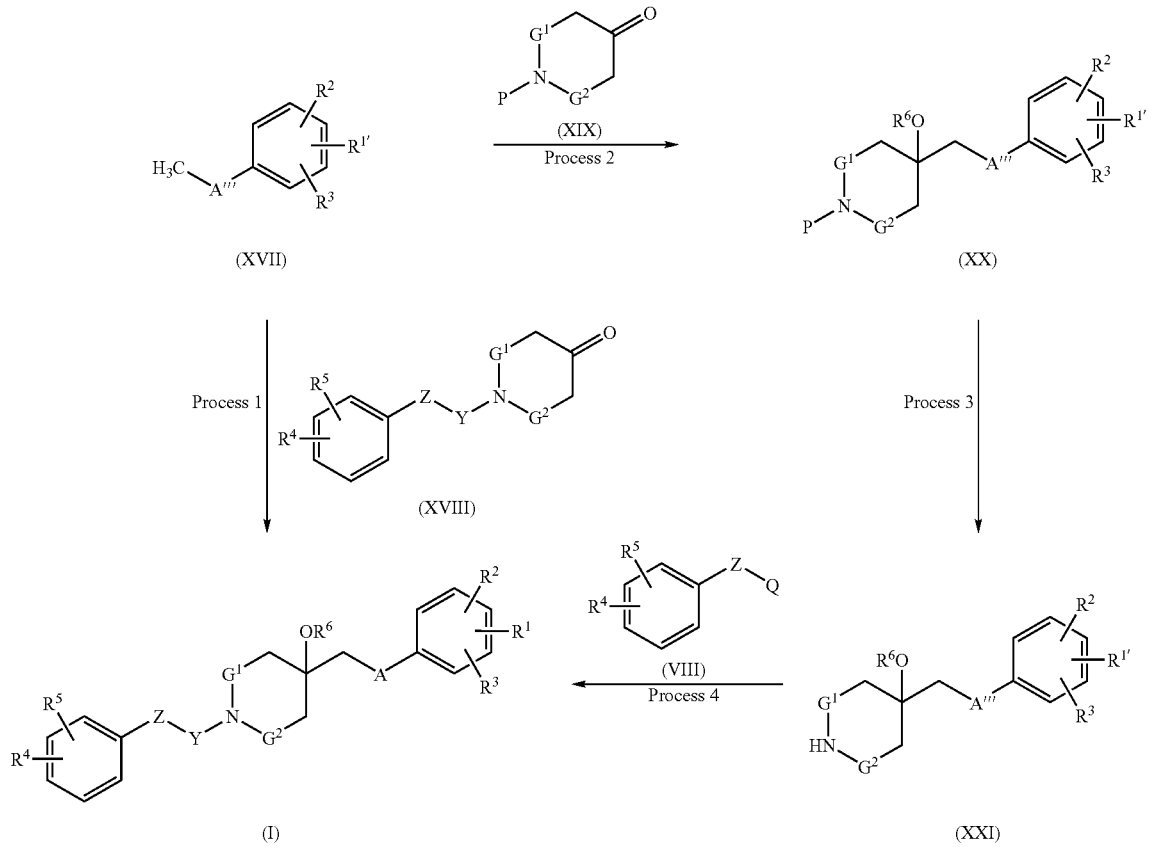

Reaction Scheme 4

<Process 1>

The compound represented by Formula (I) or a salt thereof can be prepared by adding the compound represented by Formula (XVII) to the compound represented by Formula (XVIII), alkylating, as needed, formed hydroxyl group, and reducing amide bond when A''' is —(C═O)NR$^7$.

The addition reaction can be carried out by subjecting the compound represented by Formula (XVII) with a metal amide reagent such as lithium diisopropylamide, lithium hexamethyldisilazide or potassium hexamethyldisilazide, or an organometal reagent such as tin(II) triflate in a solvent inert to the reaction chosen from, for example, the group comprising ether solvents such as diethyl ether and tetrahydrofuran; and hydrocarbon solvents such as benzene and hexane, at a temperature between −100° C. and room temperature, to thereby yield a metal enolate, and allowing the metal enolate to react with the compound represented by Formula (XVIII) at a temperature between −100° C. and room temperature.

The amide bond can be reduced according to Method C of Process 4 of Manufacturing Method 1.

The tertiary hydroxyl group formed as a result of the addition reaction can be alkylated by reacting the compound with an alkylating agent in a solvent inert to the reaction, such as dimethylformamide or dimethylimidazolidone in the presence of a base such as sodium hydroxide at a temperature between −20° C. and the temperature at which the reaction mixture will reflux, preferably at a temperature from an ice-cooling temperature to room temperature. Examples of the alkylating agent are alkyl halides such as methyl iodide; and dialkyl sulfates such as dimethyl sulfate.

The compound represented by Formula (I) can also be prepared according to following Processes 2, 3 and 4.

<Process 2>

A compound represented by Formula (XX) can be prepared from the compound represented by Formula (XVII) and a compound represented by Formula (XIX) according to Process 1.

<Process 3>

A compound represented by Formula (XXI) can be prepared from the compound represented by Formula (XX) according to Process 3 of Manufacturing Method 1. If A''' in the compound represented by Formula (XX) is —(C═O) NR$^7$, it is also possible to subject the resulting compound to Process 4 without reducing the amide bond.

<Process 4>

The compound represented by Formula (I) and salt thereof can also be prepared from the compound represented by Formula (XXI) and the compound represented by Formula (VIII) according to Process 4 of Manufacturing Method 1, and then reducing amide bond when A''' is —(C═O)NR$^7$.

The compounds prepared as above by the above-mentioned processes may be converted to another during process, according to the methods described below.

When W or W'' is a group represented by —NH—, it is possible to convert the compound to a compound wherein W or W'' is —NR$^7$— (wherein R$^7$ represents a lower alkyl group) by using a lower alkyl halides, a lower alkyl methanesulfonate, a lower alkyl arylsulfonate, a lower alkyl aldehyde or a lower alkyl carboxylic acid according to Process 4 of Manufacturing Method 1. Also it is possible to convert to a group represented by —N(CH$_3$)— by allowing the compound to react with a reducing agent such as sodium borohydride in the presence or absence of a solvent inert to the reaction, for example, an ether solvents such as tetrahydrofuran, in the presence of sulfuric acid, by using formalin.

When W or W" is a group represented by —S— or —SO—, it is possible to convert the compound to a compound wherein W or W" is a group represented by SO or —SO$_2$— by allowing the compound to react with an oxidizing agent such as m-chloroperbenzoic acid or sodium periodate in a solvent inert to the reaction chosen from, for example, the group comprising halogenated hydrocarbon solvents such as dichloromethane and chloroform; and alcoholic solvents such as methanol.

If the compound has a lower alkoxycarbonyl group as a substituent, it is possible to convert the alkoxycarbonyl group to carboxyl group, by a known method, for example, by hydrolyzing the compound in a solvent chosen from, for example, alcoholic solvents such as methanol and ethanol in the presence of an alkaline aqueous solution of lithium hydroxide or sodium hydroxide at a temperature between room temperature and the temperature at which the reaction mixture will reflux, or by reacting with a lithium alkylthiolate in a solvent inert to the reaction, for example, polar solvents such as dimethylformamide (DMF) and hexamethylphosphoramide (HMPA), or by reacting with, for example, potassium tert-butoxide or potassium trimethylsilanolate in a solvent inert to the reaction, for example, ether solvents such as tetrahydrofuran and alcoholic solvents such as tert-butanol. Further, it is possible to convert the resulting carboxyl group to a carbamoyl group unsubstituted or mono- or di-substituted by lower alkyl groups, by subjecting the compound to the condensing reaction as described in Method C of Process 4 of Manufacturing Method 1 above. It is also possible to convert the carboxyl group to protected or unprotected N-hydroxycarbamoyl group, by subjecting the carboxyl group to a condensing reaction with hydroxylamine unprotected or protected such as tetrahydropyranyl group according to Method C of Process 4 of Manufacturing Method 1.

Further, if the compound prepared as above has formyl group as a substituent on its aromatic ring, it is possible to convert the formyl group to hydroxymethyl group, according to a conventional procedure, for example, by reacting the compound with a reducing agent such as sodium borohydride, sodium triacetoxyborohydride or sodium cyanoborohydride in a solvent including an alcoholic solvent such as methanol or ethanol.

If the compound has cyano group as a substituent on its aromatic ring, it is possible to convert the cyano group to carbamoyl group according to a conventional procedure, for example, by hydrolysis in the presence of an acid such as hydrochloric acid or sulfuric acid, or a base such as sodium hydroxide.

If the compound prepared as above has halogen atom, preferably bromine atom, as a substituent on its aromatic ring, it is possible to convert the halogen atom to cyano group, according to a conventional procedure, for example, by allowing the compound to react with, for example, copper(I) cyanide or potassium cyanide in a solvent inert to the reaction, for example, chosen from polar aprotic solvents such as dimethylformamide, dimethyl sulfoxide and dimethylimidazolidone, at a temperature between room temperature and the temperature at which the reaction mixture will reflux. This reaction may proceed in the presence of a catalyst chosen from transition metal complexes including palladium complexes such as palladium acetate, and nickel complexes such as tetrakistriphenylphosphine nickel.

If the compounds prepared as above have, as a substituent, a reactive group such as a hydroxyl group, amino group or carboxyl group, it is possible to protect the group with a protective group appropriately chosen at one process, and then to remove the protective group at another as needed. Introduction and removal of such a protective group may be achieved by any method appropriately chosen depending on the natures of the group to be protected and protective group, for example, by the methods as described in the above-mentioned review, "Protective Groups in Organic Synthesis," 3rd Ed., 1999.

Among the reaction intermediates used in the above manufacturing methods, it is possible to prepare the compound represented by Formula (XVIII) by a known method, for example, by allowing the compound represented by Formula (VIII) to react with 4-piperidone or its equivalent according to Process 4 of Manufacturing Method 1. Alternatively, it is possible to obtain the compound represented by Formula (XVIII) by reacting the compound represented by Formula (XXII):

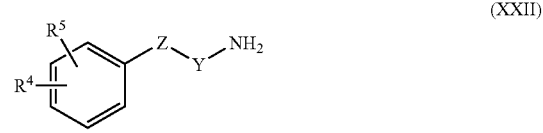

(XXII)

by the method described by Huegi et al. in J. Med. Chem. 26:42, 1983, or by Mannich reaction of the compound represented by Formula (XXII) with 1,3-acetonedicarboxylic derivative, followed by decarboxylation.

The compound represented by Formula (XXIV) can be prepared, for example, by allowing the compound represented by Formula (VIII) to react with trimethylsulfoxonium iodide or trimethylsulfoxonium bromide, etc. in the present of a base, in a solvent inert to the reaction, for example, a polar solvent such as dimethyl sulfoxide. It is also possible to prepare the compound represented by Formula (XXIV) by reacting the compound represented by Formula (XVIII) with methylenetriphenylphosphorane, etc. in a solvent inert to the reaction including ether solvents such as ether, dioxane and tetrahydrofuran; and polar solvents such as dimethylformamide and dimethyl sulfoxide to convert carbonyl group to methylene group, followed by reacting the methylene group with m-chloroperbenzoic acid, etc. in a solvent inert to the reaction including halogenated hydrocarbon solvents such as dichloromethane and chloroform to oxidize the methylene group, and by selectively reducing only N-oxide, if formed.

It is possible to prepare the compound represented by Formula (V) by reacting a compound of the following Formula (XIX):

(XIX)

wherein G$^1$, G$^2$ and P have the same meanings as defined above, which is a commercially available compound or can be easily produced by a known method, with trimethyl sulfoxonium iodide or trimethyl sulfoxonium bromide in the present of a base in a solvent inert to the reaction including polar solvents such as dimethyl sulfoxide. It is also possible to prepare the compound represented by Formula (V) by reacting the compound represented by Formula (XIX) with methylenetriphenylphosphorane, etc. in a solvent inert to the reaction, for example, ether solvents such as ether (diethyl ether), dioxane and tetrahydrofuran; and polar solvents such as dimethylformamide and dimethyl sulfoxide, to convert carbonyl group to methylene group, followed by reacting the methylene group with m-chloroperbenzoic acid, etc. in a solvent inert to the reaction, for example, halogenated hydrocarbon solvents such as dichloromethane and chloroform to oxidize the methylene group, and by selectively reducing only N-oxide, if formed.

It is possible to prepare the compound represented by Formula (X) or the compound represented by Formula (XI), when, for example, A"-H is hydroxyl group, by hydrolyzing the compound represented by Formula (XXIV) or the compound represented by Formula (V) in a solvent inert to the reaction, for example, chosen from the group of ether solvents such as dioxane and tetrahydrofuran; and polar solvents such as dimethylformamide and dimethyl sulfoxide, by using a base such as sodium hydroxide or potassium hydroxide. When A" is amino group unprotected or protected by a lower alkyl in the compound represented by Formula (X) or the compound represented by Formula (XI), it is possible to produce each compound by reacting the compound represented by Formula (XXIV) or the compound represented by Formula (V) with ammonia or a lower alkylamine in the presence or absence of a base in a solvent inert to the reaction, for example, chosen from the group of ether solvents such as dioxane and tetrahydrofuran; and polar solvents such as dimethylformamide and dimethyl sulfoxide. When the resulting compound has amino group as A", it is possible to further produce the compound represented by Formula (X) or the compound represented by Formula (XI) wherein A" is amino group substituted by a lower alkanoyl group or amino group substituted by a lower alkyl group, according to the method described in Method C of Process 4 of Manufacturing Method 1.

EXPERIMENTAL EXAMPLES

The present invention will be illustrated concretely in the following experimental examples. However, they never intended to limit the area of the invention.

Experimental Example 1-1

Inhibitory Effect on Citric Acid-Induced Cough Reflex in Guinea Pigs

Guinea pigs were fasted overnight. They were fixed to a plethysmograph, and then the change of inner pressure in the plethysmograph (body side) was recorded on an ink-recording paper (Nihon Kohden Corporation; WI-642G) via the differential pressure transducer (Nihon Kohden Corporation; TP-602T) and the respiration amplifier (Nihon Kohden Corporation; AR-601G). Using a nebulizer (OMRON Corporation; NE-U12), 20 W/V % citric acid solution was sprayed into the plethysmograph (head side) for 2 min (about 1 mL/min). The number of cough response for 15 min after the spray was measured.

The cough response was measured 3 hrs before and 1 hr after oral treatment. The test compound was not administered to the guinea pigs showing 5 coughs response or less before the treatment. The ratio of cough response between before and after the treatment (Post/Pre×100) was calculated, and the percent inhibition of the test compound on cough reflex induced by citric acid was determined according to the following formula:

$$[(CRR_{control} - CRR_{test})/(CRR_{control})] \times 100 \, (\%)$$

$CRR_{control}$: Ratio (%) of cough response in the control group $CRR_{test}$: Ratio (%) of cough response in the compound-treated group

TABLE 1-1

Inhibitory Effect on Citric Acid-Induced Cough Reflex in Guinea Pigs

| Test Compound | Dosage (mg/kg) | Percent inhibition on cough reflex (%) |
|---|---|---|
| Example 26 | 30 | 59 |
| Codeine phosphate | 10 | 40 |
| | 30 | 44 |
| | 60 | 66 |
| Theophylline | 20 | 37 |

These results show that oral treatment with the compound of the present invention inhibits cough reflex induced by citric acid. It is shown that these compounds have low toxicity since they showed no effect on general behaviors in animals.

Experimental Example 1-2

Inhibitory Action on Citric Acid-Induced Cough Reflex in Guinea Pigs

Guinea pigs were fasted overnight. They were fixed to an nasal inhalation-exposure apparatus for small animals (M.I.P.S. Co., Ltd.), and then 20 W/V % citric acid solution was sprayed into the plethysmograph for 2 min (about 1 mL/min) using a nebulizer (M.I.P.S. Co., Ltd.). The number of cough response for 15 min after the spray was measured.

The cough response was measured 3 hrs before and 1 hr after oral treatment. The test compound was not administered to the guinea pigs showing 5 cough responses or less before the treatment. The ratio of cough response between before and after the treatment (Post/Pre×100) was calculated, and the percent inhibition of the test compound on cough reflex induced by citric acid was determined according to the following formula:

$$[(CRR_{control} - CRR_{test})/(CRR_{control})] \times 100 \, (\%)$$

$CRR_{control}$: Ratio (%) of cough response in the control group $CRR_{test}$: Ratio (%) of cough response in the compound-treated group.

TABLE 1-2

Inhibitory Effect on Citric Acid-induced Cough Reflex in Guinea Pigs

| Test Compound | Dosage (mg/kg) | Percent inhibition on cough reflex (%) |
|---|---|---|
| Example 29 | 30 | 39 |
| Example 34 | 30 | 39 |
| Example 35 | 30 | 43 |

These results show that oral treatment with the compounds of the present invention inhibits cough reflex induced by citric acid. It is shown that these compounds have low toxicity since they showed no effect on general behaviors in animals.

Experimental Example 2

Toxicological Study

The compound of Example 36 was orally given to 6-week-old Wistar Hannover female rats at 40 mg/kg. All the rats showed no abnormality in general behaviors, and they survived during the examination period.

The compound of Example 26 was orally given to 6-week-old Wistar Hannover female rats at 400 mg/kg/day once daily for 14 days. All the rats survived until 24 hours after the final treatment, and they showed no abnormality in their general behaviors, weight gains, and food consumptions. No abnormal findings were observed in the hematological and biochemical examinations, in organ weights and in histopathological tests.

The compound of Example 36 or Example 26 was orally given to 3-year-old male rhesus monkeys at 20 mg/kg/day or 40 mg/kg/day, respectively, once daily for 14 days. The monkeys survived until 24 hours after the final treatment, and they showed no abnormality in their weight gains and general behaviors. No apparent toxicological findings were observed in the hematological and biochemical examinations, in organ weights and in histopathological tests.

In Holter ECG test, the compound of Example 36 or Example 26 was orally given to 4-year-old male rhesus monkeys at 40 mg/kg and 80 mg/kg, respectively. These compounds showed no effect on electrocardiogram.

Experimental Example 3

Pharmacokinetics

The compound of Example 36 or Example 26 was studied about time-course of plasma concentration after single oral treatment to 3- or 4-year-old male rhesus monkeys. These two compounds showed high bioavailability. The maximum plasma concentration (Cmax) and the area under the plasma concentration-time curve (AUC) of these compounds increased almost in proportion to the doses. The relationship between the dose and the plasma concentration was linear. These two compounds exhibited almost no inhibitory effect on human drug-metabolizing enzymes. Moreover, these compounds were metabolically stable in liver microsomes and hepatocytes of humans, monkeys, dogs, and rats. Therefore, it can be considered that these compounds are unlikely to be metabolized by first pass effect.

These experimental results show that oral treatment with the compounds of the present invention has inhibitory effects on citric acid-induced cough reflex in guinea pigs. They have very low toxicity since they showed no abnormality in toxicological tests, and they have good pharmacokinetic properties.

Moreover, no notable change was observed in both the PQ interval and the QRS width in ECG. These observations suggest that the compounds have no harmful effect on the cardiac function. In addition, no notable change was observed in blood pressure. These observations suggest the compounds have no harmful effect on the circulatory system.

Therefore, the compounds of the present invention have potent antitussive effect in the animal cough model, high safety, and good pharmacokinetic properties. These compounds are expected to be excellent antitussive agents.

The compounds of the present invention can be used as antitussives for the treatment of respiratory diseases as follows; lung cancer, carcinomatous lymphopathy, rib fracture, spontaneous pneumothorax, cold syndrome (upper respiratory infection), pulmonary tuberculosis, interstitial pneumonitis, pleurisy, pneumonia, acute bronchitis, chronic bronchitis, pulmonary emphysema, pneumoconiosis, bronchiectasis, diffuse panbronchiolitis, bronchial asthma, pulmonary embolism, and pulmonary infarction. If the cough becomes worse and chronic in these diseases, it consumes energy of the respiratory muscles and physical strength to thereby prevent recovery of the underlying diseases. It is important to treat the symptoms of cough in the treatment of these diseases. Accordingly, the compounds of the present invention can be used as agents for preventing and/or treating these respiratory diseases. However, their effective use is not limited to the above.

Cough is classified as productive cough and nonproductive cough. The productive cough is caused by secreta accumulated in the respiratory tract. It stimulates the respiratory tract and the sputum is brought up. The nonproductive cough is caused by hypersensitivity in the respiratory tract. It is accompanied with cough sounding "koff koff" without sputum. It is therefore called "dry cough". The compounds of the present invention would be effective on both nonproductive and productive coughs. Specifically, they would be effective on the nonproductive cough to improve the symptoms thereof. Moreover, they would be useful to treat the respiratory diseases as above.

The medicinal products of the present invention will be administered as the pharmaceutical composition as follows.

The pharmaceutical composition of the present invention may contain at least one of the compounds represented by Formula (I), (II), or (III) of the present invention, and would be prepared by the combination with pharmaceutically acceptable additives. For details, the preferred additives include, for example, excipients such as lactose, sucrose, mannitol, crystalline cellulose, silica, corn starch, and potato starch; binders such as celluloses (hydroxypropylcellulose (HPC), hydroxypropylmethylcellulose (HPMC)), crystalline cellulose, sugars (lactose, mannitol, sucrose, sorbitol, erythritol, and xylitol), starches (corn starch, potato starch), α-starch, dextrin, polyvinylpyrrolidone (PVP), macrogol, and polyvinyl alcohol (PVA)); lubricants such as magnesium stearate, calcium stearate, talc, and carboxymethylcellulose; disintegrants such as starches (corn starch, potato starch), sodium carboxymethyl starch, carmellose, carmellose calcium, croscarmellose sodium, and crospovidone; coating agents such as celluloses (hydroxypropylcellulose (HPC), hydroxypropylmethylcellulose (HPMC)), aminoalkylmethacrylate copolymer E, and methacrylate copolymer LD; plasticizers such as triethyl citrate and macrogol; masking agents such as titanium oxide; colorants; flavoring agents; antiseptic agents such as benzalkonium chloride and para-oxybenzoate ester; isotonizing agents such as glycerin, sodium chloride, calcium chloride, mannitol, and glucose; pH adjusters such as sodium hydroxide, potassium hydroxide, sodium carbonate, hydrochloric acid, sulfuric acid, and buffers containing phosphate-buffer; stabilizers such as sugar, sugar alcohol and xanthan gum; dispersants; anti-oxidants such as ascorbic acid, butylhydroxyanisole (BHA), propyl gallate, and dl-α-tocopherol; buffering agents; preservatives such as paraben, benzyl alcohol, and benzalkonium chloride; fragrances such as vanillin, 1-menthol, and rose oil; solubilizing agents such as polyoxyethylene-hydrogenated castor oil, polysorbate 80, polyethylene glycol, phospholipid cholesterol, and triethanolamine; absorption enhancers such as sodium glycolate, disodium edetate, sodium caprylate, acylcarnitines and limonene; gelatinizers; suspension enhancers; and emulsifiers. These and any other appropriate additives and solvents may be combined with the compounds of the present invention, and the mixture may be prepared as various forms of dosages.

Examples of the dosage form are tablets, capsules, granules, powders, pills, aerosols, inhalants, ointments, patches, suppositories, injections, troches, liquids, sprits, suspension agents, extracts, and elixirs. The compounds of the present invention may be applied to the patients, for example, orally, subcutaneously, intramuscularly, nasally, percutaneously, intravenously, intraarterially, through the tissues around nerves, extradurally, intrathecally, intraventricularly, rectally, or by inhalation.

The compounds of the present invention should be applied to the adults at 0.005 mg to 3.0 g per a day, preferably at 0.05 mg to 2.5 g per a day, more preferably at 0.1 mg to 1.5 g per a day but the dose may be changed as appropriate according to the severity of the symptom, or to the administration route.

These compounds may be applied at once, or they may be divided into 2 to 6 fractions. Each divided fraction may be applied orally or non-orally. They may be also applied continuously through the infusion catheter.

Next, the present invention will be illustrated in further detail with reference to several examples below, but it should be understood that the present invention is not limited in any way to those examples.

The nuclear magnetic resonance (NMR) spectra were obtained with JEOL JNM-EX270 FT-NMR (data obtained with this machine were marked with *, JEOL Ltd.), JEOL JNM-LA300 FT-NMR (JEOL Ltd.) or JEOL JNM-AL300 FT-NMR (JEOL Ltd.). The infrared (IR) spectra were obtained with HORIBA FT-720 (HORIBA Ltd.). The melting points were measured with Mettler FP900 thermo system (METTLER TOLEDO).

Example 1

Synthesis of 4-({1-[2-(4-cyanophenyl)ethyl]-4-hydroxypiperidin-4-ylmethyl}methylamino)benzoic acid <Step 1> Synthesis of 4-cyanophenylacetaldehyde To a suspensions of methoxymethyltriphenylphosphonium chloride (392 g) in anhydrous tetrahydrofuran (1.3 L) was added dropwise a solution of potassium tert-butoxide (128 g) in anhydrous tetrahydrofuran (1.3 L) under nitrogen atmosphere at −20 to −15° C. The mixture was stirred at the same temperature for ten minutes and then at 0° C. for eighty minutes. A solution of 4-cyanobenzaldehyde (100 g) in anhydrous tetrahydrofuran (600 mL) was added dropwise to the mixture at −20 to −15° C. and stirred at the same temperature for ten minutes, and the reaction mixture was warmed to room temperature over ninety minutes. After water (1 L) was added to the reaction mixture and the mixture was stirred, sodium chloride and ether were added thereto until the mixture was separated. The organic layer was washed with brine and was dried over anhydrous sodium sulfate. The solvent was removed under reduced pressure, and a 1:1 mixture of hexane and ether (1 L) was added to the residue obtained to remove insoluble matter by filtration, and the filtrate was concentrated under reduced pressure. The residual oil was purified by silica gel column chromatography (Chromatorex NH™) (eluent; hexane:ethyl acetate=49:1 to 4:1) to yield an oil (118 g).

To a solution of the oil (115 g) in acetone (460 mL) was added 2N hydrochloric acid (230 mL) and the mixture was heated under reflux for eighty minutes under nitrogen atmosphere. After cooling, ether and sodium chloride were added to the reaction mixture to be separated, and the aqueous layer was extracted with ether. The organic layer was combined and was washed with brine until pH of the aqueous layer became about 4 and was dried over anhydrous sodium sulfate. The solvent was removed under reduced pressure to yield the titled compound (105 g) as an oil.

<Step 2> Synthesis of 1-[2-(4-cyanophenyl)ethyl]piperidin-4-one

Sodium triacetoxyborohydride (41.4 g) was added to a solution of the compound (13.2 g) obtained in Step 1 and 4-piperidone hydrochloride monohydrate (10.0 g) in methanol (500 mL) under cooling with ice-water over two and half hours, and the mixture was stirred at the same temperature for one hour. The reaction mixture was concentrated under reduced pressure, and 1N hydrochloric acid (220 mL) and dichloromethane were added to the residue and the mixture was separated, and then, the aqueous layer was washed with ethyl acetate. After adjusting pH of the aqueous layer to 9 or above with potassium carbonate, the layer was extracted with ethyl acetate. The organic layer was dried over anhydrous sodium sulfate, and the solvent was removed under reduced pressure. The residue was crystallized from 2-propanol and collected by filtration to yield the titled compound (9.07 g) as crystals.

<Step 3> Synthesis of 1-[2-(4-cyanophenyl)ethyl]piperidin-4-spiro-2'-oxirane

To anhydrous dimethylsulfoxide (42 mL) was added 60% sodium hydride (1.89 g) and the mixture was stirred at room temperature under nitrogen atmosphere for ten minutes. After gradually adding trimethylsulfoxonium iodide (10.4 g) to the mixture at 10 to 19° C., the mixture was stirred at 8 to 10° C. for thirty minutes and at room temperature for sixty minutes. A solution of the compound (9.00 g) obtained in Step 2 in anhydrous dimethylsulfoxide (42 mL) was added dropwise to the mixture at 10 to 12° C. After stirring the resulting mixture at room temperature for one and half hours, the reaction mixture was poured into an ice water (250 mL) gradually with stirring. The mixture was extracted with ethyl acetate, and the organic layer was combined and washed with water and brine successively. The organic layer was dried over anhydrous sodium sulfate, and the solvent was removed under reduced pressure. The residue was crystallized from hexane and collected by filtration to yield the titled compound (8.61 g) as crystals.

<Step 4> Synthesis of 4-({1-[2-(4-cyanophenyl)ethyl]-4-hydroxypiperidin-4-ylmethyl}methylamino)benzoic acid Scandium trifluoromethanesulfonate (609 mg) was added to a mixture of the compound (500 mg) obtained in Step 3,4-methylaminobenzoic acid (343 mg) and anhydrous acetonitrile (10 mL) under cooling with ice-water, followed by stirring at room temperature under nitrogen atmosphere for sixty and eight hours. Water (50 mL) and acetonitrile (10 mL) were added to the mixture and the pH of the reaction mixture was adjusted to 9 or above with powdered sodium hydrogen carbonate, insoluble matter was removed by filtration, and the filtrate was concentrated under reduced pressure. The residue was mixed with ethanol, water was removed by azeotropy, and the soluble matter in the residue was dissolved in water (50 mL), followed by removal of insoluble matter by filtration. The filtrate was concentrated under reduced pressure, the residue was dissolved in water (50 mL), and pH of the solution was adjusted to 7 with diluted hydrochloric acid. The precipitate was collected by filtration, and washed sequentially with water and ethyl acetate with stirring. After filtration, the precipitate was dried to yield the titled compound (524 mg) as a powder.

Example 2

Synthesis of 4-({1-[2-(4-cyanophenyl)ethyl]-4-hydroxypiperidin-4-ylmethyl}methylamino)benzoic acid The compound (26.0 g) obtained in Step 3 of Example 1 and 4-methylaminobenzoic acid (17.8 g) were dissolved in a mixture of methanol (260 mL) and water (260 mL) and the mixture was stirred at 40° C. under nitrogen atmosphere for thirteen hours, followed by removal of methanol at 40° C. or below under reduced pressure. The precipitate was collected by filtration, washed with water (200 mL) and dried. After the filtrate was left at room temperature, the precipitate was collected by filtration, washed with water (100 mL) and dried. The precipitates were combined and suspended in ethyl acetate (1.0 L), followed by vigorous stirring at room temperature for one hour. Insoluble matter was collected by filtration, sequentially washed with ethyl acetate (200 mL) and tert-butyl methyl ether (100 mL), and dried to yield the titled compound (20.3 g) as a powder. The data on physical properties of the obtained compound accord with those of the compound obtained in Example 1.

Example 3

Synthesis of 4-({1-[2-(4-cyanophenyl)ethyl]-4-hydroxypiperidin-4-ylmethyl}methylamino)-3-methylbenzoic acid <Step 1> Synthesis of methyl 4-amino-3-methylbenzoate Thionyl chloride (2.64 mL) was added to a mixture of 4-amino-3-methylbenzoic acid (5.0 g) and methanol (50 mL), followed by stirring at 80° C. for fourteen hours. After cooling to room temperature, the reaction mixture was neutralized with saturated aqueous sodium hydrogen carbonate solution, concentrated under reduced pressure and was extracted with ethyl acetate. The organic layer was sequentially washed with saturated aqueous sodium hydrogen carbonate solution and brine and was dried over anhydrous sodium sulfate. The solvent was removed under reduced pressure, to yield the titled compound (5.50 g) as crystals.

<Step 2> Synthesis of methyl 4-formylamino-3-methylbenzoate

Formic acid (4.98 mL) was added to a solution of the compound (5.50 g) obtained in Step 1 in dichloromethane (55 mL). 1-ethyl-3-(3-dimethylaminopropyl)carbodiimide hydrochloride (9.48 g) was added at 5° C. over five minutes, followed by stirring at room temperature for three hours. The reaction mixture was mixed with saturated aqueous sodium hydrogen carbonate solution (30 mL), and pH thereof was adjusted to 10 with 1 N sodium hydroxide solution, followed by separation. The aqueous layer was extracted with dichloromethane, and the combined organic layer was sequentially washed with water and brine and was dried over anhydrous sodium sulfate. The solvent was removed under reduced pressure, the residue was washed with diisopropyl ether to yield the titled compound (6.23 g) as crystals.

<Step 3> Synthesis of methyl 3-methyl-4-methylaminobenzoate

Borane-methyl sulfide complex (10 M; 9.67 mL) was gradually added to a solution of the compound (6.23 g) obtained in Step 2 in anhydrous tetrahydrofuran (65 mL) at 5° C., followed by stirring at room temperature under nitrogen atmosphere for two hours. Methanol (10 mL) was added dropwise, and a 2.5 M hydrochloric acid methanol solution (20 mL) was added, followed by heating under reflux for two hours. The solvent was removed under reduced pressure, the residue was mixed with aqueous sodium hydrogen carbonate solution (150 mL) and was extracted with ethyl acetate (150 mL×1, 50 mL×2). The combined organic layer was sequentially washed with water and brine and was dried over anhydrous sodium sulfate. The solvent was removed under reduced pressure, to yield the titled compound (5.78 g) as crystals.

<Step 4> Synthesis of 3-methyl-4-methylaminobenzoic acid

Sodium hydroxide (1.80 g) and water (0.5 mL) were added to a solution of the compound (5.78 g) obtained in Step 3 in ethanol (130 mL), followed by heating under reflux for five hours. The solvent was removed under reduced pressure, the resulting residue was dissolved in water (30 mL) and was washed with ether (50 mL). After adjusting pH to 5 to 6 with 1 N hydrochloric acid, the aqueous layer was extracted with three portions of 50 mL of ethyl acetate. The combined organic layer was washed with brine and was dried over anhydrous sodium sulfate. The solvent was removed under reduced pressure, and the residue was recrystallized from methanol. The crystals were washed with diethyl ether, and were dried to yield the titled compound (3.22 g) as crystals.

<Step 5> Synthesis of 4-({1-[2-(4-cyanophenyl)ethyl]-4-hydroxypiperidin-4-ylmethyl}methylamino)-3-methylbenzoic acid A solution of the compound (2.63 g) obtained in Step 3 of Example 1 in anhydrous acetonitrile (5.0 mL) and a suspension of the compound (1.50 g) obtained in above Step 4 in anhydrous acetonitrile (15 mL) were added dropwise to a solution of scandium trifluoromethanesulfonate (2.68 g) in anhydrous acetonitrile (5.0 mL) under cooling with ice-water under nitrogen atmosphere over fifteen minutes, followed by stirring at room temperature for two days. The reaction mixture was poured into an ice-water (25 mL), methanol (25 mL) was added to the mixture and the pH of the resulting mixture was adjusted to 7 with 1 N sodium hydroxide solution and was then adjusted to 9 or above with sodium carbonate. Viscous insoluble matter was removed by filtration, and the filtrate was concentrated under reduced pressure. The residue was suspended in a mixture of water and methanol (1:1, 25 mL), and the pH was adjusted to 9 or above with sodium carbonate, and the mixture was stirred for one hour, followed by removal of insoluble matter by filtration. The insoluble matter was treated with the same procedure, and the filtrates obtained as a result of these procedures were combined and were concentrated under reduced pressure. The residue was mixed with ethanol (12 mL), and water was removed by azeotropy. The residue was suspended in ethanol (25 mL), was stirred for one hour, and insoluble matter was removed by filtration. The filtrate was concentrated under reduced pressure, the residue was mixed with water (25 mL), was stirred, and insoluble matter was removed by filtration. After adjusting pH of the filtrate to 7 with diluted hydrochloric acid, the solvent was removed under reduced pressure. The residue was purified by silica gel column chromatography [Chromatorex NH™] (eluent: ethyl acetate:methanol=2:1 to methanol) and was further purified by silica gel column chromatography (eluent; ethyl acetate:methanol=7:1). The crystals were sequentially washed with ethyl acetate (15 mL) and tert-butyl methyl ether (15 mL), and dried to yield the titled compound (0.41 g) as crystals.

Example 4

Synthesis of 4-({1-[2-(4-cyanophenyl)ethyl]-4-hydroxypiperidin-4-ylmethyl}methylamino)-3-methoxybenzoic acid <Step 1> Synthesis of methyl 4-amino-3-methoxybenzoate The titled compound (5.37 g) was obtained in the same manner as Step 1 of Example 3, by using 4-amino-3-methoxybenzoic acid (5.00 g).

<Step 2> Synthesis of methyl 4-formylamino-3-methoxybenzoate

The titled compound (6.00 g) was obtained in the same manner as Step 2 of Example 3, by using the compound (5.37 g) obtained in above Step 1.

<Step 3> Synthesis of methyl 3-methoxy-4-methylaminobenzoate

The titled compound (5.72 g) was obtained in the same manner as Step 3 of Example 3, by using the compound (6.00 g) obtained in above Step 2.

<Step 4> Synthesis of 3-methoxy-4-methylaminobenzoic acid

The titled compound (3.02 g) was obtained in the same manner as Step 4 of Example 3, by using the compound (5.70 g) obtained in above Step 3.

<Step 5> Synthesis of 4-({1-[2-(4-cyanophenyl)ethyl]-4-hydroxypiperidin-4-ylmethyl}methylamino)-3-methoxybenzoic acid The titled compound (0.579 g) was obtained in the same manner as Step 5 of Example 3, by using the compound (1.50 g) obtained in above Step 4, and the compound (2.41 g) obtained in Step 3 of Example 1.

Example 5

Synthesis of 2-chloro-4-({1-[2-(4-cyanophenyl)ethyl]-4-hydroxypiperidin-4-ylmethyl}methylamino)benzoic acid <Step 1> Synthesis of methyl 4-amino-2-chlorobenzoate The titled compound (5.26 g) was obtained in the same manner as Step 1 of Example 3, by using 4-amino-2-chlorobenzoic acid (5.00 g).

<Step 2> Synthesis of methyl 2-chloro-4-formylaminobenzoate

The titled compound (5.15 g) was obtained in the same manner as Step 2 of Example 3, by using the compound (5.26 g) obtained in above Step 1.

<Step 3> Synthesis of methyl 2-chloro-4-methylaminobenzoate

The titled compound (4.96 g) was obtained in the same manner as Step 3 of Example 3, by using the compound (5.15 g) obtained in above Step 2.

<Step 4> Synthesis of 2-chloro-4-methylaminobenzoic acid

The titled compound (2.06 g) was obtained in the same manner as Step 4 of Example 3, by using the compound (4.96 g) obtained in above Step 3.

<Step 5> Synthesis of 2-chloro-4-({1-[2-(4-cyanophenyl)ethyl]-4-hydroxypiperidin-4-ylmethyl}methylamino)benzoic acid The titled compound (0.680 g) was obtained in the same manner as Step 5 of Example 3, by using the compound (1.50 g) obtained in above Step 4, and the compound (2.34 g) obtained in Step 3 of Example 1.

Example 6

Synthesis of 3-chloro-4-({1-[2-(4-cyanophenyl)ethyl]-4-hydroxypiperidin-4-ylmethyl}methylamino)benzoic acid <Step 1> Synthesis of methyl 3-chloro-4-formylaminobenzoate The titled compound (6.14 g) was obtained in the same manner as Step 2 of Example 3, by using methyl 4-amino-3-chlorobenzoate (5.00 g).

<Step 2> Synthesis of methyl 3-chloro-4-methylaminobenzoate

The titled compound (6.03 g) was obtained in the same manner as Step 3 of Example 3, by using the compound (6.00 g) obtained in above Step 1.

<Step 3> Synthesis of 3-chloro-4-methylaminobenzoic acid

The titled compound (2.90 g) was obtained in the same manner as Step 4 of Example 3, by using the compound (6.00 g) obtained in above Step 2.

<Step 4> Synthesis of 3-chloro-4-({1-[2-(4-cyanophenyl)ethyl]-4-hydroxypiperidin-4-ylmethyl}methylamino)benzoic acid The titled compound (302 mg) was obtained in the same manner as Step 5 of Example 3, by using the compound (500 mg) obtained in above Step 3, and the compound (590 mg) obtained in Step 3 of Example 1.

Example 7

Synthesis of 5-chloro-4-({1-[2-(4-cyanophenyl)ethyl]-4-hydroxypiperidin-4-ylmethyl}methylamino)-2-methoxybenzoic acid <Step 1> Synthesis of methyl 4-amino-5-chloro-2-methoxybenzoate The titled compound (10.5 g) was obtained as crystals in the same manner as Step 1 of Example 3, by using 4-amino-5-chloro-2-methoxybenzoic acid (10.0 g).

<Step 2> Synthesis of methyl 5-chloro-4-formylamino-2-methoxybenzoate

The titled compound (10.6 g) was obtained as crystals in the same manner as Step 2 of Example 3, by using the compound (10.5 g) obtained in above Step 1.

<Step 3> Synthesis of methyl 5-chloro-2-methoxy-4-methylaminobenzoate

The titled compound (5.32 g) was obtained as crystals in the same manner as Step 3 of Example 3, by using the compound (10.6 g) obtained in above Step 2.

<Step 4> Synthesis of 5-chloro-2-methoxy-4-methylaminobenzoic acid

The titled compound (4.14 g) was obtained as crystals in the same manner as Step 4 of Example 3, by using the compound (5.32 g) obtained in above Step 3.

<Step 5> Synthesis of 5-chloro-4-({1-[2-(4-cyanophenyl)ethyl]-4-hydroxypiperidin-4-ylmethyl}methylamino)-2-methoxybenzoic acid The titled compound (0.83 g) was obtained as a powder in the same manner as Step 5 of Example 3, by using the compound (2.00 g) obtained in above Step 4, and the compound (2.70 g) obtained in Step 3 of Example 1.

Example 8

Synthesis of tert-butyl 4-({1-[2-(4-cyanophenyl)ethyl]-3-hydroxypyrrolidin-3-ylmethyl}methylamino)benzoate <Step 1> Synthesis of 1-benzylpyrrolidine-3-spiro-2'-oxirane Trimethylsulfoxonium iodide (7.4 g) was added to a suspension of 60% sodium hydride (0.81 g) in anhydrous dimethyl sulfoxide (25 mL) at 10 to 15° C. over thirty minutes, followed by stirring at room temperature under nitrogen atmosphere for one hour. A solution of 1-benzyl-3-pyrrolidone (4.9 g) in anhydrous dimethyl sulfoxide (25 mL) was added thereto at 10 to 15° C. over twenty minutes, followed by stirring at 10 to 24° C. for one hour. Water (50 mL) and ethyl acetate (50 mL) were added thereto under cooling with ice-water, and the mixture was separated. The aqueous layer was extracted with ethyl acetate (50 mL×2) and was combined with the former organic layer. The combined organic layer was sequentially washed with water (30 mL×3) and brine (50 mL×1) and was dried over anhydrous sodium sulfate. The solvent was removed under reduced pressure, the residue was purified by silica gel column chromatography (eluent; hexane:ethyl acetate=1:1) to yield the titled compound (2.64 g) as an oil.

<Step 2> Synthesis of tert-butyl 4-methylaminobenzoate

To a mixture of 4-methylaminobenzoic acid (20.2 g) and tert-butanol (100 g) were added 1-ethyl-3-(3-dimethylaminopropyl)carbodiimide hydrochloride (25.6 g) and 4-dimethylaminopyridine (134 mg), followed by stirring at room temperature for five hours. The solvent was removed under reduced pressure, and the residue was extracted with ethyl acetate. The organic layer was sequentially washed with water, saturated aqueous sodium hydrogen carbonate solution and brine and was dried over anhydrous sodium sulfate. The solvent was removed under reduced pressure, to yield the titled compound (16.0 g) as an oil.

<Step 3> Synthesis of tert-butyl 4-[(1-benzyl-3-hydroxypyrrolidin-3-ylmethyl)methylamino]benzoate A solution of n-butyl lithium in hexane (1.57 M; 13 mL) was added dropwise to a solution of the compound (4.6 g) obtained in Step 2 in anhydrous tetrahydrofuran (15 mL) under cooling with ice-water under nitrogen atmosphere over twenty minutes, followed by stirring at the same temperature for one hour. A solution of the compound (2.6 g) obtained in Step 1 in anhydrous tetrahydrofuran (15 mL) was added dropwise under cooling with ice-water over twenty minutes, followed by stirring at room temperature overnight. Water (100 mL) was added under cooling with ice-water, and the resulting mixture was extracted with ethyl acetate (100 mL of ×1, 40 mL×2). The combined organic layer was washed with brine (50 mL), was dried over anhydrous sodium sulfate, and the solvent was removed under reduced pressure. The resulting residue was purified by silica gel column chromatography [Chromatorex NH™] (eluent; hexane:ethyl acetate=6:1) to yield the titled compound (4.42 g) as crystals.

<Step 4> Synthesis of tert-butyl 4-[(3-hydroxypyrrolidin-3-ylmethyl)methylamino]benzoate To a solution of the compound (2.0 g) obtained in Step 3 in methanol (20 mL) was added 10% palladium on carbon (0.20 g), followed by stirring at room temperature under hydrogen atmosphere for four hours. The catalyst was removed by filtration through Celite, the filtrate was concentrated under reduced pressure, and the residue was solidified by adding tert-butyl methyl ether (20 mL). The solid was dried to yield the titled compound (1.64 g) as an amorphous solid.

<Step 5> Synthesis of tert-butyl 4-({1-[2-(4-cyanophenyl)ethyl]-3-hydroxypyrrolidin-3-ylmethyl}methylamino)benzoate The compound (0.68 g) obtained in Step 4, the compound (0.64 g) obtained in Step 1 of Example 1 and acetic acid (0.50 mL) were dissolved in dichloromethane (25 mL), and sodium triacetoxyborohydride (1.88 g) was added to the solution under cooling with ice-water, followed by stirring at room temperature under nitrogen atmosphere for four hours. To the reaction mixture was added water (20 mL), and pH thereof was adjusted to 10 with 1 N sodium hydroxide solution, followed by separation. The aqueous layer was extracted with dichloromethane (20 mL×3). The combined organic layer was sequentially washed with water (30 mL) and brine (30 mL) and was dried over anhydrous sodium sulfate. The solvent was removed under reduced pressure, the residue was purified by silica gel column chromatography (eluent; ethyl acetate) to yield the titled compound (560 mg) as an amorphous solid.

Example 9

Synthesis of tert-butyl 4-({1-[2-(4-cyanophenyl)ethyl]-3-hydroxypiperidin-3-ylmethyl}methylamino)benzoate <Step 1> Synthesis of 1-benzylpiperidin-3-spiro-2'-oxirane Ground 85% potassium hydroxide (5.2 g) was added to a suspension of 1-benzyl-3-piperidone hydrochloride hydrate (5.0 g) and trimethylsulfoxonium iodide (5.3 g) in anhydrous acetonitrile (220 mL), followed by stirring at 50° C. under nitrogen atmosphere for two and half hours. After cooling to room temperature, insoluble matter was removed by filtration, and the filtrate was concentrated under reduced pressure. The residue was mixed with ethyl acetate (100 mL) and water (50 mL) and was separated. The organic layer was sequentially washed with water (50 mL) and brine (50 mL) and was dried over anhydrous sodium sulfate. The solvent was removed under reduced pressure to yield the titled compound (4.07 g) as an oil.

<Step 2> Synthesis of tert-butyl 4-[(1-benzyl-3-hydroxypiperidin-3-ylmethyl)methylamino]benzoate The titled compound (3.0 g) was obtained in the same manner as Step 3 of Example 8, by using the compound (2.0 g) obtained in above Step 1, and the compound (3.3 g) obtained in Step 2 of Example 8.

<Step 3> Synthesis of tert-butyl 4-[(3-hydroxypiperidin-3-ylmethyl)methylamino]benzoate The titled compound (1.76 g) was obtained as crystals in the same manner as Step 4 of Example 8, by using the compound (3.0 g) obtained in Step 2.

<Step 4> Synthesis of tert-butyl 4-({1-[2-(4-cyanophenyl)ethyl]-3-hydroxypiperidin-3-ylmethyl}methylamino)benzoate The titled compound (1.32 g) was obtained in the same manner as Step 5 of Example 8, by using the compound (1.0 g) obtained in above Step 3, and the compound (0.90 g) obtained in Step 1 of Example 1.

Example 10

Synthesis of methyl 4-({1-[2-(4-cyanophenyl)ethyl]-3-hydroxyazetidin-3-ylmethyl}methylamino)benzoate <Step 1> Synthesis of 1-(diphenylmethyl)azetidine-3-spiro-2'-oxirane Trimethylsulfoxonium iodide (3.58 g) and anhydrous dimethyl sulfoxide (1.15 mL) were added to a suspension of 60% sodium hydride (0.651 g) in anhydrous dimethylformamide (30 mL) under cooling with ice-water, followed by stirring at the same temperature under nitrogen atmosphere for one hour. A solution of 1-(diphenylmethyl)azetidin-3-one (3.86 g) in anhydrous dimethylformamide (30 mL) was added dropwise at −35 to −30° C. over thirty minutes, followed by stirring at the same temperature for ten minutes. The reaction mixture was warmed to 0° C. over thirty minutes and was stirred at 0 to 5° C. for thirty minutes. The reaction mixture was gradually poured into an ice water (300 mL) with stirring and was extracted with ethyl acetate (8.0 mL×3). The combined organic layer was sequentially washed with water and brine, and dried over anhydrous sodium sulfate, and the solvent was removed under reduced pressure. The residue was purified by silica gel column chromatography (eluent; ethyl acetate:hexane=1:4 to 1:3) to yield the titled compound (1.41 g) as crystals.

<Step 2> Synthesis of methyl 4-formylaminobenzoate

The titled compound (88.7 g) was obtained as crystals in the same manner as Step 2 of Example 3, by using methyl 4-aminobenzoate (90.0 g).

<Step 3> Synthesis of methyl 4-(1-diphenylmethyl-3-hydroxyazetidin-3-ylmethylamino)benzoate Anhydrous potassium carbonate (3.63 g) was added to a solution of the compound (1.20 g) obtained in above Step 1 and the compound (0.941 g) obtained in above Step 2 in acetonitrile (24 mL), followed by heating under reflux under nitrogen atmosphere for ten hours. After removing insoluble matter by filtration, the filtrate was concentrated under reduced pressure. The residue was purified by silica gel column chromatography (eluent; hexane:ethyl acetate=2:1) to yield the titled compound (1.55 g) as an amorphous solid.

<Step 4> Synthesis of methyl 4-[(1-diphenylmethyl-3-hydroxyazetidin-3-ylmethyl)methylamino]benzoate A suspension of sodium borohydride (0.718 g) and the compound (1.53 g) obtained in Step 3 in tetrahydrofuran (30.6 mL) was added to a mixture of 3 M sulfuric acid (25.3 mL) and 37% aqueous formaldehyde solution (0.566 mL) under cooling with ice-water over thirty minutes, followed by vigorous stirring at the same temperature for ninety minutes. The reaction mixture was poured into saturated aqueous sodium hydrogen carbonate solution, the solution was treated with sodium hydrogen carbonate to be adjusted to pH 9 and was extracted with ethyl acetate. The organic layer was washed with brine and dried over anhydrous sodium sulfate. The solvent was removed under reduced pressure, the residue was purified by silica gel column chromatography (eluent; hexane:ethyl acetate=2:1 to 1:1) to yield the titled compound (1.52 g) as an amorphous solid.

<Step 5> Synthesis of 4-[(3-hydroxyazetidin-3-ylmethyl)methylamino]benzoic acid monohydrochloride A solution of the compound (720 mg) obtained in Step 4 in methanol (38 mL) was treated with 10% solution of hydrogen chloride in methanol to be pH 2, and to the solution was added 10% palladium on carbon (144 mg), followed by stirring at room temperature under hydrogen atmosphere for eighteen hours. The catalyst was removed by filtration through Celite, and the filtrate was concentrated under reduced pressure. The residue was washed with hexane, was dried under reduced pressure to yield the titled compound (530 mg) as an amorphous solid.

<Step 6> Synthesis of methyl 4-({1-[2-(4-cyanophenyl)ethyl]-3-hydroxyazetidin-3-ylmethyl}methylamino)benzoate The titled compound (530 mg) was obtained as crystals in the same manner as Step 5 of Example 8, by using the compound (500 mg) obtained in above Step 5, and the compound (506 mg) obtained in Step 1 of Example 1.

Example 11

Synthesis of tert-butyl 4-[(2-{1-[2-(4-cyanophenyl)ethyl]-4-hydroxypiperidin-4-yl}ethyl)methylamino]benzoate <Step 1> Synthesis of tert-butyl 4-(acetylmethylamino)benzoate Acetic anhydride (7.66 mL) was added to a solution of the compound (15.3 g) obtained in Step 2 of Example 8 in toluene (150 mL) under cooling with water, followed by stirring at room temperature overnight. The mixture was mixed with saturated aqueous sodium hydrogen carbonate solution and was stirred for one hour. The separated toluene layer was sequentially washed with saturated aqueous sodium hydrogen carbonate solution, water and brine, and was dried over anhydrous sodium sulfate. The solvent was removed under reduced pressure, the residue was washed with hexane, and was collected by filtration to yield the titled compound (17.5 g) as crystals.

<Step 2> Synthesis of tert-butyl 4-{[2-(1-benzyl-4-hydroxypiperidin-4-yl)acetyl]methylamino}benzoate A solution of n-butyl lithium in hexane (1.57 M; 50 mL) was added dropwise to a solution of diisopropylamine (10 mL) in anhydrous tetrahydrofuran (100 mL) at −30° C. or below under nitrogen atmosphere, and the mixture was warmed to 0° C. A solution of the compound (17.5 g) obtained in Step 1 in anhydrous tetrahydrofuran (50 mL) was added dropwise at −30° C. or below, followed by stirring at the same temperature for ten minutes. A solution of 1-benzyl-4-piperidone (13 mL) in anhydrous tetrahydrofuran (50 mL) was added dropwise at −30° C. or below, followed by stirring at room temperature overnight. After adding of water, the mixture was extracted with ethyl acetate, the ethyl acetate layer was sequentially washed with water and brine and was dried over anhydrous sodium sulfate. The solvent was removed under reduced pressure, the residue was purified by silica gel column chromatography (eluent; ethyl acetate) to yield the titled compound (28.8 g).

<Step 3> Synthesis of tert-butyl 4-{[2-(1-benzyl-4-hydroxypiperidin-4-yl)ethyl]methylamino}benzoate Borane-methyl sulfide complex (10 M; 26 mL) was added to a solution of the compound (28.5 g) obtained in Step 2 in anhydrous tetrahydrofuran (100 mL) under cooling with ice-water, followed by stirring at room temperature for seven hours. After adding of methanol, the mixture was stirred for one hour and was left stand at room temperature overnight. After treating with N,N,N',N'-tetramethylethylenediamine (11 mL) with stirring for one hour, the mixture was heated under reflux for thirty minutes. The solvent was removed under reduced pressure, the residue was diluted with water and was extracted with ethyl acetate. The ethyl acetate layer was sequentially washed with water and brine and was dried over anhydrous sodium sulfate. The solvent was removed under reduced pressure, the residue was purified by silica gel column chromatography [Chromatorex NH™] (eluent; hexane:ethyl acetate=2:1), was washed with hexane to yield the titled compound (18.5 g) as crystals.

<Step 4> Synthesis of tert-butyl 4-{[2-(4-hydroxypiperidin-4-yl)ethyl]methylamino}benzoate To a solution of the compound (18.5 g) obtained in Step 3 in methanol (300 mL) was added 10% palladium on carbon (1.0 g), followed by stirring at room temperature under hydrogen atmosphere overnight. The catalyst was removed by filtration through Celite, and the filtrate was concentrated under reduced pressure. The residue was dissolved again in methanol (300 mL), was treated with 10% palladium on carbon (1.0 g) with stirring at room temperature under hydrogen atmosphere overnight. The catalyst was removed by filtration through Celite, the filtrate was concentrated under reduced pressure, the residue was crystallized from ether to yield the titled compound (14.6 g) as crystals.

<Step 5> Synthesis of tert-butyl 4-[(2-{1-[2-(4-cyanophenyl)ethyl]-4-hydroxypiperidin-4-yl}ethyl)methylamino]benzoate The compound (400 mg) obtained in Step 4, the compound (260 mg) obtained in Step 1 of Example 1 and acetic acid (0.40 mL) were dissolved in dichloromethane (8 mL), and the solution was mixed with sodium triacetoxyborohydride (1.01 g) under cooling with ice-water, followed by stirring at the same temperature under nitrogen atmosphere for sixty minutes and further stirring at room temperature for two hours. A solution of the compound (260 mg) obtained in Step 1 of Example 1 in dichloromethane (1.6 mL), and sodium triacetoxyborohydride (1.01 g) were further added under cooling with ice-water, followed by stirring at the same temperature under nitrogen atmosphere for sixty minutes and further stirring at room temperature for fifteen hours. The reaction mixture was treated with an aqueous sodium hydrogen carbonate solution to be adjusted to pH 9, was separated, and the aqueous layer was extracted with dichloromethane (10 mL×2). The combined dichloromethane layer was washed with brine and was dried over anhydrous sodium sulfate. The solvent was removed under reduced pressure, the residue was purified by silica gel column chromatography (eluent; ethyl acetate: methanol=97:3 to 9:1) to yield the titled compound (460 mg) as a gum.

Example 12

Synthesis of methyl 4-({1-[2-(4-cyanophenyl)ethyl]-4-hydroxypiperidin-4-ylmethyl}methylamino)benzoate A mixture of the compound (139 g) obtained in Step 3 of Example 1, the compound (113 g) obtained in Step 2 of Example 10, potassium carbonate (120 g) and acetonitrile (570 mL) was heated under reflux under nitrogen atmosphere for twenty three hours. Insoluble matter was removed by filtration, the filtrate was concentrated under reduced pressure to yield a crude intermediate (250 g) as an oil.

Borane-methyl sulfide complex (10 M; 148 mL) was added dropwise to a solution of the crude intermediate (250 g) in anhydrous tetrahydrofuran (2.0 L) under cooling with ice-water over thirty minutes, followed by stirring at the same temperature under nitrogen atmosphere for thirty minutes and further stirring at room temperature overnight. Methanol was gradually added to the reaction mixture under cooling with ice-water, and the mixture was treated with 10% hydrochloric acid in methanol to adjust pH to 1 or below. After stirring at room temperature for thirty minutes, the mixture was heated under reflux for two hours. The solvent was removed under reduced pressure, the residue was mixed with saturated aqueous sodium hydrogen carbonate solution (900 mL) and was treated with potassium carbonate to be adjusted to pH 10. The mixture was extracted with dichloromethane, the combined organic layer was washed with brine and dried over anhydrous sodium sulfate. The solvent was removed under reduced pressure, and the residue was purified by silica gel column chromatography [Chromatorex NH™] (eluent; hexane:dichloromethane=1:1 to 1:2). The resulting crude product was suspended in ether was collected by filtration to yield the titled compound (33.3 g) as a powder.

Example 13

Synthesis of methyl 4-{1-[2-(4-cyanophenyl)ethyl]-4-hydroxypiperidin-4-ylmethoxy}benzoate <Step 1> Synthesis of 1-benzylpiperidin-4-spiro-2'-oxirane To anhydrous dimethyl sulfoxide (400 mL) was added 60% sodium hydride (25.4 g), followed by stirring at room temperature under nitrogen atmosphere. Trimethylsulfoxonium iodide (140 g) was gradually added at 20° C. to 28° C., followed by stirring at room temperature for sixty minutes. A solution of 1-benzyl-4-piperidone (100 g) in anhydrous dimethyl sulfoxide (400 mL) was added dropwise at room temperature. After stirring at room temperature for sixty minutes, the reaction mixture was gradually poured into an ice water (2.0 L) with stirring. The mixture was extracted with ethyl acetate, and the combined organic layer was sequentially washed with four portions of water, and with brine. After drying over anhydrous sodium sulfate, the solvent was removed under reduced pressure. The residue was purified by silica gel column chromatography (eluent; ethyl acetate:hexane=1:9 to 1:1) to yield the titled compound (86.7 g) as an oil.

<Step 2> Synthesis of 1-benzyl-4-hydroxymethylpiperidin-4-ol

85% potassium hydroxide (40.6 g) was dissolved in water (615 mL) and was mixed with dioxane (103 mL). A solution of the compound (25.0 g) obtained in Step 1 in dioxane (103 mL) was added dropwise thereto at 90° C. under nitrogen atmosphere over sixty minutes, followed by stirring at the same temperature for twenty minutes. The reaction mixture was treated with concentrated hydrochloric acid under cooling with ice-water to be adjusted to pH 9, sodium chloride was added until the mixture was saturated, and the mixture was extracted with ethyl acetate. The combined organic layer was dried over anhydrous sodium sulfate, and the solvent was removed under reduced pressure. The residue was crystallized from a mixture of hexane and ether, was collected by filtration to yield the titled compound (24.6 g) as crystals.

<Step 3> Synthesis of 1-benzyl-4-(4-cyanophenoxymethyl)piperidin-4-ol

To a solution of the compound (1.66 g) obtained in Step 2 in anhydrous dimethylformamide (8 mL) was added 60% sodium hydride (0.30 g) under cooling with ice-water, followed by stirring at room temperature under nitrogen atmosphere for thirty minutes. To the mixture was added 4-fluorobenzonitrile (0.91 g), followed by stirring at room temperature for two days. The reaction mixture was poured into water (30 mL) and was extracted with ethyl acetate. The organic layer was washed with brine, and dried over anhydrous sodium sulfate, and the solvent was removed under reduced pressure. The residue was purified by silica gel column chromatography [Chromatorex NH™] (eluent; ethyl acetate:hexane=1:1) to yield the titled compound (2.2 g) as an oil.

<Step 4> Synthesis of 1-benzyl-4-(4-carboxyphenoxymethyl)piperidin-4-ol

The compound (4.27 g) obtained in Step 3 was dissolved in ethanol (38 mL), was mixed with 4 N sodium hydroxide solution (33 mL) and was heated under reflux for eight hours. The reaction mixture was concentrated to about 40 mL under reduced pressure, and the residue was mixed with 12 N hydrochloric acid (11 mL) under cooling with ice-water. The precipitated crystals were collected by filtration, were dried to yield the titled compound (3.7 g) as crystals.

<Step 5> Synthesis of 1-benzyl-4-(4-methoxycarbonylphenoxymethyl)piperidin-4-ol

The compound (0.86 g) obtained in Step 4 was dissolved in methanol (10 mL) and was mixed with a 2 M solution of trimethylsilyldiazomethane in hexane (1.3 mL). After the completion of reaction, the solvent was removed under reduced pressure, the residue was purified by silica gel column chromatography [Chromatorex NH™] (eluent; ethyl acetate:hexane=1:19 to 1:9) to yield the titled compound (0.8 g) as crystals.

<<Step 6> Synthesis of 4-(4-methoxycarbonylphenoxymethyl)piperidin-4-ol

To a solution of the compound (25 g) obtained in Step 5 in methanol (200 mL) was added 10% palladium on carbon (2.5 g), followed by stirring at room temperature under hydrogen atmosphere overnight. The catalyst was removed by filtration through Celite, the filtrate was concentrated under reduced pressure to yield the titled compound (18.7 g) as crystals.

<<Step 7> Synthesis of methyl 4-{1-[2-(4-cyanophenyl)ethyl]-4-hydroxypiperidin-4-ylmethoxy}benzoate Acetic acid (11.5 mL) was added to a solution of the compound (17.7 g) obtained in Step 6 and the compound (19.4 g) obtained in Step 1 of Example 1 in dichloromethane (450 mL) at room temperature, followed by stirring at the same temperature for thirty minutes. Sodium triacetoxyborohydride (56.6 g) was added thereto under cooling with ice-water, followed by stirring at the same temperature for thirty minutes and further stirring at room temperature for five hours. The solvent was removed under reduced pressure, the residue was mixed with water (250 mL) and ethyl acetate (250 mL), and precipitated insoluble matter was collected by filtration (16.1 g). The insoluble matter (13.0 g) was mixed with water (50 mL) and saturated aqueous sodium hydrogen carbonate solution (150 mL) and was extracted with ethyl acetate. The organic layer was washed with brine, and dried over anhydrous sodium sulfate, and the solvent was removed under reduced pressure. The residue was crystallized from a mixture of ether and hexane to yield the titled compound (10.3 g) as crystals.

Example 14

Synthesis of 4-({1-[2-(4-cyanophenyl)ethyl]-3-hydroxypyrrolidin-3-ylmethyl}methylamino)benzoic acid The compound (1.00 g) obtained in Example 8 was dissolved in 6 N hydrochloric acid (2.5 mL), followed by stirring at room temperature overnight. The mixture was treated with sodium carbonate to be adjusted to pH 7, the precipitate was collected by filtration, was washed with water, and was dried to yield the titled compound (0.355 g).

Example 15

Synthesis of 4-({1-[2-(4-cyanophenyl)ethyl]-3-hydroxypiperidin-3-ylmethyl}methylamino)benzoic acid The titled compound (0.80 g) was obtained in the same manner as Example 14, by using the compound (1.26 g) obtained in Example 9.

Example 16

Synthesis of 4-[(2-{1-[2-(4-cyanophenyl)ethyl]-4-hydroxypiperidin-4-yl}ethyl)methylamino]benzoic acid The titled compound (368 mg) was obtained in the same manner as Example 14, by using the compound (430 mg) obtained in Example 11.

Example 17

Synthesis of 4-({1-[2-(4-cyanophenyl)ethyl]-3-hydroxyazetidin-3-ylmethyl}methylamino)benzoic acid To a solution of the compound (500 mg) obtained in Example 10 in anhydrous tetrahydrofuran (20 mL) was added 90% potassium trimethylsilanolate (470 mg) under cooling with ice-water, followed by stirring at the same temperature for twenty minutes and further stirring at room temperature for fifty four hours. The reaction mixture was mixed with brine (30 mL) under cooling with ice-water and the solution was washed with ethyl acetate. The ethyl acetate layer was extracted with brine, and the latter aqueous layer was combined with the former one. The combined aqueous layer was treated with diluted hydrochloric acid to be adjusted to pH 7, the resulting precipitate was collected by filtration and washed with water. The filtrate was treated with diluted hydrochloric acid to be adjusted to pH 5, the resulting precipitate was collected by filtration and was washed with water. The combined precipitate was stirred in methanol (2 mL), collected by filtration and dried to yield the titled compound (163 mg) as crystals.

Example 18

Synthesis of 4-{1-[2-(4-cyanophenyl)ethyl]-4-hydroxypiperidin-4-ylmethoxy}benzoic acid To a solution of n-octanethiol (2.04 g) in a mixture of anhydrous tetrahydrofuran (10 mL) and anhydrous hexamethylphosphoric triamide (HMPA) (5 mL), a 1.59 M solution of n-butyl lithium in hexane (8.74 mL) was added dropwise under cooling with ice-water under nitrogen atmosphere. After stirring at the same temperature for fifteen minutes, a solution of the compound (2.50 g) obtained in Example 13 in a mixture of anhydrous tetrahydrofuran (10 mL) and anhydrous HMPA (5 mL) was added dropwise thereto over ten minutes, followed by stirring at the same temperature for thirty minutes and further stirring at room temperature for seventeen hours. After the completion of reaction, the reaction mixture was mixed with an ice water (20 mL) under cooling with ice-water and was washed with ethyl acetate (25 mL×2). Small portions of 3 N hydrochloric acid were gradually added to the aqueous layer with stirring under cooling with ice-water, to adjust the pH of the mixture to 5.6. The precipitated crystals were collected by filtration and were sequentially washed with water and ethanol. The resulting crystals were suspended in a mixture of methanol (50 mL) and water (10 mL), followed by heating under reflux for thirty minutes. After standing to cool, the crystals were collected by filtration and were washed with methanol, and dried under reduced pressure to yield the titled compound (1.83 g) as crystals.

Example 19

Synthesis of methyl 4-{1-[2-(4-cyanophenyl)ethyl]-4-hydroxypiperidin-4-ylmethoxy}benzoate A mixture of the compound (0.24 g) obtained in Step 3 of Example 1 and methyl 4-hydroxybenzoate (0.15 g) was heated with stirring at 100° C. under nitrogen atmosphere for three hours. After cooling, the solidified residue was purified by silica gel column chromatography [Chromatorex NH™] (eluent; ethyl acetate:hexane=1:9 to 3:17) to yield the titled compound (0.074 g) as crystals. The data on physical properties of the resulting compound accord with those of the compound obtained in Example 13.

Example 20

Synthesis of methyl 4-{[1-(4-cyanobenzyl)-4-hydroxypiperidin-4-ylmethyl]methylamino}benzoate <<Step 1> Synthesis of methyl 4-[(1-benzyl-4-hydroxypiperidin-4-ylmethyl)methylamino]benzoate Potassium carbonate (92.0 g) was added to a solution of the compound (90.0 g) obtained in Step 1 of Example 13 and the compound (79.3 g) obtained in Step 2 of Example 10 in anhydrous acetonitrile (300 mL), followed by heating under reflux under nitrogen atmosphere for thirty hours. After cooling, the reaction mixture was filtrated through Celite, the filtrate was concentrated under reduced pressure to yield a crude intermediate (164 g) as an oil.

Borane-methyl sulfide complex (10 M; 83.7 mL) was added dropwise to a solution of the crude intermediate (164 g) in tetrahydrofuran (120 mL) under cooling with ice-water under nitrogen atmosphere over twenty minutes, followed by stirring at room temperature for three hours. Methanol (400 mL) was gradually added to the reaction mixture under cooling with ice-water, and the mixture was treated with a 2.5 M solution of hydrogen chloride in methanol (400 mL) to adjust the pH of the mixture to 1 or below, followed by heating under reflux for two hours. The solvent was removed under reduced pressure, the residue was mixed with ethyl acetate (2 L) and saturated aqueous sodium hydrogen carbonate solution (1 L) and was treated with a 1 N aqueous sodium hydroxide solution to be adjusted to pH 10, followed by separation. The aqueous layer was extracted with ethyl acetate, the combined ethyl acetate layer was sequentially washed with water and brine and was dried over anhydrous sodium sulfate. The solvent was removed under reduced pressure, the residue was purified by silica gel column chromatography (eluent; ethyl acetate:methanol=20:1 to 10:1) to yield crude crystals (125 g). The crude crystals were further purified by silica gel column chromatography [Chromatorex NH™] (eluent; hexane:ethyl acetate:tetrahydrofuran=4:4:1) to yield the titled compound (67.7 g) as crystals.

<<Step 2> Synthesis of methyl 4-[(4-hydroxypiperidin-4-ylmethyl)methylamino]benzoate To methanol (480 mL) was added 10% palladium on carbon (3.9 g), followed by stirring at room temperature under hydrogen atmosphere for one hour. A solution of the compound (67.7 g) obtained in Step 1 in methanol (200 mL) was added thereto, followed by stirring at room temperature under hydrogen atmosphere for thirty hours. The catalyst was removed by filtration through Celite, the filtrate was concentrated under reduced pressure to yield an oil (58.6 g). The oil was crystallized from ether, and the crystals were collected by filtration, and dried under reduced pressure to yield the titled compound (51.6 g) as crystals.

<<Step 3> Synthesis of methyl 4-{[1-(4-cyanobenzyl)-4-hydroxypiperidin-4-ylmethyl]methylamino}benzoate Acetic acid (1.45 mL) was added to a solution of the compound (2.12 g) obtained in Step 2 and 4-cyanobenzaldehyde (2.00 g) in dichloromethane (67 mL) at room temperature, followed by stirring for thirty minutes. Sodium triacetoxyborohydride (6.47 g) was gradually added thereto at the same temperature. After stirring at room temperature under nitrogen atmosphere for two hours, the reaction mixture was gradually added to saturated aqueous sodium hydrogen carbonate solution (30 mL). After separation, the aqueous layer was treated with 1 M aqueous sodium hydroxide solution to be adjusted to pH 10 and was extracted with dichloromethane (20 mL×2). The combined organic layer was washed with brine and was dried over anhydrous sodium sulfate. The solvent was removed under reduced pressure, the residue was purified by silica gel column chromatography [Chromatorex NH™] (eluent; ethyl acetate) to yield the titled compound (2.53 g) as a white powder.

Example 21

Synthesis of methyl 4-({1-[3-(4-cyanophenyl)propyl]-4-hydroxypiperidin-4-ylmethyl}methylamino) benzoate <<Step 1> Synthesis of methyl 4-({1-[3-(4-cyanophenyl)propionyl]-4-hydroxypiperidin-4-ylmethyl}methylamino) benzoate To a suspension of the compound (3.62 g) obtained in Step 2 of Example 20 and 3-(4-cyanophenyl)propionic acid (2.50 g) in dichloromethane (50 mL) was added 1-ethyl-3-(3-dimethylaminopropyl)carbodiimide hydrochloride (2.74 g), followed by stirring at room temperature overnight under nitrogen atmosphere. The reaction mixture was added to 0.5 M hydrochloric acid (30 mL) and was further mixed with dichloromethane (50 mL), followed by separation. The aqueous layer was extracted with dichloromethane, the combined organic layer was washed with brine and was dried over anhydrous sodium sulfate. The solvent was removed under reduced pressure, the residue was purified by silica gel column chromatography (eluent; ethyl acetate) to yield the titled compound (3.66 g) as a white powder.

<<Step 2> Synthesis of methyl 4-({1-[3-(4-cyanophenyl)propyl]-4-hydroxypiperidin-4-ylmethyl}methylamino)benzoate The titled compound (1.98 g) was obtained in the same manner as Step 3 of Example 3, by using the compound (2.94 g) obtained in Step 1.

Example 22

Synthesis of methyl 4-({1-[2-(4-cyanophenoxy)ethyl]-4-hydroxypiperidin-4-ylmethyl}methylamino) benzoate <<Step 1> Synthesis of methyl 4-({1-[2-(4-cyanophenoxy)acetyl]-4-hydroxypiperidin-4-ylmethyl}methylamino) benzoate To a suspension of lithium 2-(4-cyanophenoxy)acetate in dichloromethane (28 mL) was added 1.0 M solution of hydrogen chloride in ether (14.8 mL). The compound (3.73 g) obtained in Step 2 of Example 20, 1-ethyl-3-(3-dimethylaminopropyl)carbodiimide hydrochloride (2.83 g) and dimethylformamide (14 mL) were added thereto, followed by stirring at room temperature overnight under nitrogen atmosphere. The reaction mixture was mixed with water (50 mL) and was separated. The aqueous layer was extracted with dichloromethane, the combined organic layer was washed with 0.5 N hydrochloric acid and brine and was dried over anhydrous sodium sulfate. After the solvent was removed under reduced pressure, the residue was solidified with ether and collected by filtration to yield the titled compound (2.71 g).

<<Step 2>> Synthesis of methyl 4-({1-[2-(4-cyanophenoxy)ethyl]-4-hydroxypiperidin-4-ylmethyl}methylamino)benzoate The titled compound (1.40 g) was obtained in the same manner as Step 3 of Example 3, by using the compound (2.59 g) obtained in Step 1.

Example 23

Synthesis of 4-({1-[2-(4-cyanophenyl)ethyl]-4-hydroxypiperidin-4-ylmethyl}methylamino)-N-(tetrahydropyran-2-yloxy)benzamide A solution of O-(tetrahydro-2H-pyran-2-yl)hydroxylamine (0.36 g) in anhydrous dimethylformamide (5 mL) was added dropwise to a solution of the compound (0.80 g) obtained in Example 1, 1-ethyl-3-(3-dimethylaminopropyl)carbodiimide hydrochloride (0.47 g) and 1-hydroxybenzotriazole monohydrate (0.39 g) in anhydrous dimethylformamide (20 mL) under cooling with ice-water under nitrogen atmosphere, followed by stirring at the same temperature for twenty minutes and further stirring at room temperature for two days. After adding water, the mixture was treated with saturated aqueous sodium hydrogen carbonate solution to be adjusted to pH 8 and was extracted with ethyl acetate. The combined organic layer was sequentially washed with water and brine, and dried over anhydrous sodium sulfate. The solvent was removed under reduced pressure, the residue was purified by silica gel column chromatography (eluent; ethyl acetate:methanol=4:1), was crystallized from ether to yield the titled compound (620 mg) as crystals.

Example 24

Synthesis of methyl 4-({4-hydroxy-1-[2-(4-trifluoromethylphenyl)ethyl]piperidin-4-ylmethyl}methylamino)benzoate <<Step 1>> Synthesis of methyl 4-({4-hydroxy-1-[2-(4-trifluoromethylphenyl)acetyl]piperidin-4-ylmethyl}methylamino)benzoate The titled compound (1.93 g) was obtained in the same manner as Step 1 of Example 21, by using the compound (1.20 g) obtained in Step 2 of Example 20 and 4-trifluoromethylphenylacetic acid (0.97 g).

<<Step 2>> Synthesis of methyl 4-({4-hydroxy-1-[2-(4-trifluoromethylphenyl)ethyl]piperidin-4-ylmethyl}methylamino)benzoate The titled compound (1.39 g) was obtained as crystals in the same manner as Step 3 of Example 3, by using the compound (1.91 g) obtained in Step 1.

Example 25

Synthesis of methyl 4-({1-[2-(4-cyanophenyl)ethyl]-4-methoxypiperidin-4-ylmethyl}methylamino)benzoate To the compound (6.0 g) obtained in Example 12 in DMF (50 mL) was added 60% sodium hydride (0.65 g) under cooling with ice-water, followed by stirring at the same temperature for one hour. The reaction mixture was cooled to −40° C., and iodomethane (2.09 g) was added dropwise thereto over twenty minutes. After stirring at −40° C. for one hour and further stirring at −20 to −15° C. for four hours, the reaction mixture was left at −12° C. overnight. The reaction mixture was cooled to −20° C., was mixed with an ice water (100 mL) and was warmed to room temperature. After extracting with ethyl acetate, the organic layer was sequentially washed with water and brine, and dried over anhydrous sodium sulfate. The solvent was removed under reduced pressure, the residue was purified by silica gel column chromatography [Chromatorex NH™] (eluent; hexane:ethyl acetate=3:1 to 1:1) to yield the titled compound (0.643 g) as a white solid.

Example 26

Synthesis of 4-({1-[2-(4-cyanophenyl)ethyl]-4-hydroxypiperidin-4-ylmethyl}methylamino)benzoic acid monohydrochloride The compound (22.0 g) obtained in Example 1 was suspended in a mixture of ethanol (264 mL) and water (176 mL). The mixture was heated under reflux and was completely dissolved by adding 1 N hydrochloric acid (58.7 mL) dropwise while keeping the mixture under reflux. After cooling to room temperature, the precipitated crystals were collected by filtration. The crystals were sequentially washed with 2-propanol (50 mL×3) and tert-butyl methyl ether (50 mL×3), dried under reduced pressure to yield the titled compound (21.1 g) as crystals. Elementary analysis revealed that the compound is monohydrate.

| Elementary analysis: as $C_{23}H_{28}ClN_3O_3$—$H_2O$ | | | |
|---|---|---|---|
| Calculated: | C: 61.67, | H: 6.75, | N: 9.38 |
| Found: | C: 61.64, | H: 6.83, | N: 9.21 |

X-ray powder diffraction (2θ [degree]): 6.20, 15.16, 15.92, 18.52, 19.20, 21.72, 22.36, 25.00, 26.16, 29.04, 31.40

The following compounds were obtained in the same manner as Example 26.

Example 27

3-Chloro-4-({1-[2-(4-cyanophenyl)ethyl]-4-hydroxypiperidin-4-ylmethyl}methylamino)benzoic acid monohydrochloride

Example 28

5-Chloro-4-({1-[2-(4-cyanophenyl)ethyl]-4-hydroxypiperidin-4-ylmethyl}methylamino)-2-methoxybenzoic acid monohydrochloride

Example 29

4-({1-[2-(4-Cyanophenyl)ethyl]-3-hydroxypyrrolidin-3-ylmethyl}methylamino)benzoic acid monohydrochloride

Example 30

4-({1-[2-(4-Cyanophenyl)ethyl]-3-hydroxypiperidin-3-ylmethyl}methylamino)benzoic acid monohydrochloride

Example 31

4-[(2-{1-[2-(4-Cyanophenyl)ethyl]-4-hydroxypiperidin-4-yl}ethyl)methylamino)benzoic acid monohydrochloride

Example 32

Synthesis of 4-({1-[2-(4-cyanophenyl)ethyl]-4-hydroxypiperidin-4-ylmethyl}methylamino)-3-methylbenzoic acid monohydrochloride The compound (310 mg) obtained in Example 3 was suspended in water (15 mL) and was dissolved therein by addition of 1 N hydrochloric acid (3.0 mL) with heating under reflux. After cooling, the solvent was removed under reduced pressure, the residue was pulverized, was dried under reduced pressure to yield the titled compound (274 mg) as a powder.

Example 33

Synthesis of 2-chloro-4-({1-[2-(4-cyanophenyl)ethyl]-4-hydroxypiperidin-4-ylmethyl}methylamino)benzoic acid monohydrochloride The compound (105 mg) obtained in Example 5 was suspended in water (6.0 mL) and dissolved by addition of 1 N hydrochloric acid (516 μL) with heating under reflux. After cooling, the reaction mixture was left under refrigeration overnight, the precipitated crystals were collected by filtration, and dried to yield the titled compound (83.5 mg) as a powder.

The following compound was obtained in the same manner as Example 33.

Example 34

4-({1-[2-(4-Cyanophenyl)ethyl]-3-hydroxyazetidin-3-ylmethyl}methylamino)benzoic acid monohydrochloride

Example 35

Synthesis of 4-({4-hydroxy-1-[2-(4-trifluoromethylphenyl)ethyl]piperidin-4-ylmethyl}methylamino) benzoic acid monohydrochloride To a solution of the compound (1.18 g) obtained in Example 24 in methanol (30 mL) was added 2 N sodium hydroxide solution (5.3 mL), followed by heating under reflux for three hours. The solvent was removed under reduced pressure, and the residue was mixed with ether and water, followed by separation. The aqueous layer was washed with ether, the residual aqueous layer was treated with 3 N hydrochloric acid to be adjusted to pH 5 to 7, followed by stirring at 5° C. for thirty minutes. The precipitate was collected by filtration, washed with water and dried under reduced pressure to yield crystals (1.23 g). The crystals (1.19 g) was dissolved in a mixture of 2 N sodium hydroxide solution (6.0 mL) and water (20 mL), was cooled to 5° C. and was treated with 3 N hydrochloric acid to be adjusted to pH 3 to 4, followed by stirring at the same temperature for thirty minutes. The precipitate was collected by filtration, washed with water, and dried under reduced pressure to yield the titled compound (1.13 g) as crystals.

Example 36

Synthesis of 4-{1-[2-(4-cyanophenyl)ethyl]-4-hydroxypiperidin-4-ylmethoxy}benzoic acid monohydrochloride To a solution of the compound (200 mg) obtained in Example 19 in methanol (10 mL) was added 2 N sodium hydroxide solution (0.25 mL), followed by heating under reflux for five hours. The solvent was removed under reduced pressure, the residue was dissolved in a small portion of water, and the aqueous layer was washed with ethyl acetate. The residual aqueous layer was treated with diluted hydrochloric acid to be adjusted to pH 3, the precipitate was collected by filtration to yield the titled compound (69 mg) as crystals.

Example 37

Synthesis of 4-({1-[2-(4-cyanophenyl)ethyl]-4-hydroxypiperidin-4-ylmethyl}methylamino)-N-hydroxybenzamide monohydrochloride To a solution of the compound (0.60 g) obtained in Example 23 in methanol (20 mL) was added 10% hydrogen chloride in methanol (5.0 mL), followed by stirring. The solvent was removed under reduced pressure, the residue was dissolved in methanol, and the solvent was removed again under reduced pressure. The residue was solidified with ethyl acetate, the resulting solid was finely powdered and was collected by filtration. The powder was dissolved in water (60 mL), and the solvent was removed under reduced pressure.

Example 38

Synthesis of 4-{[1-(4-cyanobenzyl)-4-hydroxypiperidin-4-ylmethyl]methylamino}benzoic acid monohydrochloride To a solution of the compound (2.00 g) obtained in Example 20 in anhydrous tetrahydrofuran (50 mL) was added 90% potassium trimethylsilanolate (1.63 g) under cooling with ice-water, followed by stirring at the same temperature under nitrogen atmosphere for thirty minutes and further stirring at room temperature for five days. The solvent was removed under reduced pressure, the residue was mixed with ethyl acetate, was stirred, and insoluble matter was collected by filtration. The insoluble matter was dissolved in a mixture of ethanol (25.4 mL) and water (17 mL) and was treated with 1 N hydrochloric acid (25.4 mL) with heating under reflux to be adjusted to pH 1. After cooling, the mixture was held in refrigeration overnight. The precipitate was collected by filtration, was sequentially washed with 2-propanol and tert-butyl methyl ether, and dried under reduced pressure to yield the titled compound (1.47 g) as a powder.

The following compounds were obtained in the same manner as Example 38.

Example 39

4-({1-[3-(4-Cyanophenyl)propyl]-4-hydroxypiperidin-4-ylmethyl}methylamino)benzoic acid monohydrochloride

Example 40

4-({1-[2-(4-Cyanophenoxy)ethyl]-4-hydroxypiperidin-4-ylmethyl}methylamino)benzoic acid monohydrochloride

Example 41

4-({1-[2-(4-Cyanophenyl)ethyl]-4-methoxypiperidin-4-ylmethyl}methylamino)benzoic acid monohydrochloride

Example 42

Synthesis of methyl 4-{1-[2-(4-cyanophenyl)ethyl]-4-hydroxypiperidin-4-ylmethylthio}benzoate Thionyl chloride (3.7 mL) was added to a suspension of 4-mercaptobenzoic acid (5.14 g) in methanol (30 mL) under cooling with ice, followed by heating under reflux for ten hours. After cooling, the precipitated crystals were collected by filtration, washed with methanol, and dried to yield a crystalline product (3.70 g). A mixture of the resulting crystals (0.17 g), the compound (0.24 g) obtained in Step 3 of Example 1, anhydrous potassium carbonate (0.70 g) and anhydrous dimethylformamide (1.0 mL) was stirred at 100 to 110° C. under nitrogen atmosphere for twenty hours. The reaction mixture was poured into an ice water (10 mL) and was extracted with ethyl acetate. The combined organic layer was washed with brine and was dried over anhydrous sodium sulfate. The solvent was removed under reduced pressure, the residue was purified by silica gel column chromatography [Chromatorex NH™] (eluent; hexane:ethyl acetate=1:1) to yield the titled compound (0.25 g) as crystals.

Example 43

Synthesis of sodium 4-{1-[2-(4-cyanophenyl)ethyl]-4-hydroxypiperidin-4-ylmethylthio}benzoate The compound (248 mg) obtained in Example 42 was suspended in a 50% mixture of methanol and water (10 mL) and was further mixed with 2 N sodium hydroxide solution (0.3 mL), followed by heating under reflux for ten hours. The solvent was removed under reduced pressure, and the residue was crystallized from ethyl acetate. The crystals were collected by filtration, and dried to yield the titled compound (200 mg) as crystals.

Example 44

Synthesis of methyl 4-{1-[2-(4-cyanophenyl)ethyl]-4-hydroxypiperidin-4-ylmethylsulfinyl}benzoate Sodium metaperiodate (235 mg) was added to a solution of the compound (411 mg) obtained in Example 42 in a mixture of methanol (10 mL) and water (2 mL) under cooling with ice-water, followed by stirring at room temperature for one hour. Another portion of sodium metaperiodate (64 mg) was added, followed by stirring at room temperature for two hours. The reaction mixture was mixed with 10% aqueous potassium carbonate solution (10 mL) and ethyl acetate (20 mL), was stirred, and insoluble matter was removed by filtration. The filtrate was separated, and the aqueous layer was extracted with ethyl acetate. The combined organic layer was washed with brine and was dried over anhydrous sodium sulfate. The solvent was removed under reduced pressure, the residue was purified by silica gel column chromatography [Chromatorex NH™] (eluent; hexane:ethyl acetate=3:1 to ethyl acetate) to yield the titled compound (180 mg) as crystals.

Example 45

Synthesis of 4-{1-[2-(4-cyanophenyl)ethyl]-4-hydroxypiperidin-4-ylmethylsulfinyl}benzoic acid hydrochloride To a solution of the compound (150 mg) obtained in Example 44 in a mixture of anhydrous tetrahydrofuran (8 mL) and anhydrous dichloromethane (8 mL) was added 90% potassium trimethylsilanolate (125 mg) at room temperature, followed by stirring at the same temperature under nitrogen atmosphere for four hours. Insoluble matter was collected by filtration, was washed with dichloromethane and was dried. The insoluble matter was dissolved in water (1 mL) and was then treated with 1 N hydrochloric acid to adjust the pH of the mixture to 5 to 5.6. The precipitate was collected by filtration, washed with water and dried. The precipitate was suspended in methanol, and mixed with 10% solution of hydrogen chloride in methanol, then the mixture was stirred at room temperature, and the solvent was removed under reduced pressure. The residue was suspended in acetonitrile, washed at 40 to 50° C. with stirring for one hour, was collected by filtration, and dried under reduced pressure to yield the titled compound (58 mg) as crystals.

The residue was finely powdered and dried under reduced pressure to yield the titled compound (447 mg) as a powder.

Example 46

Synthesis of methyl 4-{1-[2-(4-cyanophenyl)ethyl]-4-hydroxypiperidin-4-ylmethylsulfonyl}benzoate <Step 1> Synthesis of methyl 4-[1-(tert-butoxycarbonyl)-4-hydroxypiperidin-4-ylmethylthio]benzoate Dimethylformamide (ten drops) was added to a suspension of 4-mercaptobenzoic acid (5.0 g) in methanol (32 mL), followed by dropwise addition of thionyl chloride (3.5 mL) under cooling with ice-water. The mixture was stirred at room temperature for five minutes and was heated under reflux for two hours. Insoluble matter was collected by filtration, washed with methanol, and dried to yield crystals (4.50 g). Anhydrous potassium carbonate (4.34 g) was added to a solution of the crystals (2.00 g) and 1-(tert-butoxycarbonyl)piperidine-4-spiro-2'-oxirane (2.23 g) in 4-methyl-2-pentanone (26 mL), followed by heating under reflux under nitrogen atmosphere for nine hours. The reaction mixture was mixed with an ice water (50 mL) and was extracted with ethyl acetate. The organic layer was sequentially washed with water and brine and was dried over anhydrous sodium sulfate. The solvent was removed under reduced pressure, the residue was purified by silica gel column chromatography [Chromatorex NH™] (eluent; hexane:ethyl acetate=19:1 to 1:1), and crystallized from a 5:1 mixture of hexane and ether to yield the titled compound (2.55 g) as crystals.

<<Step 2> Synthesis of methyl 4-[1-(tert-butoxycarbonyl)-4-hydroxypiperidin-4-ylmethylsulfonyl]benzoate To a solution of the compound (2.5 g) obtained in Step 1 in dichloromethane (25 mL) was gradually added 70% m-chloroperbenzoic acid (4.0 g) at −10° C., followed by stirring at the same temperature for thirty minutes. Aqueous potassium iodide solution was added thereto under cooling with ice-water, and aqueous saturated sodium thiosulfate solution was added until the color of iodide disappeared. Dichloromethane (70 mL) and 10% aqueous potassium carbonate solution (50 mL) were added, followed by separation. The aqueous layer was extracted with dichloromethane, and the extract was combined with the former organic layer. The combined organic layer was sequentially washed with water and brine and was dried over anhydrous sodium sulfate. The solvent was removed under reduced pressure, and the residue was crystallized from ether. The crystals were washed with a 1:1 mixture of hexane and ether (30 mL), and dried to yield the titled compound (2.00 g) as crystals.

<<Step 3> Synthesis of methyl 4-(4-hydroxypiperidin-4-ylmethylsulfonyl)benzoate hydrochloride A 3 M solution of hydrogen chloride in ethyl acetate (8.0 mL) was added dropwise to a suspension of the compound (1.95 g) obtained in Step 2 in ethyl acetate (8.0 mL) under cooling with ice-water, followed by stirring at the same temperature for ten minutes and further stirring at room temperature for two hours. The solvent was removed under reduced pressure, the residue was washed with ethyl acetate, was collected by filtration, and dried to yield the titled compound (1.60 g) as crystals.

<<Step 4> Synthesis of methyl 4-{1-[2-(4-cyanophenyl)ethyl]-4-hydroxypiperidin-4-ylmethylsulfonyl}benzoate A mixture of the compound (800 mg) obtained in above Step 3, the compound (665 mg) obtained in Step 1 of Example 1, and dichloromethane (15 mL) was stirred at room temperature for thirty minutes, and sodium triacetoxyborohydride (1940 mg) was added thereto, followed by stirring at the same temperature for one hour and further stirring at room temperature overnight. To the mixture was added 1 N hydrochloric acid (20 mL) under cooling with ice-water, and the mixture was stirred, and the aqueous layer was separated. The organic layer was concentrated under reduced pressure, the residue was mixed with ether and 1 N hydrochloric acid, the mixture was separated, and the resulting aqueous layer was combined with former one. The combined aqueous layer was washed again with ether and was treated with potassium carbonate to be adjusted to pH 9 or above. After extracting with dichloromethane, the organic layer was washed with brine and was dried over anhydrous sodium sulfate. The solvent was removed under reduced pressure, the residue was crystallized from ether, and collected by filtration to yield the titled compound (568 mg) as crystals.

Example 47

Synthesis of sodium 4-{1-[2-(4-cyanophenyl)ethyl]-4-hydroxypiperidin-4-ylmethylsulfonyl}benzoate To a solution of the compound (70 mg) obtained in Example 46 in methanol (2.0 mL) was added 2 N aqueous sodium hydroxide solution (0.080 mL), followed by stirring at room temperature for three days. The solvent was removed under reduced pressure, the residue was mixed with ethyl acetate (4 mL) and was stirred for one hour. Insoluble matter was collected by filtration, and dried to yield the titled compound (56 mg) as crystals.

Example 48

Synthesis of 4-({1-[2-(4-cyanophenyl)ethyl]-4-hydroxypiperidin-4-ylmethyl}methylamino)benzoic acid monomethanesulfonate Methanesulfonic acid (1.42 mL) was added to a suspension of the compound (7.2 g) obtained in Example 1 in water (50 mL), was heated with stirring until the compound was dissolved, followed by cooling to room temperature with stirring. The crystals were collected by filtration and were recrystallized from water (50 mL). The resulting crystals were collected by filtration, washed with acetone, and dried under reduced pressure to yield the titled compound (7.6 g) as crystals.

Example 49

Synthesis of 4-({1-[2-(4-cyanophenyl)ethyl]-4-hydroxypiperidin-4-ylmethyl}methylamino)benzoic acid monohydrochloride A suspension of the compound (2.00 g) obtained in Example 26 in 2-propanol (40 mL) was heated under reflux under nitrogen atmosphere for eight hours, followed by standing overnight. The crystals were collected by filtration, washed with 2-propanol (5 mL×3) and tert-butyl methyl ether (5 mL×2), and dried under reduced pressure to yield the titled compound (1.85 g) as crystals. Elementary analysis revealed that the compound is anhydride.

| Elementary analysis: as $C_{23}H_{28}ClN_3O_3$ | | | |
|---|---|---|---|
| Calculated: | C: 64.25, | H: 6.56, | N: 9.77 |
| Found: | C: 64.18, | H: 6.60, | N: 9.61 |

X-ray powder diffraction (2θ [degree]): 7.96, 11.96, 15.96, 17.80, 18.12, 19.48, 24.52, 25.08, 26.80, 30.36

IR (KBr, cm$^{-1}$): 2229, 1657, 1604, 1523, 1381, 1261, 1097, 960

Example 50

Synthesis of 4-({1-[2-(4-cyanophenyl)ethyl]-4-hydroxypiperidin-4-ylmethyl}methylamino)benzoic acid The compound (2.00 g) obtained in Step 3 of Example 1 and 4-methylaminobenzoic acid (1.37 g) were dissolved in a mixture of acetone (8 mL) and water (32 mL), followed by stirring at room temperature for three days. The precipitate was collected by filtration, washed with water (40 mL) and dried. The resulting powder was suspended in ethyl acetate (40 mL), stirred at room temperature for two hours, then the precipitate was collected by filtration, washed with ethyl acetate (20 mL), and dried to yield the titled compound (2.37 g) as a powder. The data on physical properties of the compound accord with those of the compound obtained in Example 1.

The data on physical properties of the compounds of Examples 1 to 48, and those of intermediates for the compounds are shown in Table 2 and Table 3, respectively. In Table 3, the "Example Number 1-1" means the compound obtained in Step 1 of Example 1.

TABLE 2

| Example No. | IR (cm$^{-1}$) | NMR (ppm) (no mark: 300MHz, *: 270MHz) | m.p. (°C.) |
|---|---|---|---|
| 1 | KBr: 3211, 2231, 1606, 1572, 1520, 1383, 787 | CD$_3$OD*: 7.81(2H, d, J=9Hz), 7.66 (2H, d, J=8Hz), 7.45(2H, d, J=9Hz), 6.80(2H, d, J=9Hz), 3.47(2H, s), 3.13-2.70(8H, m), 3.11(3H, s), 1.95-1.80(2H, m), 1.77-1.66(2H, m) | 220.0 (dec.) |
| 3 | KBr: 2229, 1603, 1543, 1408, 1358, 798 | DMSO-d$_6$*: 7.7-7.6(4H, m), 7.40 (2H, d, J=8Hz), 7.12(1H, d, J=8Hz), 4.14(1H, brs), 3.08(2H, s), 2.82(3H, s), 2.8-2.7(2H, m), 2.5-2.4 (4H, m), 2.4-2.2(2H, m), 2.28(3H, s), 1.5-1.3(4H, m) | 103.6-108.7 |
| 4 | KBr: 2227, 1599, 1547, 1414, 1242, 1119, 795 | CD$_3$OD: 7.63(2H, d, J=8Hz), 7.55(1H, d, J=2Hz), 7.51(1H, dd, J=8, 2Hz), 7.40(2H, d, J=8Hz), 7.01(1H, d, J=8Hz), 3.89(3H, s), 3.27(2H, s), 2.97(3H, s), 2.9-2.8(2H, m), 2.7-2.5(4H, m), 2.5-2.4(2H, m), 1.7-1.5(4H, m) | 252.6 (dec.) |
| 5 | KBr: 2227, 1601, 1510, 1367, 1030 | DMSO-d$_6$: 7.8-7.7(3H, m), 7.44(2H, m, J=8Hz), 6.8-6.7(2H, m), 4.36(1H, s), 3.35(2H, s), 3.02(3H, s), 2.9-2.8(2H, m), 2.7-2.6(2H, m), 2.6-2.5(2H, m), 2.3-2.2(2H, m), 1.6-1.4(4H, m) | 186.2-189.6 |
| 6 | KBr: 2227, 1595, 1541, 1506, 1371, 1244 | DMSO-d$_6$*: 7.8-7.7(4H, m), 7.40 (2H, d, J=8Hz), 7.27(1H, d, J=9Hz), 4.22(1H, brs), 3.30(2H, s), 2.99(3H, s), 2.9-2.7(2H, m), 2.6-2.2 (6H, m), 1.5-1.3(4H, m) | 110.7-112.4 |
| 7 | KBr: 2227, 1597, 1396, 1358, 1227, 1126, 984 | DMSO-d$_6$*: 7.70(2H, d, J=8Hz), 7.58(2H, d, J=8Hz), 7.40(2H, d, J=8Hz), 6.79(1H, s), 4.22(1H, brs), 3.80(3H, s), 3.31(2H, s), 2.99(3H, s), 2.8-2.7(2H, m), 2.6-2.2(6H, m), 1.5-1.4(4H, m) | 226.8-228.3 |
| 8 | KBr: 2227, 1697, 1604, 1523, 1298, 1161, 1113, 771 | CDCl$_3$*: 7.83(2H, d, J=9Hz), 7.58(2H, d, J=8Hz), 7.30(2H, d, J=8Hz), 6.76(2H, d, J=9Hz), 3.6-3.5 (2H, m), 3.09(3H, s), 3.0-2.5(8H, m), 2.0-1.8(2H, m), 1.57(9H, s) | amorphous |
| 9 | KBr: 2227, 1695, 1604, 1523, 1294, 1163, 1113 | CDCl$_3$: 7.84(2H, d, J=9Hz), 7.56(2H, d, J=8Hz), 7.25(2H, d, J=8Hz), 6.72(2H, d, J=9Hz), 3.42(2H, s), 3.12(1H, brs), 3.08(3H, s), 2.8-2.7(3H, m), 2.7-2.5 (3H, m), 2.1-2.0(2H, m), 1.8-1.7(1H, m), 1.6-1.5(2H, m), 1.57(9H, s), 1.4-1.2(1H, m) | 41.2-44.1 |
| 10 | KBr: 2225, 1695, 1604, 1523, 1288, 1186 | CDCl$_3$*: 7.88(2H, d, J=9Hz), 7.58(2H, d, J=8Hz), 7.29(2H, d, J=8Hz), 6.81(2H, d, J=9Hz), 3.87(3H, s), 3.70(3H, s), 3.42(2H, d, J=9Hz), 3.09(3H, s), 2.93(2H, d, J=9Hz), 2.72(4H, s) | 145.5-149.1 |
| 11 | KBr: 2227, 1695, 1604, 1523, 1296, 1163, 1113 | CDCl$_3$: 7.85(2H, d, J=9Hz), 7.58(2H, d, J=8Hz), 7.31(2H, d, J=8Hz), 6.65(2H, d, J=9Hz), 3.6-3.5 (2H, m), 2.99(3H, s), 2.9-2.8(2H, m), 2.8-2.6(4H, m), 2.5-2.3(2H, m), 1.8-1.6(6H, m), 1.57(9H, s) | amorphous |
| 12 | KBr: 2225, 1693, 1608, 1523, 1294, 1194 | CDCl$_3$: 7.89(2H, d, J=9Hz), 7.58(2H, d, J=8Hz), 7.31(2H, d, J=8Hz), 6.82(2H, d, J=9Hz), 3.86(3H, s), 3.42(2H, s), 3.11(3H, s), 2.91-2.74(4H, m), 2.68-2.59(2H, m), 2.45-2.33(2H, m), 1.83-1.65(4H, m), 1.50(1H, s) | 140.5-142.2 |
| 13 | KBr: 2225, 1711, 1606, 1282, 1259, 1167, | CDCl$_3$: 8.00(2H, d, J=9Hz), 7.58(2H, d, J=8Hz), 7.32(2H, d, J=8Hz), 6.93(2H, d, J=9Hz), 3.89(3H, s), 3.88(3H, s), 2.94-2.85 (2H, m), 2.82-2.73(2H, m), 2.70-2.62(2H, m), 2.51(2H, ddd, J=11, 10, 4Hz), 2.11(1H, brs), 1.88-1.72(4H, m) | 118.6-120.6 |
| 14 | KBr: 2227, 1687, 1603, 1523, 1381, 1184 | CD$_3$OD: 7.86(2H, d, J=9Hz), 7.70(2H, d, J=8Hz), 7.47(2H, d, J=8Hz), 6.85(2H, d, J=9Hz), 3.8-3.6 (3H, m), 3.6-3.3(5H, m), 3.2-3.0(2H, m), 3.13(3H, s), 2.3-2.0(2H, m) | 106.1-130.8 |
| 15 | KBr: 2227, 1687, 1603, 1525, 1381, 1190 | CD$_3$OD*: 7.83(2H, d, J=9Hz), 7.64(2H, d, J=8Hz), 7.42(2H, d, J=8Hz), 6.84(2H, d, J=9Hz), 3.59(1H, d, J=15Hz), 3.46(1H, d, J=15Hz), 3.3-2.8(8H, m), 3.09(3H, s), 2.2-2.0(1H, m), 1.8-1.6(3H, m) | 166.9-181.3 |
| 16 | KBr: 2227, 1672, 1603, 1531, 1373, 1184 | CD$_3$OD*: 7.84(2H, d, J=9Hz), 7.73(2H, d, J=8Hz), 7.52(2H, d, J=8Hz), 6.73(2H, d, J=9Hz), 3.7-3.6 (2H, m), 3.5-3.3(6H, m), 3.2-3.1(2H, m), 3.03(3H, s), 2.0-1.9(4H, m), 1.9-1.8(2H, m) | 146.8-148.4 |
| 17 | KBr: 2227, 1604, 1523, 1369, 1198, 785 | DMSO-d$_6$*: 7.8-7.6(4H, m), 7.44 (2H, d, J=8Hz), 6.77(2H, d, J=9Hz), 5.54(1H, s), 3.59(2H, s), 3.4-3.2(4H, m), 3.02(3H, s), 2.8-2.6(4H, m) | 197.9-199.4 |
| 18 | KBr: 3309, 2229, 1604, 1543, 1363, 1246 | DMSO-d$_6$*: 7.88(2H, d, J=9Hz), 7.74(2H, d, J=8Hz), 7.45(2H, d, J=8Hz), 7.02(2H, d, J=9Hz), 4.55(1H, brs), 3.82(2H, s), 2.88-2.80 (2H, m), 2.69-2.33(6H, m), 1.73-1.50(4H, m) | 208.4 (dec.) |
| 20 | KBr: 2229, 1709, 1606, 1522, 1286, 1186 | CDCl$_3$: 7.88(2H, d, J=9Hz), 7.60(2H, d, J=8Hz), 7.45(2H, d, J=8Hz), 6.82(2H, d, J=9Hz), 3.85(3H, s), 3.56(2H, s), 3.41(2H, s), 3.09(3H, s), 2.7-2.6(2H, m), 2.4-2.3(2H, m), 1.8-1.7(2H, m), 1.7-1.6(2H, m) | 127.5-137.1 |
| 21 | KBr: 2229, 1705, 1606, | CDCl$_3$: 7.88(2H, d, J=9Hz), 7.57(2H, d, J=8Hz), 7.29(2H, d, | 126.8-129.7 |

TABLE 2-continued

| Example No. | IR (cm$^{-1}$) | NMR (ppm) (no mark: 300MHz, *: 270MHz) | m.p. (° C.) |
|---|---|---|---|
| | 1523, 1284, 1186 | J=8Hz), 6.82(2H, d, J=9Hz), 3.86(3H, s), 3.41(2H, s), 3.10(3H, s), 2.8-2.7(4H, m), 2.4-2.3(2H, m), 2.3-2.2(2H, m), 1.9-1.6(6H, m) | |
| 22 | KBr: 2222, 1689, 1608, 1525, 1286, 1190 | CDCl$_3$*: 7.88(2H, d, J=9Hz), 7.58(2H, d, J=9Hz), 6.95(2H, d, J=9Hz), 6.82(2H, d, J=9Hz), 4.14(2H, t, J=6Hz), 3.86(3H, s), 3.41(2H, s), 3.10(3H, s), 2.9-2.8(2H, m), 2.85(2H, t, J=6Hz), 2.5-2.4(2H, m), 1.9-1.6(4H, m) | 112.5-113.0 |
| 23 | KBr: 2229, 1608, 1510, 1308, 1211 | CDCl$_3$: 8.67(1H, s), 7.64(2H, d, J=9Hz), 7.58(2H, d, J=8Hz), 7.31(2H, d, J=8Hz), 6.82(2H, d, J=9Hz), 5.05(1H, m), 4.1-4.0(1H, m), 3.7-3.6(1H, m), 3.40(2H, s), 3.09(3H, s), 3.0-2.6(6H, m), 2.5-2.3(2H, m), 2.0-1.5(10H, m) | 100.9-102.1 |
| 24 | KBr: 1693, 1606, 1529, 1439, 1327, 1294, 1182, 1117 | CDCl$_3$: 7.88(2H, d, J=9Hz), 7.54(2H, d, J=8Hz), 7.31(2H, d, J=8Hz), 6.82(2H, d, J=9Hz), 3.85(3H, s), 3.42(2H, s), 3.11(3H, s), 2.9-2.8(4H, m), 2.7-2.6(2H, m), 2.4-2.3(2H, m), 1.8-1.6(4H, m) | 142.7-143.9 |
| 25 | KBr: 2224, 1689, 1612, 1523, 1290, 1194, 1072 | CDCl$_3$: 7.87(2H, d, J=9Hz), 7.57(2H, d, J=8Hz), 7.29(2H, d, J=8Hz), 6.71(2H, d, J=9Hz), 3.85(3H, s), 3.46(2H, s), 3.29(3H, s), 3.06(3H, s), 2.9-2.8(2H, m), 2.8-2.7(2H, m), 2.6-2.5(2H, m), 2.3-2.2(2H, m), 1.9-1.8(2H, m), 1.7-1.6(2H, m) | 126.9-134.5 |
| 26 | KBr: 3151, 2225, 1660, 1601, 1385, 1194 | CD$_3$OD*: 7.85(2H, d, J=9Hz), 7.72(2H, d, J=8Hz), 7.50(2H, d, J=8Hz), 6.86(2H, d, J=9Hz), 3.59-3.26(6H, m), 3.56(2H, s), 3.22-3.10(2H, m), 3.15(3H, s), 2.08-1.82(4H, m) | 146.1-148.9 |
| 27 | KBr: 2227, 1714, 1597, 1375, 1213, 1111 | CD$_3$OD*: 7.96(1H, d, J=2Hz), 7.88(1H, dd, J=8, 2Hz), 7.71(2H, d, J=8Hz), 7.49(2H, d, J=8Hz), 7.35(1H, d, J=8Hz), 3.5-3.2(6H, m), 3.41(2H, s), 3.2-3.1(2H, m), 3.04(3H, s), 2.0-1.8(4H, m) | 254.2-258.9 |
| 28 | KBr: 2231, 1687, 1599, 1371, 1211, 1105, 978 | DMSO-d$_6$: 12.48(1H, brs), 9.76(1H, brs), 7.83(2H, d, J=8Hz), 7.64(1H, s), 7.49(2H, d, J=8Hz), 6.86(1H, s), 4.91(1H, s), 3.85(3H, s), 3.4-3.0 (10H, m), 3.03(3H, s), 1.8-1.6 (4H, m) | 116.3-120.8 |
| 29 | KBr: 2229, 1687, 1603, 1525, 1383, 1186 | CD$_3$OD: 7.87(2H, d, J=9Hz), 7.71(2H, d, J=8Hz), 7.47(2H, d, J=8Hz), 6.85(2H, d, J=9Hz), 3.9-3.8 (1H, m), 3.8-3.7(2H, m), 3.6-3.1(7H, m), 3.13(3H, s), 2.4-2.3(1H, m), 2.2-2.1(1H, m) | 122.8-132.5 |
| 30 | KBr: 2229, 1687, 1603, 1525, 1381, 1190 | CD$_3$OD: 7.86(2H, d, J=9Hz), 7.68(2H, d, J=8Hz), 7.44(2H, d, J=8Hz), 6.86(2H, d, J=9Hz), 3.7-3.4 (3H, m), 3.4-3.3(3H, m) 3.2-2.9(4H, m), 3.13(3H, s), 3.2-3.1(1H, m), 1.9-1.8(2H, m), 1.8-1.7(1H, m) | 220.1-233.3 |
| 31 | KBr: 2227, 1672, 1603, 1531, 1373, 1184 | CD$_3$OD*: 7.84(2H, d, J=9Hz), 7.73(2H, d, J=8Hz), 7.52(2H, d, J=8Hz), 6.73(2H, d, J=9Hz), 3.7-3.6 (2H, m), 3.6-3.3(6H, m), 3.2-3.1(2H, m), 3.03(3H, s), 2.0-1.9(4H, m), 1.9-1.8(2H, m) | 231.3-236.4 |
| 32 | KBr: 2227, 1714, 1608, 1460, 1421, 1207, 1130 | DMSO-d$_6$: 10.50(1H, brs), 7.83(2H, d, J=8Hz), 7.7-7.6(2H, m), 7.49(2H, d, J=8Hz), 7.20(1H, d, J=8Hz), 3.4-3.0(10H, m), 2.84(3H, s), 2.34(3H, s), 1.9-1.8(2H, m), 1.7-1.6(2H, m) | 127.1-132.7 |
| 33 | KBr: 2225, 1668, 1593, 1387, 1248, 1032 | DMSO-d$_6$: 12.43(1H, brs), 9.94(1H, brs), 7.83(2H, d, J=8Hz), 7.75(1H, d, J=9Hz), 7.50(2H, d, J=8Hz), 6.9-6.7(2H, m), 5.05(1H, s), 3.5-3.3 (4H, m), 3.48(2H, s), 3.2-3.0(4H, m), 3.05(3H, m), 2.0-1.8(2H, m), 1.8-1.7(2H, m) | 145.2-148.0 |
| 34 | KBr: 2229, 1666, 1601, 1525, 1190 | CD$_3$OD*: 7.89(2H, d, J=9Hz), 7.69(2H, d, J=8Hz), 7.45(2H, d, J=8Hz), 6.86(2H, d, J=9Hz), 4.3-4.1 (2H, m), 4.0-3.9(2H, m), 3.70(2H, s), 3.6-3.4(2H, m), 3.14(3H, s), 3.0-2.9(2H, m) | 209.1-210.5 |
| 35 | KBr: 1672, 1603, 1525, 1329, 1188, 1113 | CD$_3$OD: 7.85(2H, d, J=9Hz), 7.65(2H, d, J=8Hz), 7.51(2H, d, J=8Hz), 6.86(2H, d, J=9Hz), 3.6-3.5 (2H, m), 3.56(2H, s), 3.4-3.3(4H, m), 3.2-3.1(2H, m), 3.15(3H, m), 2.1-1.8(4H, m) | 235.1-246.9 |
| 36 | KBr: 2935, 2227, 1707, 1606, 1257, 1165 | CD$_3$OD: 7.99(2H, d, J=9Hz), 7.73(2H, d, J=8Hz), 7.53(2H, d, J=8Hz), 7.04(2H, d, J=9Hz), 3.99(2H, s), 3.63-3.53(2H, m), 3.50-3.36(4H, m), 3.25-3.16(2H, m), 2.21-2.07(2H, m), 2.05-1.95(2H, m) | 239.5-242.2 |
| 37 | KBr: 2229, 1608, 1514, 1383, 1209, 1147 | DMSO-d$_6$*: 10.85(1H, s), 10.09(1H, brs), 8.71(1H, s), 7.82(2H, d, J=8Hz), 7.61(2H, d, J=8Hz), 7.50(2H, d, J=8Hz), 6.77(2H, d, J=9Hz), 5.01(1H, s), 3.5-3.0(10H, m), 3.03(3H, m), 2.0-1.8(2H, m), 1.8-1.6(2H, m) | 191.3-193.9 |
| 38 | KBr: 2231, 1610, 1523, 1279, 1190, 773 | CD$_3$OD*: 7.9-7.8(4H, m), 7.72(2H, d, J=8Hz), 6.84(2H, d, J=9Hz), 4.42(2H, s), 3.54(2H, s), 3.4-3.3(4H, m), 3.12(3H, s), 1.9-1.8(4H, m) | 153.1-157.7 |
| 39 | KBr: 2227, 1664, 1597, 1525, 1383, 1192 | CD$_3$OD*: 7.84(2H, d, J=9Hz), 7.68(2H, d, J=8Hz), 7.44(2H, d, J=8Hz), 6.85(2H, d, J=9Hz), 3.54(2H, s), 3.5-3.4(2H, m), 3.4-3.1(4H, m), 3.13(3H, s), 2.8-2.7(2H, m), 2.1-1.8(6H, m) | 150.1-151.2 |
| 40 | KBr: 2233, 1657, 1606, 1525, 1257, 1178 | CD$_3$OD: 7.84(2H, d, J=9Hz), 7.71(2H, d, J=8Hz), 7.16(2H, d, J=9Hz), 6.85(2H, d, J=9Hz), 4.5-4.4 (2H, m), 3.6-3.3(6H, m), 3.55(2H, s), 3.14(3H, s), 2.1-1.8(4H, m) | 258.4-260.1 |
| 41 | KBr: 2225, 1678, 1603, 1523, 1381, 1188 | CD$_3$OD*: 7.86(2H, d, J=9Hz), 7.71(2H, d, J=8Hz), 7.49(2H, d, J=8Hz), 6.84(2H, d, J=9Hz), 3.67(2H, s), 3.5-3.3(4H, m), 3.38(3H, s), 3.2-3.1(4H, m), 3.10(3H, s), 2.2-2.0(2H, m), 2.0-1.8(2H, m) | 226.3-230.7 |
| 42 | KBr: 2225, 1707, 1593, 1290, 1186, 1111, 762 | CDCl$_3$: 7.93(2H, d, J=9Hz), 7.57(2H, d, J=9Hz), 7.41(2H, d, J=9Hz), 7.30(2H, d, J=8Hz), 3.90(3H, s), 3.17(3H, s), 2.9-2.8(2H, m), 2.8-2.7(2H, m), 2.7-2.6(2H, m), 2.5-2.4(2H, m), 1.8-1.7(4H, m) | 119.1-120.8 |
| 43 | KBr: 2227, 1585, 1541, 1415, 769 | CD$_3$OD: 7.85(2H, d, J=9Hz), 7.64(2H, d, J=8Hz), 7.41(2H, d, J=8Hz), 7.35(2H, d, J=9Hz), 3.15(2H, s), 2.9-2.8(2H, m), 2.8-2.7 (2H, m), 2.7-2.6(2H, m), 2.6-2.4(2H, m), 1.9-1.6(4H, m) | 256.2 (dec.) |
| 44 | KBr: 2229, 1720, 1277, 1117, 1005 | CDCl$_3$: 8.21(2H, d, J=8Hz), 7.73(2H, d, J=8Hz), 7.58(2H, d, J=8Hz), 7.31(2H, d, J=8Hz), 3.96(3H, s), 3.78(3H, s), 3.05(1H, d, J=13Hz), 2.9-2.7(4H, m), 2.7-2.5 (5H, m), 2.3-2.1(1H, m), 2.0-1.9(1H, m), 1.8-1.6(2H, m) | 169.6-174.5 |

TABLE 2-continued

| Example No. | IR (cm⁻¹) | NMR (ppm) (no mark: 300MHz, *: 270MHz) | m.p. (°C.) |
|---|---|---|---|
| 45 | KBr: 2224, 1714, 1398, 1234, 1011 | CD$_3$OD*: 8.23(2H, d, J=8Hz), 7.81(2H, d, J=8Hz), 7.73(2H, d, J=8Hz), 7.52(2H, d, J=8Hz), 3.6-3.0 (10H, m), 2.4-2.3(1H, m), 2.2-1.9(3H, m) | 279.7 (dec.) |
| 46 | KBr: 2231, 1728, 1279, 1115, 760 | CDCl$_3$*: 8.24(2H, d, J=8Hz), 8.01(2H, d, J=8Hz), 7.57(2H, d, J=8Hz), 7.30(2H, d, J=8Hz), 3.98(3H, s), 3.31(2H, s), 2.9-2.8(2H, m), 2.7-2.6(4H, m), 2.6-2.4(2H, m), 2.0-1.9(2H, m), 1.8-1.7(2H, m) | 135.4-137.2 |
| 47 | KBr: 2229, 1606, 1562, 1404, 1296, 1149 | CD$_3$OD*: 8.11(2H, d, J=9Hz), 7.93(2H, d, J=9Hz), 7.64(2H, d, J=8Hz), 7.42(2H, d, J=8Hz), 3.44(2H, s), 2.9-2.8(2H, m), 2.7-2.6(2H, m), 2.6-2.4(2H, m), 1.9-1.8(4H, m) | 223.5 (dec.) |
| 48 | KBr: 2227, 1662, 1604, 1525, 1190, 1036, 777 | CD$_3$OD*: 7.85(2H, d, J=9Hz), 7.72(2H, d, J=8Hz), 7.50(2H, d, J=8Hz), 6.86(2H, d, J=9Hz), 3.6-3.1 (8H, m), 3.56(2H, s), 3.15(3H, s), 2.70(3H, s), 2.0-1.8(4H, m) | 128.9-132.1 |

TABLE 3

| Example No. | IR (cm⁻¹) | NMR (ppm) (no mark: 300MHz, *: 270MHz) | m.p. (°C.) |
|---|---|---|---|
| 1-1 | — | CDCl$_3$: 9.80(1H, t, J=2Hz), 7.67(2H, d, J=8Hz), 7.34(2H, d, J=8Hz), 3.82(2H, d, J=2Hz) | — |
| 1-2 | — | CDCl$_3$: 7.60(2H, d, J=8Hz), 7.34(2H, d, J=8Hz), 2.90(2H, dd, J=9, 6Hz), 2.82(4H, t, J=6Hz), 2.74(2H, dd, J=9, 6Hz), 2.47(4H, t, J=6Hz) | 79.0-79.8 |
| 1-3 | — | CDCl$_3$: 7.58(2H, d, J=8Hz), 7.32(2H, d, J=8Hz), 2.88(2H, dd, J=9, 6Hz), 2.75-2.57(6H, m), 2.68(2H, s), 1.89(2H, ddd, J=13, 9, 4Hz), 1.55(1H, ddd, J=13, 5, 4Hz) | 74.2-75.1 |
| 3-1 | — | CDCl$_3$: 7.8-7.7(2H, m), 6.64(1H, d, J=8Hz), 4.00(2H, brs), 3.85(3H, s), 2.18(3H, s) | — |
| 3-2 | — | CDCl$_3$: 8.74(0.5H, d, J=11Hz), 8.6-8.5(0.5H, m), 8.23(0.5H, d, J=9Hz), 8.0-7.9(2H, m), 7.5-7.3(0.5H, m), 7.23(0.5H, d, J=9Hz), 7.2-7.1(0.5H, m), 3.91(1.5H, s), 3.90(1.5H, s), 2.34(1.5H, s), 2.33(1.5H, s) | — |
| 3-3 | — | CDCl$_3$: 7.86(1H, dd, J=9, 2Hz), 7.8-7.7(1H, m), 6.56(1H, d, J=9Hz), 4.1-4.0(1H, m), 3.85(3H, s), 2.95(3H, d, J=5Hz), 2.14(3H, s) | — |
| 3-4 | — | DMSO-d$_6$: 7.7-7.6(1H, m), 7.6-7.5(1H, m), 6.47(1H, d, J=9Hz), 5.8-5.7(1H, m), 2.78(3H, d, J=5Hz), 2.08(3H, s) | — |
| 4-1 | — | CDCl$_3$: 7.55(1H, dd, J=8, 2Hz), 7.45(1H, d, J=2Hz), 6.66(1H, d, J=8Hz), 4.22(2H, brs), 3.90(3H, s), 3.86(3H, s) | — |
| 4-2 | — | CDCl$_3$: 8.88(0.2H, d, J=12Hz), 8.51(0.8H, d, J=2Hz), 8.45(0.8H, d, J=8Hz), 8.0-7.9(0.8H, m), 7.9-7.8(0.2H, m), 7.7-7.6(0.2H, m), 7.69(0.8H, dd, J=8, 2Hz), 7.6-7.5(0.2H, m), 7.57(0.8H, d, J=2Hz), 7.3-7.2(0.2H, m), 3.96(2.4H, s), 3.95(0.6H, s), 3.91(3H, s) | — |
| 4-3 | — | CDCl$_3$: 7.66(1H, dd, J=8, 2Hz), 7.40(1H, d, J=2Hz), 6.52(1H, d, J=8Hz), 4.8-4.7(1H, m), 3.89(3H, s), 3.86(3H, s), 2.92(3H, d, J=5Hz) | — |
| 4-4 | — | DMSO-d$_6$: 7.47(1H, dd, J=8, 2Hz), 7.26(1H, d, J=2Hz), 6.46(1H, d, J=8Hz), 5.9-5.8(1H, m), 3.81(3H, s), 2.75(3H, d, J=5Hz) | — |
| 5-1 | — | DMSO-d$_6$: 7.64(1H, d, J=9Hz), 6.62(1H, d, J=2Hz), 6.50(1H, d, J=9, 2Hz), 6.19(2H, s), 3.73(3H, s) | — |
| 5-2 | — | CDCl$_3$: 8.83(0.3H, d, J=11Hz), 8.45(0.7H, d, J=1Hz), 8.0-7.9(0.3H, m), 7.91(0.7H, d, J=9Hz), 7.77(0.7H, d, J=2Hz), 7.52(0.7H, dd, J=9, 2Hz), 7.2-7.1(0.3H, m), 7.1-7.0(0.3H, m), 3.95(0.9H, s), 3.94(2.1H, s) | — |
| 5-3 | — | CDCl$_3$: 7.80(1H, d, J=9Hz), 6.59(1H, d, J=2Hz), 6.44(1H, dd, J=9, 2Hz), 4.2-4.1(1H, m), 3.86(3H, s), 2.87(3H, d, J=5Hz) | — |
| 5-4 | — | DMSO-d$_6$: 7.69(1H, d, J=9Hz), 6.7-6.6(1H, m), 6.55(1H, d, J=2Hz), 6.49(1H, dd, J=9, 2Hz), 2.71(3H, d, J=5Hz) | — |
| 6-1 | — | CDCl$_3$: 8.9-8.8(0.2H, m), 8.6-8.5(0.8H, m), 8.56(0.8H, d, J=9Hz), 8.2-8.1(0.2H, m), 8.09(0.8H, d, J=2Hz), 8.0-7.9(0.2H, m), 7.96(0.8H, d, J=9, 2Hz), 7.9-7.8(0.8H, m), 7.4-7.3(0.2H, m), 3.92(3H, s) | — |
| 6-2 | — | CDCl$_3$: 7.94(1H, d, J=2Hz), 7.86(1H, dd, J=9, 2Hz), 6.61(1H, d, J=9Hz), 4.9-4.8(1H, m), 3.86(3H, s), 2.96(3H, d, J=5Hz) | — |
| 6-3 | — | DMSO-d$_6$: 7.8-7.7(2H, m), 6.66(1H, d, J=9Hz), 6.3-6.2(1H, m), 2.81(3H, d, J=5Hz) | — |
| 7-1 | — | DMSO-d$_6$: 7.59(1H, s), 6.44(1H, s), 6.15(2H, s), 3.72(3H, s), 3.68(3H, s) | — |
| 7-2 | — | DMSO-d$_6$: 10.10(1H, s), 8.49(1H, s), 8.05(1H, brs), 7.77(1H, s), 3.81(3H, s), 3.77(3H, s) | — |
| 7-3 | — | DMSO-d$_6$: 7.62(1H, s), 6.3-6.2(1H, m), 6.19(1H, s), 3.83(3H, s), 3.69(3H, s), 2.84(3H, d, J=5Hz) | — |
| 7-4 | — | DMSO-d$_6$: 7.61(1H, s), 6.3-6.2(1H, m), 6.18(1H, s), 3.83(3H, s), 2.84(3H, d, J=5Hz) | — |
| 8-1 | — | CDCl$_3$*: 7.4-7.2(5H, m), 3.65(1H, d, J=13Hz), 3.64(1H, d, J=13Hz), 2.9-2.7(3H, m), 2.79(1H, d, J=11Hz), 2.7-2.6(1H, m), 2.59(1H, d, J=11Hz), 2.3-2.1(1H, m), 2.0-1.8(1H, m) | — |
| 8-2 | — | CDCl$_3$: 7.83(2H, d, J=9Hz), 6.54(2H, d, J=9Hz), 4.12(1H, brs), 2.88(3H, d, J=5Hz), 1.57(9H, s) | — |
| 8-3 | — | CDCl$_3$: 7.83(2H, d, J=9Hz), 7.3-7.2(5H, m), 6.76(2H, d, J=9Hz), 3.63(2H, s), 3.6-3.5(2H, m), 3.07(3H, s), 2.9-2.8(1H, m), 2.6-2.5(3H, m), 2.40(1H, s), 2.0-1.8(2H, m) | — |
| 8-4 | — | CDCl$_3$: 7.86(2H, d, J=9Hz), 6.81(2H, d, J=9Hz), 3.66(1H, d, J=15Hz), 3.56(1H, d, J=15Hz), 3.2-3.1(1H, m), 3.08(3H, s), 3.0-2.9(2H, m), 2.82(2H, d, J=11Hz), 1.9-1.7(2H, m), 1.57(9H, s) | — |
| 9-1 | — | CDCl$_3$*: 7.4-7.2(5H, m), 3.56(1H, d, J=13Hz), 3.53(1H, d, J=13Hz), | |

TABLE 3-continued

| Example No. | IR (cm⁻¹) | NMR (ppm) (no mark: 300MHz, *: 270MHz) | m.p. (° C.) |
|---|---|---|---|
|  | — | 2.7-2.6(2H, m), 2.5-2.3(4H, m), 2.0-1.8(1H, m), 1.8-1.6(1H, m), 1.6-1.5(2H, m) | — |
| 9-2 | — | CDCl$_3$*: 7.83(2H, d, J=9Hz), 7.4-7.2(5H, m), 6.72(2H, d, J=9Hz), 3.6-3.4(2H, m), 3.43(2H, s), 3.31(1H, brs), 3.06(3H, s), 2.8-2.7(1H, m), 2.6-2.5(1H, m), 2.2-2.1(1H, m), 2.0-1.9(1H, m), 1.8-1.2(4H, m), 1.57(9H, s) | — |
| 9-3 | — | CDCl$_3$: 7.84(2H, d, J=9Hz), 6.74(2H, d, J=9Hz), 3.5-3.4(2H, m), 3.10(3H, s), 3.0-2.9(1H, m), 2.8-2.7(1H, m), 2.6-2.5(2H, m), 1.8-1.3(4H, m), 1.56(9H, s) | — |
| 10-1 | — | CDCl$_3$: 7.5-7.4(4H, m), 7.3-7.2(6H, m), 4.50(1H, s), 3.57(2H, d, J=10Hz), 3.42(2H, d, J=10Hz), 2.83(2H, s) | — |
| 10-2 | — | CDCl$_3$: 8.84(0.4H, d, J=11Hz), 8.44(0.6H, d, J=1Hz), 8.05(0.8H, d, J=9Hz), 8.03(1.2H, d, J=9Hz), 7.98-7.88(0.4H, m), 7.64(1.2H, d, J=9Hz), 7.39(0.6H, brs), 7.13(0.8H, m), 3.92(1.2H, s), 3.91(1.8H, s) | — |
| 10-3 | — | CDCl$_3$*: 7.89(2H, d, J=9Hz), 7.5-7.4(4H, m), 7.3-7.1(6H, m), 6.65(2H, d, J=9Hz), 4.72(1H, t, J=6Hz), 4.39(1H, s), 3.86(3H, s), 3.53(2H, d, J=6Hz), 3.39(2H, d, J=9Hz), 2.96(2H, d, J=9Hz), 2.18(1H, s) | — |
| 10-4 | — | CDCl$_3$*: 7.92(2H, d, J=9Hz), 7.5-7.4(4H, m), 7.3-7.1(6H, m), 6.88(2H, d, J=9Hz), 4.33(1H, s), 3.87(3H, s), 3.79(2H, s), 3.33(2H, d, J=9Hz), 3.09(3H, s), 2.89(2H, d, J=9Hz), 2.18(1H, s) | — |
| 10-5 | — | CD$_3$OD*: 7.96(2H, d, J=9Hz), 7.12(2H, d, J=9Hz), 4.07(2H, d, J=12Hz), 3.9-3.8(2H, m), 3.86(3H, s), 3.83(2H, s), 3.21(3H, s) | — |
| 11-1 | — | CDCl$_3$*: 8.04(2H, d, J=8Hz), 7.25(2H, d, J=8Hz), 3.29(3H, s), 1.92(3H, s), 1.61(9H, s) | — |
| 11-2 | — | CDCl$_3$*: 8.05(2H, d, J=9Hz), 7.4-7.2(5H, m), 7.19(2H, d, J=9Hz), 5.00(1H, s), 3.47(2H, s), 3.28(3H, s), 2.6-2.3(4H, m), 2.18(2H, s), 1.8-1.3(4H, m), 1.62(9H, s) | — |
| 11-3 | — | CDCl$_3$*: 7.84(2H, d, J=9Hz), 7.4-7.2(5H, m), 6.64(2H, d, J=9Hz), 3.6-3.5(2H, m), 3.52(2H, s), 2.98(3H, m), 2.7-2.6(2H, m), 2.4-2.3(2H, m), 1.8-1.5(6H, m), 1.56(9H, s) | — |
| 11-4 | — | CDCl$_3$*: 7.85(2H, d, J=9Hz), 6.65(2H, d, J=9Hz), 3.6-3.5(2H, m), 3.48(1H, s), 2.99(3H, s), 3.0-2.8(4H, m), 1.8-1.4(6H, m), 1.56(9H, s) | — |
| 13-1 | — | CDCl$_3$: 7.37-7.22(5H, m), 3.56(2H, s), 2.68-2.50(4H, m), 2.65(2H, s), 1.84(2H, ddd, J=13, 8, 4Hz), 1.55(2H, ddd, J=13, 5, 4Hz) | — |
| 13-2 | — | CDCl$_3$: 7.34-7.22(5H, m), 3.53(2H, s), 3.47(2H, s), 2.64(2H, ddd, J=12, 4, 4Hz), 2.36(2H, ddd, J=12, 7, 7Hz), 1.63(4H, dd, J=7, 4Hz) | 86.6-88.2 |
| 13-3 | — | CDCl$_3$*: 7.59(2H, d, J=9Hz), 7.36-7.23(5H, m), 6.97(2H, d, J=9Hz), 3.86(2H, s), 3.56(2H, s), 2.74-2.63(2H, m), 2.50-2.37(2H, m), 1.96(1H, brs), 1.85-1.71(4H, m) | — |
| 13-4 | — | DMSO-d$_6$: 7.87(2H, d, J=9Hz), 7.35-7.21(5H, m), 7.02(2H, d, J=9Hz), 4.55(1H, brs), 3.82(2H, s), 3.48(2H, s), 2.60-2.27(4H, m), 1.74-1.63(2H, m), 1.60-1.50(2H, m) | 131.1-132.3 |
| 13-5 | — | CDCl$_3$: 7.99(2H, d, J=9Hz), 7.35-7.24(5H, m), 6.92(2H, d, J=9Hz), 3.89(3H, s), 3.86(2H, s), 3.56(2H, s), 2.73-2.66(2H, m), 2.50-2.38(2H, m), 1.82-1.71(4H, m) | — |
| 13-6 | — | CDCl$_3$: 7.99(2H, d, J=9Hz), 6.93(2H, d, J=9Hz), 3.89(3H, s), 3.86(2H, s), 3.05(2H, ddd, J=12, 10, 4Hz), 2.90(2H, ddd, J=12, 4, 4Hz), 1.79-1.62(4H, m) | — |
| 20-1 | — | CDCl$_3$: 7.87(2H, d, J=9Hz), 7.35-7.22(5H, m), 6.81(2H, d, J=9Hz), 3.85(3H, s), 3.52(2H, s), 3.40(2H, s), 3.08(3H, s), 2.75-2.66(2H, m), 2.31(2H, ddd, J=12, 12, 3Hz), 1.82-1.57(4H, m), 1.54(1H, s) | — |
| 20-2 | — | CDCl$_3$: 7.88(2H, d, J=9Hz), 6.82(2H, d, J=9Hz), 3.85(3H, s), 3.40(2H, s), 3.10(3H, s), 3.02-2.83(4H, m), 1.70-1.57(4H, m) | — |
| 21-1 | — | CDCl$_3$: 7.88(2H, d, J=9Hz), 7.58(2H, d, J=8Hz), 7.34(2H, d, J=8Hz), 6.80(2H, d, J=9Hz), 4.6-4.5(1H, m), 3.86(3H, s), 3.7-3.6(1H, m), 3.5-3.3(3H, m), 3.1-3.0(2H, m), 3.08(3H, s), 3.0-2.9(1H, m), 2.7-2.6(2H, m), 1.83(1H, s), 1.7-1.4(4H, m) | — |
| 22-1 | — | CDCl$_3$: 7.90(2H, d, J=9Hz), 7.60(2H, d, J=9Hz), 7.01(2H, d, J=9Hz), 6.81(2H, d, J=9Hz), 4.78(1H, d, J=14Hz), 4.75(1H, d, J=14Hz), 4.5-4.4(1H, m), 3.87(3H, s), 3.8-3.7(1H, m), 3.5-3.3(3H, m), 3.1-3.0(1H, m), 3.08(3H, s), 1.8-1.5(4H, m) | — |
| 24-1 | — | CDCl$_3$: 7.87(2H, d, J=8Hz), 7.58(2H, d, J=8Hz), 7.37(2H, d, J=8Hz), 6.78(2H, d, J=8Hz), 4.6-4.4(1H, m), 3.85(3H, s), 3.78(2H, s), 3.7-3.6(1H, m), 3.5-3.3(3H, m), 3.05(3H, s), 3.0-2.9(1H, m), 1.8-1.5(3H, m), 1.4-1.3(1H, m) | — |
| 46-1 | — | CDCl$_3$*: 7.93(2H, d, J=9Hz), 7.41(2H, d, J=9Hz), 4.0-3.8(m), 3.91(3H, s), 3.2-3.1(2H, m), 3.15(2H, s), 1.7-1.4(4H, m), 1.45(9H, s) | — |
| 46-2 | — | CDCl$_3$: 8.25(2H, d, J=8Hz), 8.01(2H, d, J=8Hz), 3.98(3H, s), 3.9-3.8(2H, m), 3.3-3.2(2H, m), 3.29(2H, s), 2.0-1.9(2H, m), 1.7-1.6(2H, m), 1.45(9H, s) | — |
| 46-3 | — | DMSO-d$_6$: 8.18(2H, d, J=9Hz), 8.06(2H, d, J=9Hz), 5.23(1H, s), 3.91(3H, s), 3.67(2H, s), 3.2-2.9(4H, m), 2.0-1.8(4H, m) | — |

Structures of the compounds of the above Examples are shown in Charts 1 to 5. In the abbreviations of the substituents used in the structures, Me- means methyl group and $^t$Bu- means tert-butyl group.

CHART 1
Example 1,
Example 2,
Example 50
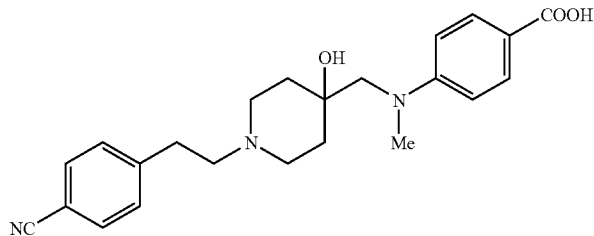
Example 3
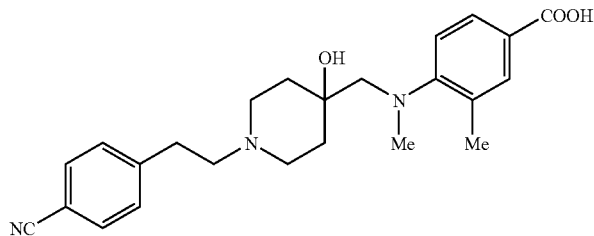
Example 4
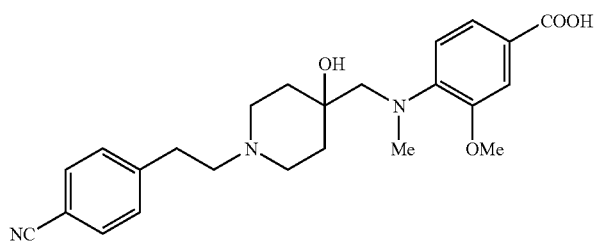
Example 5
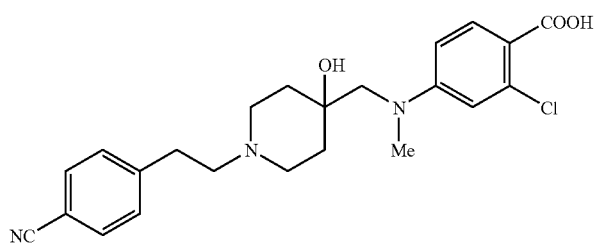
Example 6
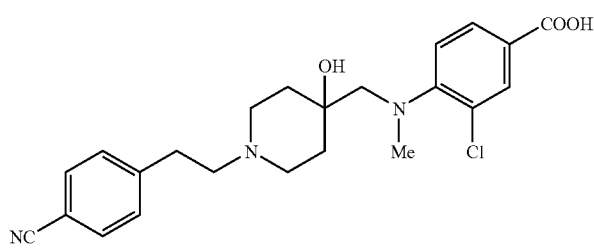
Example 7
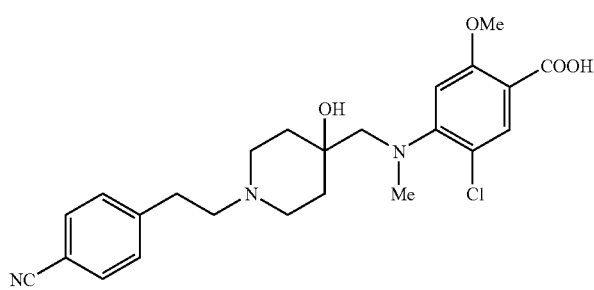

CHART 1-continued
Example 8
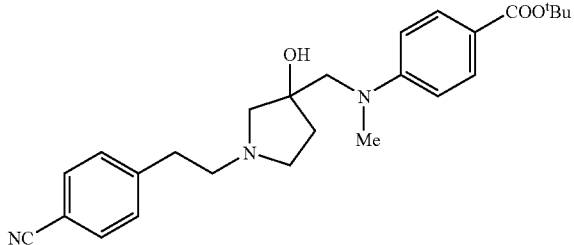
Example 9
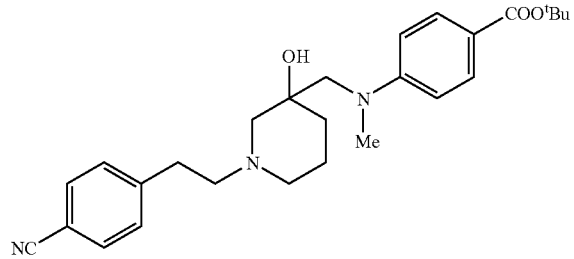
Example 10
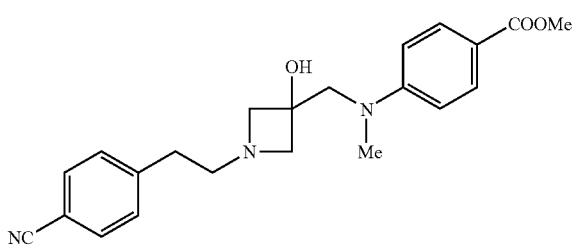
Example 11
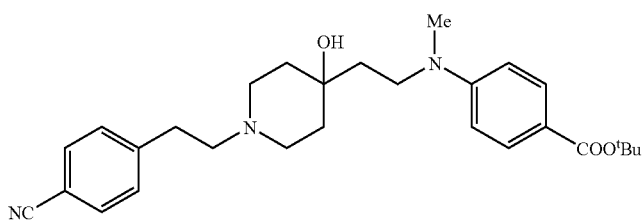
CHART 2
Example 12
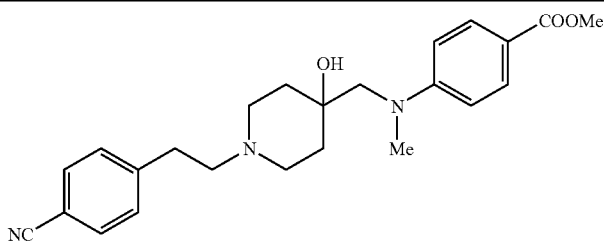
Example 13,
Example 19
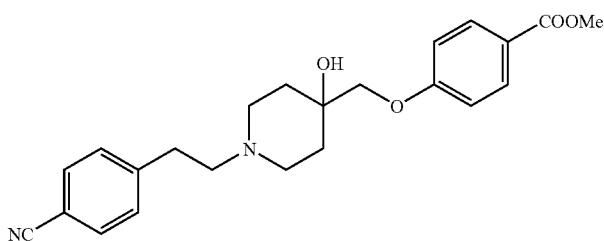

CHART 2-continued
Example 14
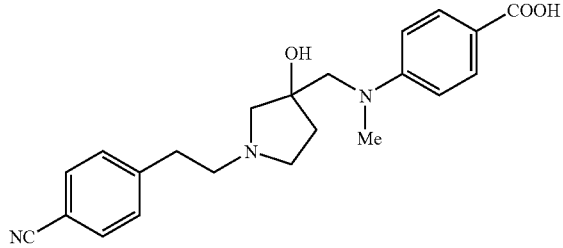
Example 15
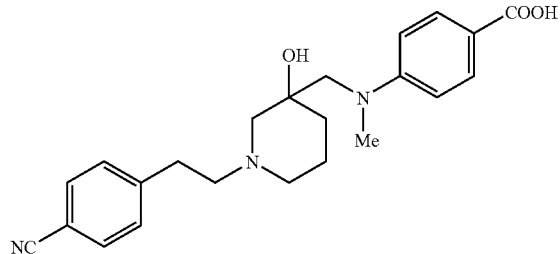
Example 16
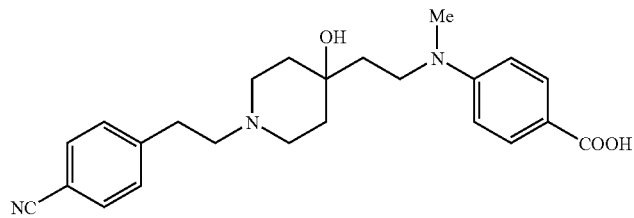
Example 17
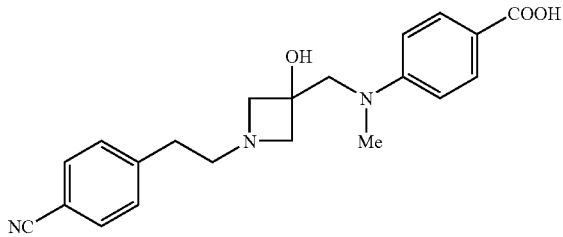
Example 18
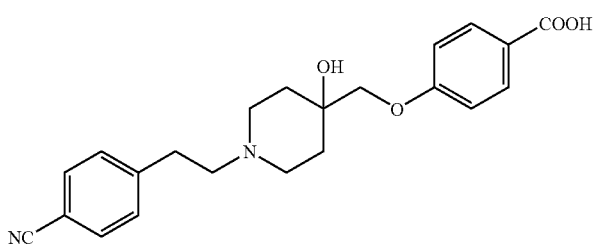
Example 20
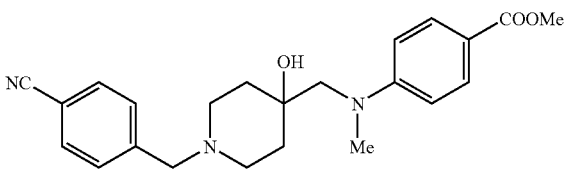
Example 21
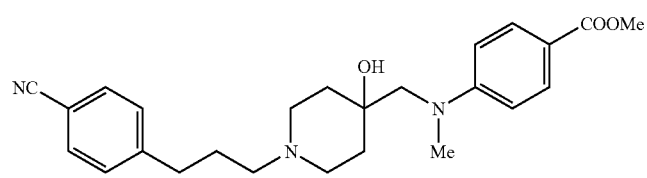

CHART 2-continued

Example 22

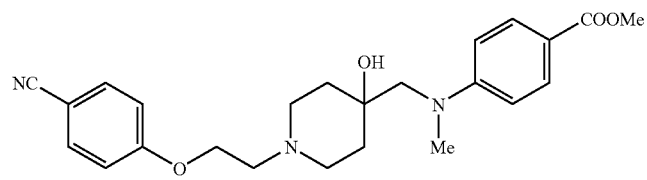

CHART 3

Example 23

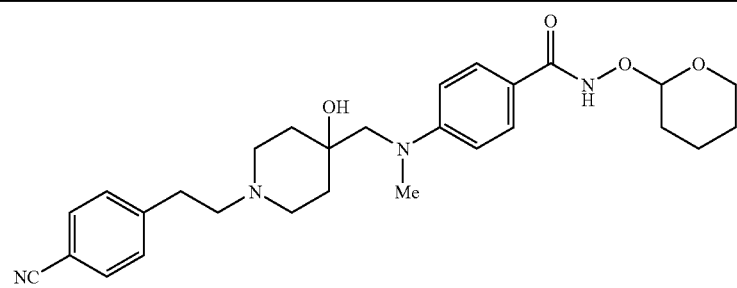

Example 24

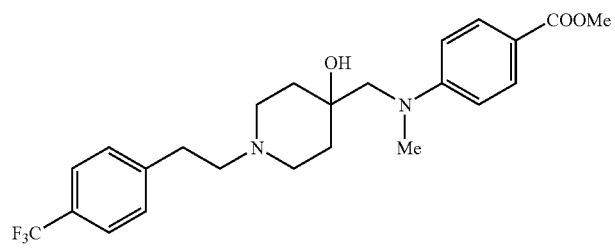

Example 25

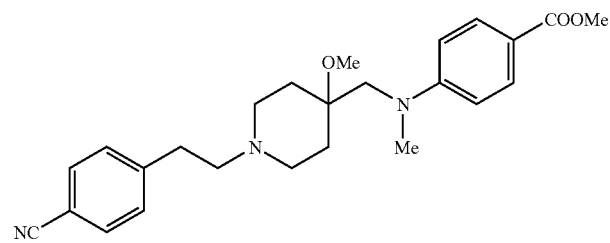

| Example 26 | monohydrochloride of compound of Example 1 |
| Example 27 | monohydrochloride of compound of Example 6 |
| Example 28 | monohydrochloride of compound of Example 7 |
| Example 29 | monohydrochloride of compound of Example 14 |
| Example 30 | monohydrochloride of compound of Example 15 |
| Example 31 | monohydrochloride of compound of Example 16 |
| Example 32 | monohydrochloride of compound of Example 3 |
| Example 33 | monohydrochloride of compound of Example 5 |
| Example 34 | monohydrochloride of compound of Example 17 |

CHART 4

Example 35

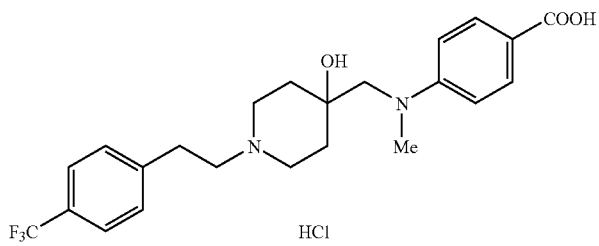

CHART 4-continued
Example 36
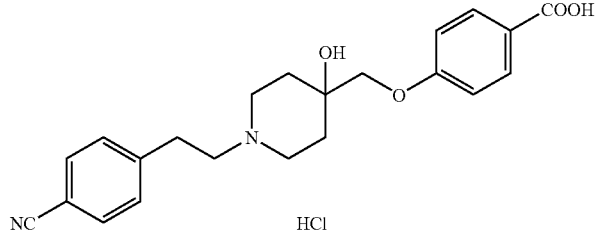
HCl
Example 37
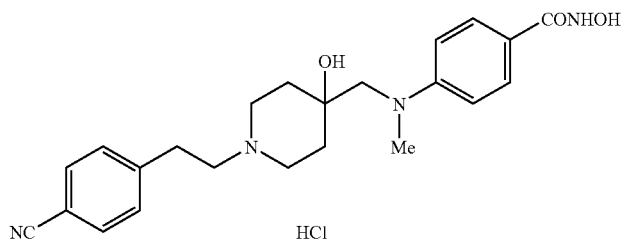
HCl
Example 38
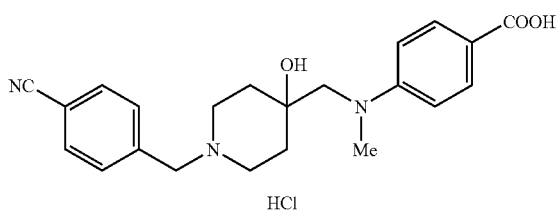
HCl
Example 39
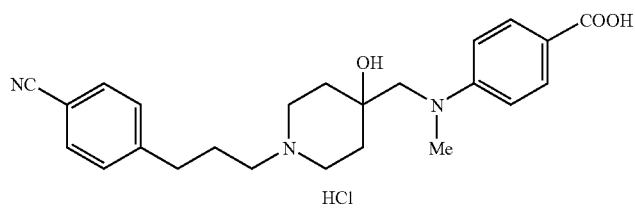
HCl
Example 40
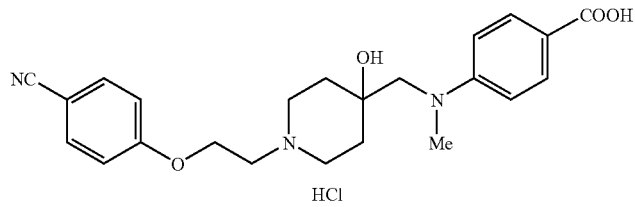
HCl
Example 41
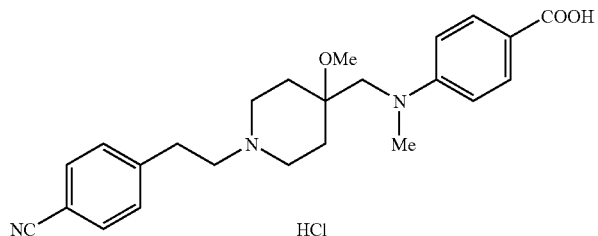
HCl
Example 42
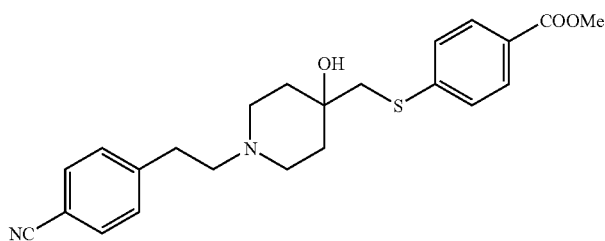

CHART 4-continued
Example 43
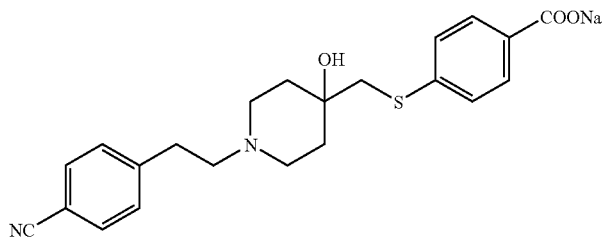
Example 44
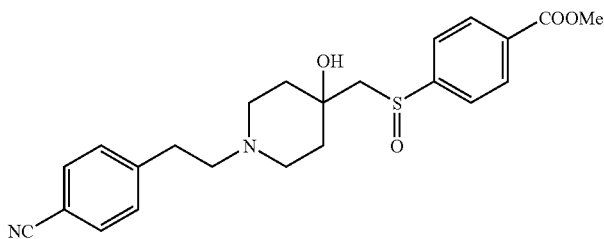
CHART 5
Example 45
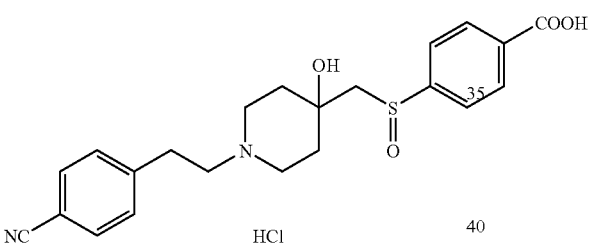
HCl
Example 46
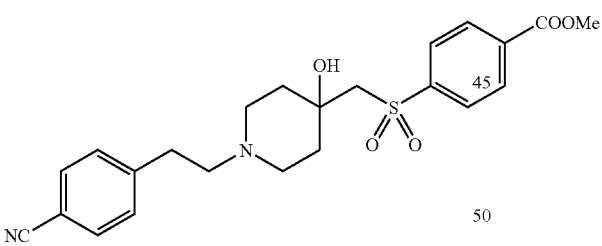
Example 47
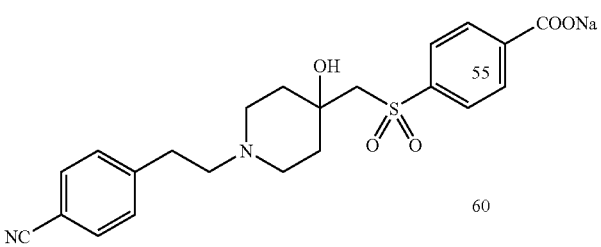
Example 48    monomethansulfonate of compound of Example 1
Example 49    monohydrochloride of compound of Example 1

Structures of intermediate compounds of the compounds of Example 1 to 46 are shown in Charts 6 to 10. Example 1-1 is a compound obtained in Step 1 of Example 1. In the abbreviations of the substituents used in the structures, Me- means methyl group and tBu- means tert-butyl group.
CHART 6
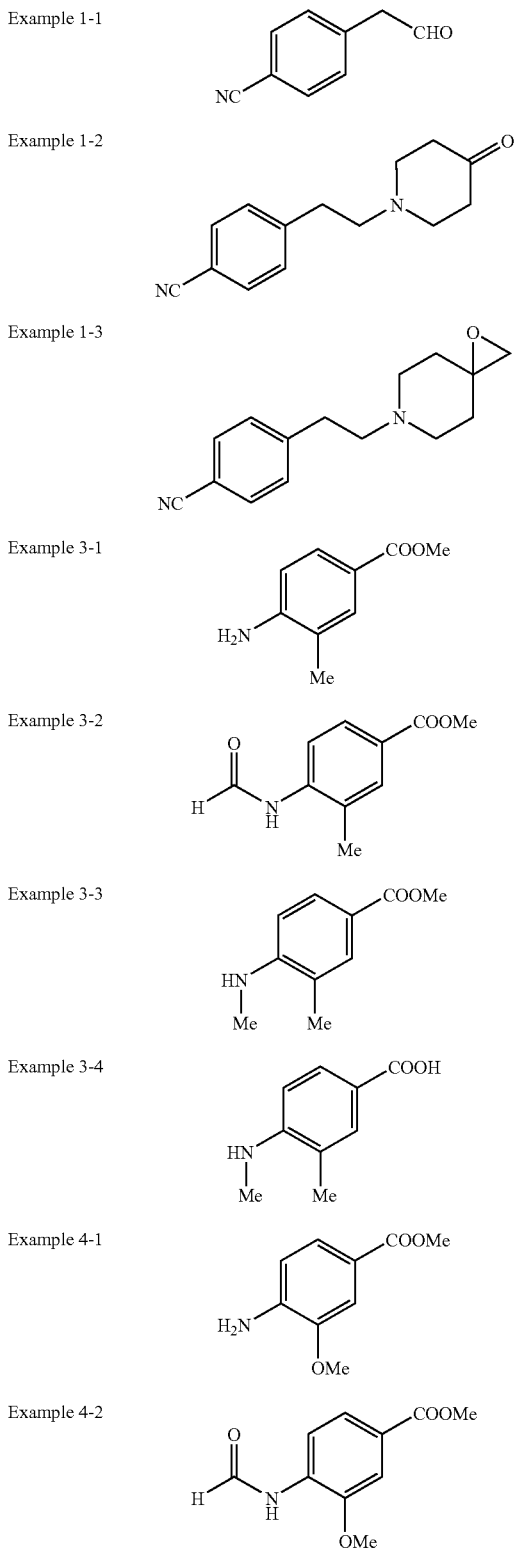
CHART 6-continued
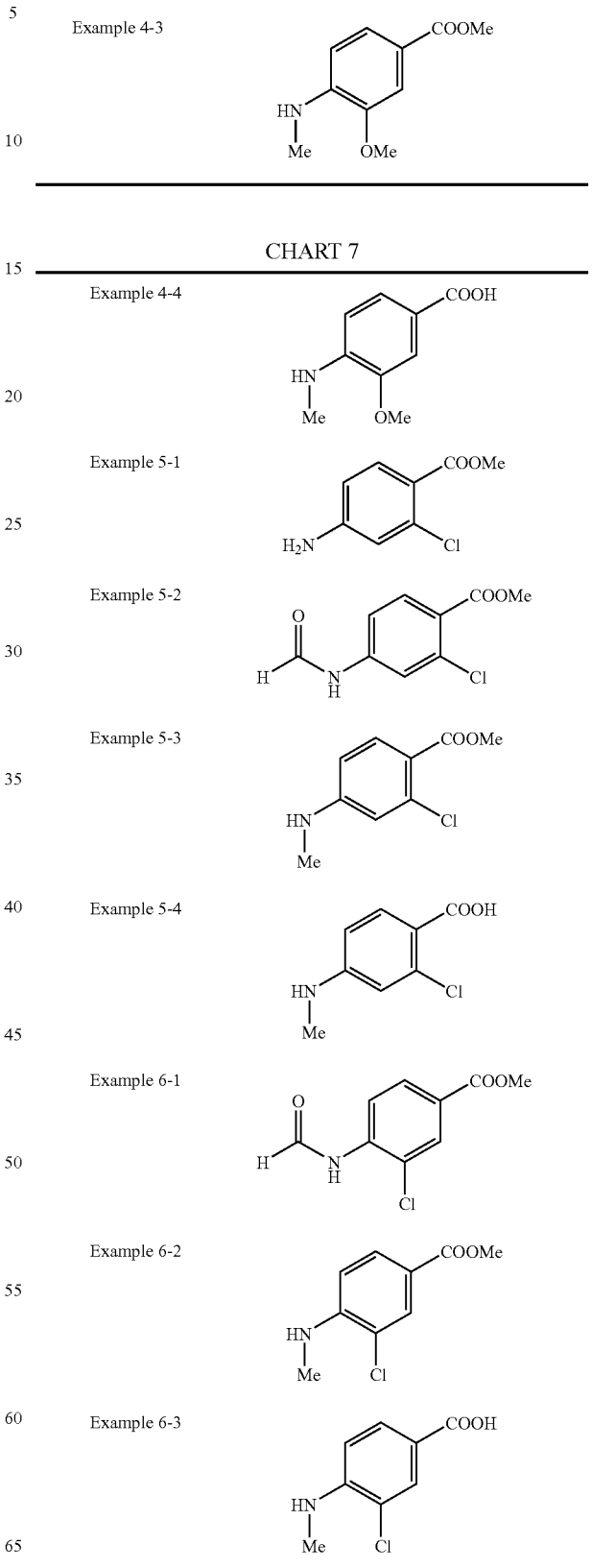

CHART 7-continued
Example 7-1
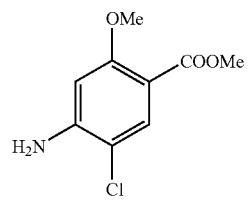
Example 7-2
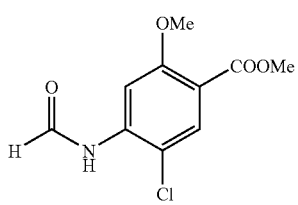
CHART 8
Example 7-3
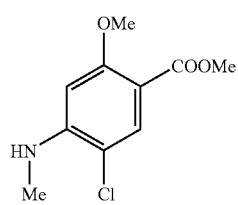
Example 7-4
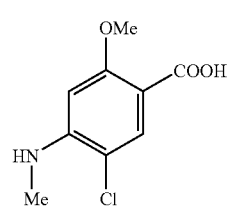
Example 8-1
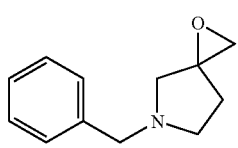
Example 8-2
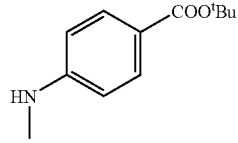
Example 8-3
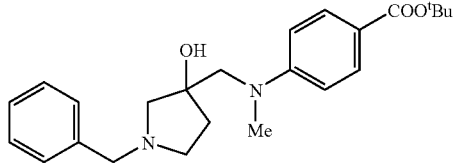
CHART 8-continued
Example 8-4
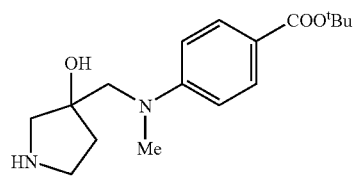
Example 9-1
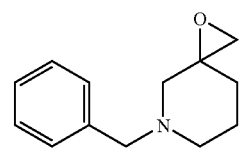
Example 9-2
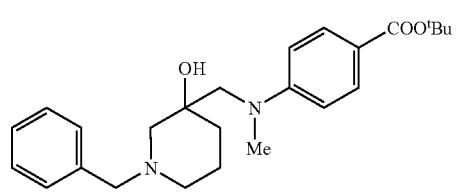
Example 9-3
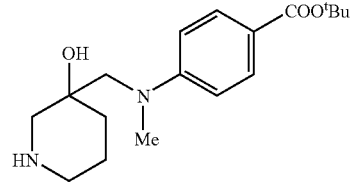
Example 10-1
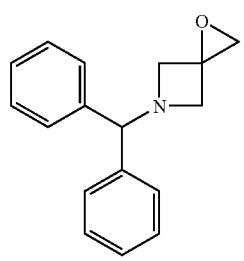

CHART 9
Example 10-2
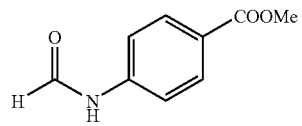
Example 10-3
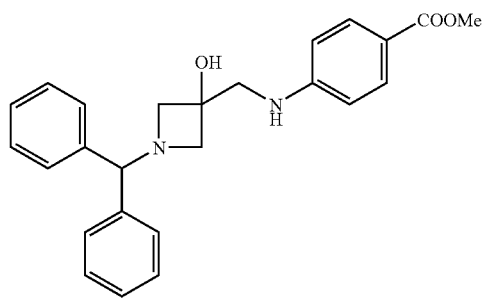
Example 10-4
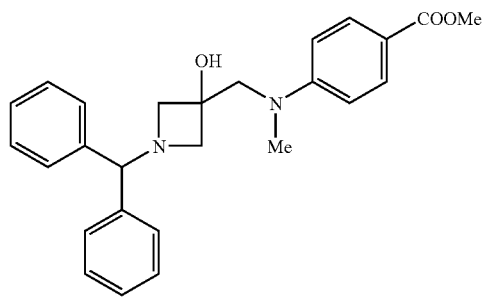
Example 10-5
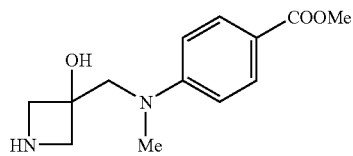
HCl
Example 11-1
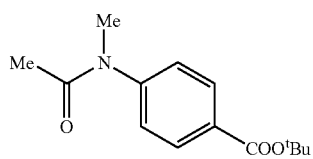
Example 11-2
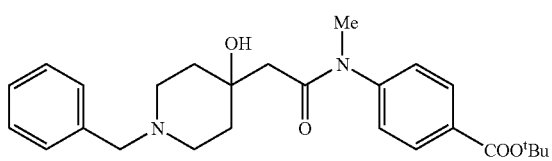
Example 11-3
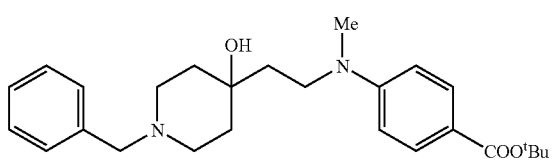
Example 11-4
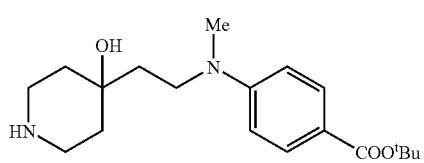

CHART 9-continued
Example 13-1
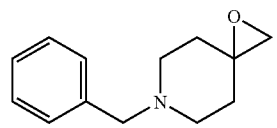
Example 13-2
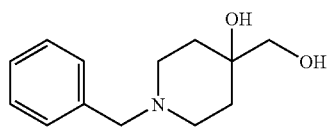
CHART 10
Example 13-3
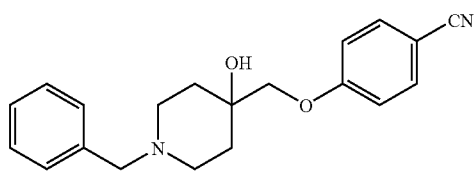
Example 13-4
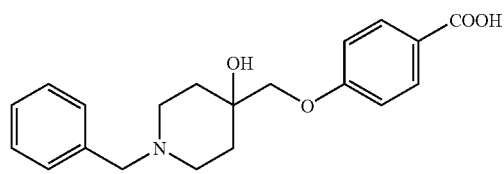
Example 13-5
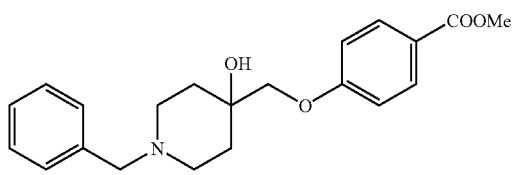
Example 13-6
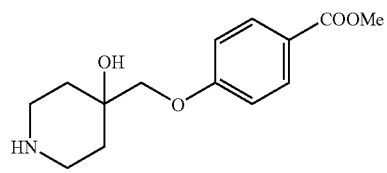
Example 20-1
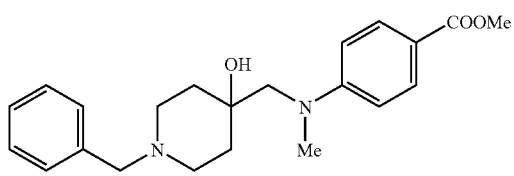
Example 20-2
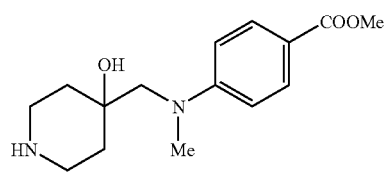

CHART 10-continued
Example 21-1
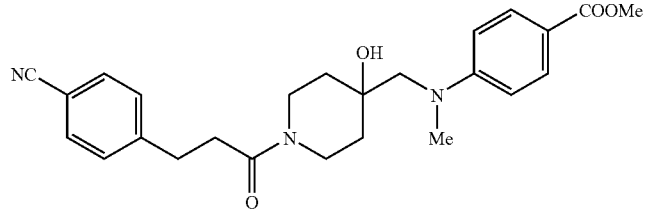
Example 22-1
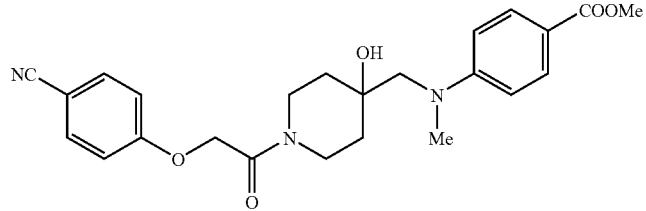
Example 24-1
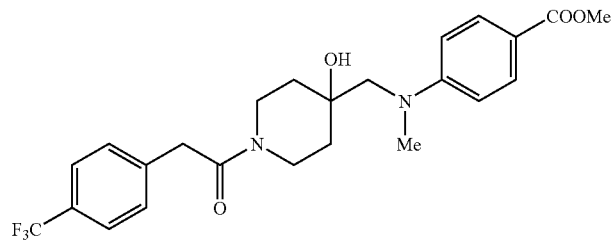
Example 46-1
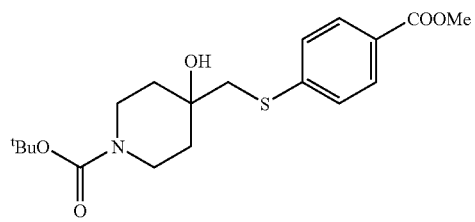
Example 46-2
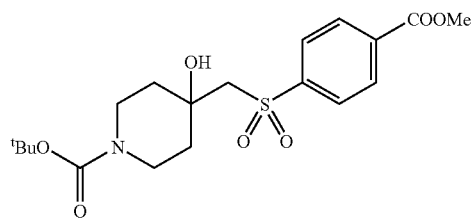
Example 46-3
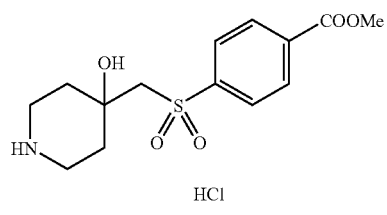

EXAMPLE OF FORMULATION

Examples of formulations containing the compounds of the present invention are shown below. However, the present invention is by no means restricted to these examples.

| Formulation Example 1: Tablets | |
|---|---|
| Compound of Example 26 | 100 g |
| Lactose | 137 g |
| Crystalline cellulose | 30 g |
| Hydroxypropyl cellulose | 15 g |
| Sodium carboxymethyl starch | 15 g |
| Magnesium stearate | 3 g |

These components are homogeneously mixed after weighing them. The mixture is ground to prepare a tablet weighing 150 mg.

| Formulation Example 2: Film-coating tablets | |
|---|---|
| Hydroxypropylmethyl cellulose | 9 g |
| Macrogol 6000 | 1 g |
| Titanium oxide | 2 g |

After weighing each component above, hydroxypropylmethyl cellulose and Macrogol 6000 are dissolved in water, and titanium oxide is dispersed therein. This solution is film-coated to 300 g of the tablets of Formulation Example 1 to prepare film-coated tablets.

| Formulation Example 3: Capsules | |
|---|---|
| Compound of Example 36 | 50 g |
| Lactose | 435 g |
| Magnesium stearate | 15 g |

These components above are homogeneously mixed after weighing them. Three hundred milligrams of the mixture is filled in the capsule-encapsulating machine to prepare a capsule.

| Formulation Example 4: Capsules | |
|---|---|
| Compound of Example 26 | 100 g |
| Lactose | 63 g |
| Corn starch | 25 g |
| Hydroxypropyl cellulose | 10 g |
| Talc | 2 g |

After weighing each component above, the compound of Example 26, lactose, and corn starch are homogeneously mixed. An aqueous solution of hydroxypropyl cellulose is added to this mixture, and granules are prepared by a wet-granulation method. The granules are homogeneously mixed with talc, and then 200 mg of them are filled in an appropriate hard capsule.

| Formulation Example 5: Powders | |
|---|---|
| Compound of Example 35 | 200 g |
| Lactose | 790 g |
| Magnesium stearate | 10 g |

The powders containing 20% of the effective ingredient are prepared by mixing each component homogeneously after weighing.

| Formulation Example 6: Granules and Fine granules | |
|---|---|
| Compound of Example 41 | 100 g |
| Lactose | 200 g |
| Crystalline cellulose | 100 g |
| Partly α-starch | 50 g |
| Hydroxypropyl cellulose | 50 g |

After weighing each component above, the compound of Example 41, lactose, crystalline cellulose, and partly α-starch are homogeneously mixed. An aqueous solution of hydroxypropyl cellulose (HPC) is added to this mixture, and granules or fine granules are prepared by the wet-granulation method. These are dried and formed into granules or fine granules.

| Formulation Example 7: Injections | |
|---|---|
| Compound of Example 48 | 2 g |
| Propylene glycol | 200 g |
| Distilled water for injection | proper volume |

The compound of Example 48 is dissolved in propylene glycol after weighing each component. Sterile water for injection is added to make a total volume of 1000 mL, and 5 mL each of the aqueous solution is dispensed in a 10 mL ampoule after filter sterilization, and then it is sealed closely in the ampoule to prepare an injection.

| Formulation Example 8: Dry Powder Inhalants | |
|---|---|
| Compound of Example 35 | 5 g |
| Lactose | 95 g |

The compound of Example 35 is homogenously mixed with lactose, and then the mixture is charged into a dry powder inhaler.

INDUSTRIAL APPLICABILITY

The compounds of the present invention exhibit potent antitussive effects on citric acid-induced cough reflex in guinea pigs and show no abnormality in the toxicological tests. In addition, they have good pharmacokinetic properties and less adverse actions.

The pharmaceutical compositions of the present invention can be used as antitussives for the treatment of respiratory diseases as follows; lung cancer, carcinomatous lymphopathy, rib fracture, spontaneous pneumothorax, cold syndrome (upper respiratory infection), pulmonary tuberculosis, interstitial pneumonitis, pleurisy, pneumonia, acute bronchitis, chronic bronchitis, pulmonary emphysema, pneumoconiosis, bronchiectasis, diffuse panbronchiolitis, bronchial asthma, pulmonary embolism, and pulmonary infarction. They are useful as agents for preventing and/or treating the respiratory diseases.

The invention claimed is:

1. A compound represented by following Formula (III):

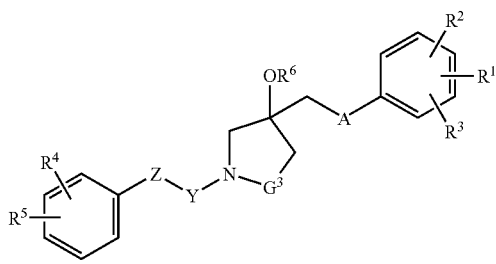

(III)

wherein A represents a group represented by L-W (wherein L represents a bond; and W represents a group represented by —$NR^7$— (wherein $R^7$ represents hydrogen atom or a lower alkyl group));

$G^3$ represents $(CH_2)m$ (wherein m denotes 0);

Y represents a lower alkylene group, or benzylidene group unsubstituted or substituted by $R^4$;

Z represents a bond or oxygen atom, wherein Y may form a 5- or 6-membered ring with carbon atoms on the benzene ring when Z represents a bond;

$R^1$ represents a nitro group, a lower alkoxycarbonyl group, carbamoyl group unsubstituted or mono- or di-substituted by lower alkyl groups, unprotected or protected hydroxyl group, unprotected or protected carboxyl group, unprotected or protected N-hydroxycarbamoyl group, a lower alkyl group substituted by unprotected or protected hydroxyl group, a lower alkyl group substituted by unprotected or protected carboxyl group, or a tetrazolyl group;

each of $R^2$ and $R^3$ independently represents a hydrogen atom, a halogen atom, a lower alkyl group unsubstituted or substituted by one or more halogen atoms, a lower alkoxy group unsubstituted or substituted by one or more halogen atoms, or a nitro group;

each of $R^4$ and $R^5$ independently represents a hydrogen atom, a halogen atom, a lower alkyl group unsubstituted or substituted by one or more halogen atoms, a lower alkoxy group unsubstituted or substituted by one or more halogen atoms, cyano group, or a lower alkylsulfonyl group; and $R^6$ represents a hydrogen atom or a lower alkyl group, a salt thereof or a solvate thereof.

2. The compound, a salt thereof or a solvate thereof according to claim 1, wherein Y in Formula (III) is a lower alkylene group, and Z in Formula (III) is a bond.

3. The compound, a salt thereof or a solvate thereof according to claim 2, wherein Y in Formula (III) is an ethylene group.

4. The compound, a salt thereof or a solvate thereof according to claim 1, wherein $R^2$, $R^3$, $R^5$ and $R^6$ in Formula (III) are all the hydrogen atom.

5. The compound, a salt thereof or a solvate thereof according to claim 1, wherein $R^1$ in Formula (III) is a nitro group, a lower alkoxycarbonyl group, a carbamoyl group unsubstituted or mono- or di-substituted by lower alkyl groups, unprotected or protected carboxyl group, or a tetrazolyl group.

6. The compound, a salt thereof or a solvate thereof according to claim 5, wherein $R^1$ in Formula (III) is a carboxyl group.

7. The compound, a salt thereof or a solvate thereof according to claim 6, wherein $R^1$ in Formula (III) is a carboxyl group substituted at the para-position with respect to a carbon atom to which A bonds.

8. The compound, a salt thereof or a solvate thereof according to claim 1, wherein $R^4$ in Formula (III) is a cyano group.

9. The compound, a salt thereof or a solvate thereof according to claim 8, wherein $R^4$ in Formula (III) is a cyano group substituted at the para-position with respect to a carbon atom to which Z bonds.

10. The compound, a salt thereof or a solvate thereof according to claim 1, wherein $R^7$ in Formula (III) is a hydrogen atom, a methyl group or an ethyl group.

11. The compound, a salt thereof or a solvate thereof according to claim 1, wherein Formula (III) represents 4-({1-[2-(4-cyanophenyl)ethyl]-3-hydroxyazetidin-3-ylmethyl}methylamino)benzoic acid.

12. The compound, a salt thereof or a solvate thereof according to claim 1, wherein Formula (III) represents methyl 4-({1-[2-(4-cyanophenyl)ethyl]-3-hydroxyazetidin-3-ylmethyl}methylamino)benzoate.

13. A pharmaceutical composition comprising at least one selected from the group of the compound, a pharmaceutically acceptable salt thereof or a solvate thereof according to claim 1 as an active ingredient.

* * * * *